US010668305B2

(12) United States Patent
Cheatham, III et al.

(10) Patent No.: US 10,668,305 B2
(45) Date of Patent: Jun. 2, 2020

(54) GARMENT SYSTEM INCLUDING AT LEAST ONE THERAPEUTIC STIMULATION DELIVERY DEVICE AND RELATED METHODS

(71) Applicant: Elwha LLC, Bellevue, WA (US)

(72) Inventors: Jesse R. Cheatham, III, Seattle, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Max N. Mankin, Seattle, WA (US); Nathan P. Myhrvold, Medina, WA (US); Tony S. Pan, Bellevue, WA (US); Robert C. Petroski, Seattle, WA (US); Elizabeth A. Sweeney, Seattle, WA (US); Clarence T. Tegreene, Mercer Island, WA (US); Nicholas W. Touran, Seattle, WA (US); Yaroslav A. Urzhumov, Bellevue, WA (US); Charles Whitmer, North Bend, WA (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 578 days.

(21) Appl. No.: 15/434,381

(22) Filed: Feb. 16, 2017

(65) Prior Publication Data
US 2017/0157430 A1    Jun. 8, 2017

Related U.S. Application Data

(63) Continuation-in-part of application No. 14/469,169, filed on Aug. 26, 2014, now Pat. No. 9,687,404.

(51) Int. Cl.
*A61N 7/00* (2006.01)
*A61N 1/04* (2006.01)
(Continued)

(52) U.S. Cl.
CPC .................. *A61N 7/00* (2013.01); *A61B 5/11* (2013.01); *A61F 7/02* (2013.01); *A61M 5/1723* (2013.01);
(Continued)

(58) Field of Classification Search
CPC ............ A61H 1/008; A61H 2201/1207; A61H 2201/1238; A61H 7/00; A61H 7/007;
(Continued)

(56) References Cited

U.S. PATENT DOCUMENTS

| 5,218,954 A | 6/1993 | van Bemmelen |
| 5,396,896 A | 3/1995 | Tumey et al. |

(Continued)

FOREIGN PATENT DOCUMENTS

| CA | 2 332 747 A1 | 4/2001 |
| CA | 2332747 | 4/2011 |

(Continued)

OTHER PUBLICATIONS

European Patent Office, Supplementary European Search Report, Pursuant to Rule 62 EPC; App. No. EP 15855573; dated May 25, 2018 (received by our Agent dated Jun. 8, 2018); pp. 1-12.
(Continued)

*Primary Examiner* — Steven O Douglas
(74) *Attorney, Agent, or Firm* — Dorsey & Whitney LLP

(57) ABSTRACT

Garment systems including a flexible compression garment, at least one sensor, and at least one therapeutic stimulation delivery device operable responsive to sensing feedback from the at least one sensor, effective to provide therapeutic
(Continued)

radiation to a body part of a subject. Methods of using such garment systems are also described.

46 Claims, 17 Drawing Sheets

(51) Int. Cl.
| | |
|---|---|
| *A61N 1/36* | (2006.01) |
| *A61N 2/00* | (2006.01) |
| *A61N 5/06* | (2006.01) |
| *A61F 7/02* | (2006.01) |
| *A61N 5/04* | (2006.01) |
| *A61M 35/00* | (2006.01) |
| *A61M 5/172* | (2006.01) |
| *A61B 5/11* | (2006.01) |
| *A61F 7/00* | (2006.01) |
| *A61H 11/00* | (2006.01) |

(52) U.S. Cl.
CPC ........... *A61M 35/00* (2013.01); *A61N 1/0476* (2013.01); *A61N 1/0484* (2013.01); *A61N 1/36021* (2013.01); *A61N 2/002* (2013.01); *A61N 2/008* (2013.01); *A61N 5/04* (2013.01); *A61N 5/06* (2013.01); *A61F 2007/0096* (2013.01); *A61F 2007/0233* (2013.01); *A61H 2011/005* (2013.01); *A61H 2201/10* (2013.01); *A61H 2201/1207* (2013.01); *A61H 2201/164* (2013.01); *A61H 2201/1604* (2013.01); *A61H 2201/165* (2013.01); *A61H 2201/1609* (2013.01); *A61H 2201/1619* (2013.01); *A61H 2201/1623* (2013.01); *A61H 2201/1635* (2013.01); *A61H 2201/5002* (2013.01); *A61H 2201/5007* (2013.01); *A61H 2201/5058* (2013.01); *A61H 2201/5082* (2013.01); *A61H 2201/5092* (2013.01); *A61H 2201/5097* (2013.01); *A61H 2230/207* (2013.01); *A61H 2230/25* (2013.01); *A61H 2230/50* (2013.01); *A61H 2230/60* (2013.01); *A61H 2230/65* (2013.01); *A61M 2230/005* (2013.01); *A61M 2230/208* (2013.01); *A61M 2230/50* (2013.01); *A61M 2230/63* (2013.01); *A61N 5/0613* (2013.01); *A61N 2005/0645* (2013.01); *A61N 2007/0021* (2013.01); *A61N 2007/0078* (2013.01); *A61N 2007/0086* (2013.01)

(58) Field of Classification Search
CPC ........ A61H 7/008; A61H 9/00; A61H 9/0157; A61H 9/02; A61H 9/0207; A61H 9/0214; A61H 9/50; A61H 9/5058; A61H 9/5071; A61H 9/0078; A61H 11/00; A61H 2003/043; A61H 2011/005; A61H 2201/0242; A61H 2201/165; A61H 2201/5035; A61H 2201/5061; A61H 2201/5084; A61H 2205/06; A61H 2205/08; A61H 2205/10; A61H 2209/00; A61N 1/0452; A61B 5/6895; A61B 5/6804; A61B 5/112; A61B 5/01; A61B 5/21; A61B 5/024; A61B 5/04001; A61B 5/0488; A61B 5/1036
See application file for complete search history.

(56) References Cited

U.S. PATENT DOCUMENTS

| | | |
|---|---|---|
| 5,971,937 A | 10/1999 | Ekstrom |
| 5,997,465 A | 12/1999 | Savage et al. |
| 7,328,708 B2 | 2/2008 | Malak |
| 8,079,969 B2 | 12/2011 | Rousso et al. |
| 8,233,976 B2 | 7/2012 | Dacey, Jr. et al. |
| 8,734,369 B2 | 5/2014 | Perry |
| 9,687,404 B2 | 6/2017 | Cheatham, III et al. |
| 9,717,642 B2 | 8/2017 | Deshpande |
| 2003/0120183 A1 | 6/2003 | Simmons |
| 2004/0044386 A1 | 3/2004 | Beens et al. |
| 2004/0138727 A1 | 7/2004 | Taboada et al. |
| 2004/0162583 A1 | 8/2004 | Bingham et al. |
| 2004/0230226 A1 | 11/2004 | Bingham et al. |
| 2005/0060030 A1 | 3/2005 | Lashinski et al. |
| 2005/0107831 A1 | 5/2005 | Hill et al. |
| 2005/0137656 A1 | 6/2005 | Malak |
| 2005/0154336 A1 | 7/2005 | Kloecker et al. |
| 2006/0058694 A1 | 3/2006 | Clark et al. |
| 2006/0079824 A1 | 4/2006 | Munch-Fals et al. |
| 2006/0122544 A1 | 6/2006 | Ciluffo |
| 2006/0293719 A1 | 12/2006 | Naghavi |
| 2007/0049853 A1 | 3/2007 | Adams et al. |
| 2007/0129776 A1 | 6/2007 | Robins et al. |
| 2007/0265140 A1 | 11/2007 | Kim et al. |
| 2008/0004679 A1 | 1/2008 | Naghavi et al. |
| 2008/0214971 A1 | 9/2008 | Talish et al. |
| 2008/0215115 A1 | 9/2008 | Bingham et al. |
| 2008/0319359 A1 | 12/2008 | Moomiaie-Qajar et al. |
| 2009/0036938 A1 | 2/2009 | Shipley et al. |
| 2009/0234262 A1 | 9/2009 | Reid, Jr. et al. |
| 2009/0234265 A1 | 9/2009 | Reid, Jr. et al. |
| 2010/0056966 A1 | 3/2010 | Toth |
| 2010/0185220 A1 | 7/2010 | Naghavi et al. |
| 2010/0305484 A1 | 12/2010 | Grollier et al. |
| 2011/0046432 A1 | 2/2011 | Simon et al. |
| 2011/0066091 A1 | 3/2011 | Larson |
| 2011/0092337 A1 | 4/2011 | Srivasan et al. |
| 2011/0120567 A1 | 5/2011 | Kuehne et al. |
| 2011/0172752 A1 | 7/2011 | Bingham et al. |
| 2011/0196269 A1 | 8/2011 | Arkans |
| 2011/0278943 A1 | 11/2011 | Eckhoff et al. |
| 2011/0278957 A1 | 11/2011 | Eckhoff et al. |
| 2011/0307037 A1 | 12/2011 | Mussivand |
| 2012/0065561 A1 | 3/2012 | Ballas et al. |
| 2012/0071743 A1 | 3/2012 | Todorov et al. |
| 2012/0078145 A1 | 3/2012 | Malhi et al. |
| 2012/0089063 A1 | 4/2012 | Olson |
| 2012/0130203 A1 | 5/2012 | Stergiou et al. |
| 2012/0203132 A1 | 8/2012 | Blumensohn et al. |
| 2012/0253236 A1 | 10/2012 | Snow et al. |
| 2012/0290051 A1 | 11/2012 | Boyden et al. |
| 2013/0041235 A1 | 2/2013 | Rogers et al. |
| 2013/0072301 A1 | 3/2013 | Mallinson |
| 2013/0072838 A1 | 3/2013 | Fischer et al. |
| 2013/0158444 A1 | 6/2013 | Herr et al. |
| 2013/0211259 A1 | 8/2013 | Komistek et al. |
| 2013/0289456 A1 | 10/2013 | Chang Guo et al. |
| 2013/0306614 A1 | 11/2013 | Fey, Jr. |
| 2013/0310719 A1 | 11/2013 | Davis et al. |
| 2013/0345610 A1 | 12/2013 | Larson et al. |
| 2014/0018889 A1 | 1/2014 | Unetich et al. |
| 2014/0070957 A1 | 3/2014 | Longinotti-Buitoni et al. |
| 2014/0135593 A1 | 5/2014 | Jayalth et al. |
| 2014/0140567 A1 | 5/2014 | LeBoeuf et al. |
| 2014/0142459 A1 | 5/2014 | Jayalth et al. |
| 2014/0207036 A1 | 7/2014 | Perry et al. |
| 2014/0213940 A1 | 7/2014 | Mayer |
| 2014/0276283 A1 | 9/2014 | Mansur, Jr. et al. |
| 2014/0330186 A1 | 11/2014 | Hyde et al. |
| 2015/0073907 A1 | 3/2015 | Purves et al. |
| 2015/0173993 A1 | 6/2015 | Walsh et al. |
| 2015/0297437 A1 | 10/2015 | Neuenhahn |
| 2015/0351690 A1 | 12/2015 | Toth et al. |
| 2016/0015280 A1 | 1/2016 | Hyde et al. |
| 2017/0209301 A1 | 7/2017 | DeSeve |

FOREIGN PATENT DOCUMENTS

| | | |
|---|---|---|
| CN | 101039641 A | 9/2007 |
| CN | 101248989 A1 | 8/2008 |

(56) References Cited

FOREIGN PATENT DOCUMENTS

| WO | WO 2013/033669 A2 | 3/2013 |
|---|---|---|
| WO | 2014/041032 | 3/2014 |
| WO | WO 2014/066077 A1 | 5/2014 |

OTHER PUBLICATIONS

Chinese State Intellectual Property Office, Notification of Second Office Action, App. No. 201580057646.6 (based on PCT Patent Application No. PCT/2015/046717); dated Jul. 23, 2019 (received by our Agent dated Aug. 1 2019); pp. 1-14 (machine translation provided).
PCT International Search Report; International App. No. PCT/US2018/018115; dated Jun. 27, 2018; pp. 1-5.
European Patent Office, Extended European Search Report, Pursuant in Rule 62 EPC; App. No. EP 15 83 6158; dated Mar. 21, 2018; pp. 1-7.
PCT International Search Report; International App. No. PCT/US2015/057954; dated Feb. 4, 2016; DD. 1-4.
PCT International Search Report; International App. No. PCT/US2015/046717; dated Nov. 30, 2015; pp. 1-3.
Vanhemert "Coming Soon: Workout Gear That Monitors Your Muscles" Dec. 4, 2013; Wired, 4 pages, http://www.wired.corn/2013/12/these-smart-gyrn-clothes-are-the-future -ofwearable-cornputers/.
New Scale Technologies "Squiggle micro motor technology: Patented piezoelectric motor with small size, high force speed" Available as of Aug. 26, 2014, 3 pages. http://www.newscaletech.com/technology/sguiggle-rnotors.php.
New Scale Technologies, Thomasnet.com "New Drive Solutions for Squiggle® Micro Motors Add Speed Control Options, Dynamic Optimization of Motor Performance over Temperature" Jul. 21, 2009, 2 pages. http://news.thomasnet.com/company_story/New-Drive-Solutions-for-Squiggle-Micro-Motors-Add-Speed-Control-Options-Dynamic-Optimization-of-Motor-Performance-over-Ternperatue-828373.
Pi, www.pi.ws "Piezo Motor Solutions for Automation & Ultra-Precision Motion Control" Available as of Aug. 26, 2014, 4 pages. http://www.piezo-rnotor.net/piezo-motor ultrasonic and ultra-precision stepping.htm.
Pi, www.pi.ws "PILine Ultrasonic Piezomotor Working Principle" Available as of Aug. 26, 2014, 2 pages http://www.physikinstrurnente.com/en/products/piezo motor/piline.php.
Kim, et al. "Epidermal Electronics" Science 333, 838-843 (2011).
Hamaoka, et al. "The use of muscle near-infrared spectroscopy in sport, health and medical sciences: recent developments", Phil. Trans. R. Soc. A (2011) 369, 4591-4604.
Harrison, et al. "Portable acoustic myography—a realistic noninvasive method for assessment of muscle activity and coordination in human subjects in most home and sports settings" Physiological Reports, vol. 1, Issue 2: e00029, pp. 1-9 (2013).
Chen, et al. "A brief review of actuation at the micro-scale using electronics, electromagnetics and piezoelectric ultrasonics" Acoust. Sci. & Tech. 31, 2 (2010).
Chinese State Intellectual Property Office, Notification of First Office, App. No. 201580057646.6 (based on PCT Patent Application No. PCT/2015/046717); dated Nov. 29, 2018; pp. 1-13 (machine translation provided).
Chinese State Intellectual Property Office, Notification of the First Office Action, App. No. 201580064917.0 (based on PCT App. No. PCT/US2015/057954); dated Sep. 2, 2019 (received by our Agent dated Sep. 10, 2019); pp. 1-10 (machine translation provided).

GARMENT SYSTEM INCLUDING AT LEAST ONE THERAPEUTIC STIMULATION DELIVERY DEVICE AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

For purposes of the USPTO extra-statutory requirements, the present application constitutes a continuation-in-part of U.S. patent application Ser. No. 14/469,169, entitled GARMENT SYSTEM INCLUDING AT LEAST ONE MUSCLE OR JOINT ACTIVITY SENSOR AND AT LEAST ONE ACTUATOR RESPONSIVE TO THE SENSOR AND RELATED METHODS, filed Aug. 26, 2014, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Compression garments including clothing articles, such as socks, arm sleeves, leg sleeves, etc., can provide support to muscles of a body part on which the compression garments are worn. This support can be useful for people who have to stand for long periods, or people with circulation problems.

Compression sportswear, which is a specific type of compression garment, can also be worn by athletes during exercise. For example, bicycling shorts are a common type of compression sportswear. Compression sportswear can improve muscle functioning, and prevent chafing and rashes during and after exercise.

Compression garments are believed to have a number of positive effects on a user. For example, compression garments can help relieve pain from muscle stiffness and soreness, and reduce time taken for muscles to repair themselves. Also, when an appropriate amount of compression is used, compression garments can improve venous return and oxygenation to working muscles.

SUMMARY

Embodiments disclosed herein relate to a garment system including at least one muscle or at least one joint activity sensor, and at least one actuator that operates responsive to sensing feedback from the at least one muscle or the at least one joint activity sensor to cause a flexible compression garment to selectively compress against or selectively relieve compression against at least one body part of a subject. Such selective compression or relief of compression against the at least one body part can improve muscle functioning, joint functioning, or can be used for training or teaching an activity (e.g., a sport) or for rehabilitation.

Embodiments disclosed herein also relate to a garment system including at least one sensor, and at least one therapeutic stimulation delivery device ("TSDD") that selectively operates responsive to sensing feedback from the collected from at least one body part of a subject. Such selective operation can be used to provide therapeutic (e.g., preventative or palliative) treatment to the at least one body part.

In an embodiment, a garment system includes at least one flexible compression garment configured to be worn on at least one body part of a subject, one or more activity sensors supported by the at least one flexible compression garment, one or more actuators positioned relative to the at least one flexible compression garment and configured to cause the at least one flexible compression garment to selectively compress against or selectively relieve compression against the at least one body part, and a control system operably coupled to the one or more actuators and further operably coupled to the one or more activity sensors to receive the one or more sensing signals therefrom. The at least one flexible compression garment defines an interior space configured to receive the at least one body part. The one or more activity sensors are positioned and configured to sense at least one characteristic of at least one muscle or at least one joint of the at least one body part that is related to muscle activity or joint activity thereof, with the one or more activity sensors being further configured to output one or more sensing signals indicative of the at least one characteristic. The control system includes control electrical circuitry configured to direct the one or more actuators to cause the at least one flexible compression garment to selectively compress against or selectively relieve compression against the at least one body part responsive to the one or more sensing signals from the one or more activity sensors.

In an embodiment, a method of using a garment system is disclosed. At least one flexible compression garment of the at least one garment system is worn on at least one body part of a subject. The garment system includes one or more activity sensors configured to sense at least one characteristic of at least one muscle or at least one joint of the at least body part that is related to muscle activity or joint activity thereof and one or more actuators configured to cause the at least one flexible compression garment to selectively compress against or selectively relieve compression against the at least one body part. The at least one characteristic of the at least one muscle or the at least one joint of the at least one body part is sensed with the one or more activity sensors.

Responsive to sensing the at least one characteristic via the one or more activity sensors, the one or more actuators are actuated to cause the at least one flexible compression garment to selectively compress against or selectively relieve compression against the at least one body part.

In an embodiment, a garment system for delivering therapeutic stimulation to a subject is disclosed. The garment system includes at least one flexible compression garment configured to be worn on at least one body part of the subject, the at least one flexible compression garment defining an interior space configured to receive the at least one body part. The garment system includes one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system includes at least one TSDD positioned and configured to apply radiation to the at least one body part. The garment system includes a controller operably coupled to the at least one TSDD and the one or more sensors to receive the one or more sensing signals therefrom, the controller including control electrical circuitry configured to direct the at least one TSDD to selectively apply radiation to a region of the at least one body part responsive to the one or more sensing signals.

In an embodiment, a garment system for delivering therapeutic stimulation to a subject is disclosed. The garment system includes at least one flexible compression garment configured to be worn on at least one body part of a subject, the at least one flexible compression garment defining an interior space configured to receive the at least one body part. The garment system includes one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system includes at least one TSDD positioned and configured to apply radiation to a region of the at least one body part. The garment system includes a controller operably coupled to the at least one TSDD and the one or more sensors to receive the one or more sensing signals therefrom. The controller of the garment system includes processing electrical circuitry configured to direct the at least one TSDD to selectively apply radiation to the region of the at least one body part, responsive to one or more sensing signals. The controller of the garment system includes a memory storage medium operably coupled to the processing electrical circuitry, the memory storage medium having one or more machine readable programs thereon, wherein the processing electrical circuitry is configured to execute the one or more machine readable programs. The controller of the garment system includes a power supply operably coupled to the controller, the one or more sensors, and the at least one TSDD.

In an embodiment, a method is disclosed. At least one flexible compression garment of a garment system is received on at least one body part of a subject. The garment system includes one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system further includes at least one TSDD positioned and configured to provide radiation to a region of the at least one body part. With the one or more sensors, one or more of the at least one characteristic of the at least one body part that is related to at least one of movement or a physiological state of the at least one body part is sensed. Responsive to sensing the at least one characteristic via the one or more sensors, the at least one TSDD is actuated to initiate, alter, or terminate application of radiation to the at least one body part. The method includes selectively emitting the radiation to the at least one body part from the at least one TSDD.

In an embodiment, a system for delivering therapeutic stimulation to a subject is disclosed. The garment system includes at least one flexible compression garment configured to be worn on at least one body part of the subject, the at least one flexible compression garment defining an interior space configured to receive the at least one body part. The garment system includes one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system includes an array of TSDDs positioned and configured to dynamically apply therapeutic radiation to the at least one body part. The garment system includes a controller operably coupled to the one or more sensors to receive the one or more sensing signals therefrom and the array of TSDDs, the controller including control electrical circuitry configured to direct the array of TSDDs to dynamically apply the therapeutic radiation to a region of the at least one body part responsive to one or more sensing signals.

In an embodiment, a garment system for delivering therapeutic stimulation to a subject is disclosed. The garment system includes at least one flexible compression garment configured to be worn on at least one body part of the subject. The garment system includes one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system includes an array of steerable ultrasound transducers positioned and configured to selectively apply therapeutic ultrasonic radiation to one or more selected regions of the at least one body part. The garment system includes a controller operably coupled to the one or more sensors to receive the one or more sensing signals therefrom and the array of steerable ultrasound transducers. The controller of the garment system includes processing electrical circuitry configured to direct the array of steerable ultrasound transducers to selectively aim and emit radiation to the one or more selected regions of the at least one body part responsive to one or more sensing signals. The controller of the garment system includes a memory storage medium operably coupled to the processing electrical circuitry, the memory storage medium having one or more machine readable programs stored therein, wherein the processing electrical circuitry is configured to execute the one or more machine readable programs. The controller of the garment system includes a power supply operably coupled to the controller, the one or more sensors, and the array steerable of ultrasound transducers.

In an embodiment, a method of selectively and dynamically providing therapeutic ultrasonic radiation is disclosed. At least one flexible compression garment of a garment system is received on at least one body part of a subject. The garment system includes one or more sensors configured to sense one or more of at least one characteristic of the at least one body part that is related to at least one of movement or a physiological state of the at least one body part, the one or more sensors further configured to output one or more sensing signals indicative of the at least one characteristic. The garment system includes an array of ultrasound transducers positioned and configured to provide therapeutic ultrasonic radiation to at least a region of the at least one body part. With the one or more sensors, one or more of the at least one characteristic of the at least one body part that is related to at least one of movement or a physiological state of the at least one body part is sensed. Responsive to sensing the at least one characteristic via the one or more sensors, the array of ultrasound transducers is actuated to initiate, alter, or terminate application of the therapeutic ultrasonic radiation to the at least one body part. The therapeutic ultrasonic radiation from the array of ultrasound transducers is emitted into at least a first region of the at least one body part responsive to actuating the array of ultrasound transducers. Emission of the therapeutic ultrasonic radiation to alter one or more of a wavelength, a frequency, or an intensity thereof or alter a target location of the therapeutic ultrasonic radiation from the first region to at least a second region of the at least one body part is selectively controlled.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
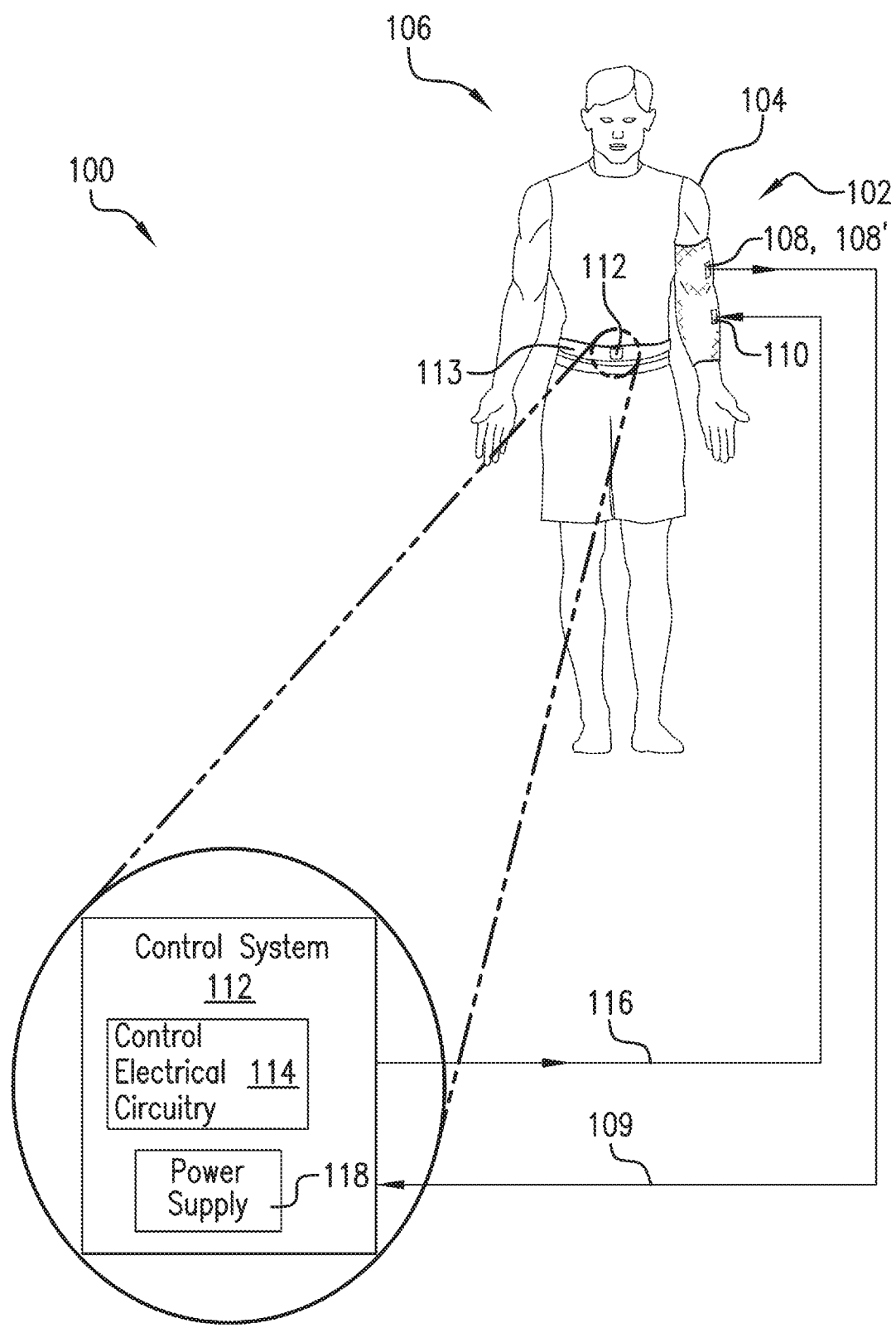
FIG. 1 is a diagrammatic view of a garment system, according to an embodiment.

Embodiments disclosed herein relate to a garment system including at least one muscle or at least one joint activity sensor, and at least one actuator that operates responsive to sensing feedback from the at least one muscle or the at least one joint activity sensor to cause a flexible compression garment to selectively compress against or selectively relieve compression against at least one body part of a subject. Such garment systems can selectively provide or relieve compression against the at least one body part. Such selective compression or relief of compression against the at least one body part can improve muscle functioning or joint functioning, or can be used for training or teaching an activity (e.g., a sport) or for rehabilitation. Embodiments disclosed herein also relate to methods of using such garment systems.

Embodiments disclosed herein also relate to a garment system including at least one sensor, and at least one TSDD that selectively operates responsive to sensing feedback from the collected from at least one body part of a subject, a pre-programmed action, or receiving impute from a remote control, a computer, or a user. Such selective operation can be used to provide therapeutic (e.g., preventative or palliative) treatment to the at least one body part.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 is an illustration of a garment system 100, according to an embodiment. The garment system 100 includes a flexible compression garment 102 that is configured to be worn on at least one body part 104 of a subject 106 during use. The flexible compression garment 102 can be substantially tubular and configured to generally conform to the at least one body part 104 when worn thereon.

The flexible compression garment 102 can be made from any suitable material. For example, the flexible compression garment 102 can be made from neoprene, nylon, synthetic rubber, or any other suitable synthetic or natural fabric, film, or polymeric material.

In the illustrated embodiment, the at least one body part 104 is an arm of the user, which includes a portion of the subject's 106 upper arm, forearm, and elbow joint therebetween that is received by the flexible compression garment 102. However, as discussed in more detail below, the garment systems disclosed herein can be employed on many other types of body parts. For example, the at least one body part 104 of the subject 106 can include at least a portion of a thigh and/or at least a portion of a lower leg, or at least a portion of a neck. As another example, the flexible compression garment 102 can be configured as a shirt, and the at least one body part 104 includes at least the chest of the subject 106. In an embodiment, the at least one flexible compression garment 102 can include a portion that is substantially tubular and configured to generally conform to the at least one body part of the subject 106, wherein the at least one body part includes at least a portion of an arm, at least a portion of an elbow, at least a portion of a forearm, at least a portion of a wrist, at least a portion of a hand, at least a portion of a finger, at least a portion of a thigh, at least a portion of a knee, at least a portion of a lower leg, at least a portion of a foot, at least a portion of a toe, at least a portion of a neck, at least a portion of a back, at least a portion of a head, at least a portion of a spine, or at least a portion of a chest of the subject 106.

The garment system 100 includes one or more activity sensors 108 that can be mounted on, embedded in, or otherwise supported by the flexible compression garment 102. The one or more activity sensors 108 are positioned and configured relative to the at least one body part 104 to sense at least one characteristic of at least one muscle or at least one joint of the at least body part 104 that is related to muscle activity or joint activity thereof of the at least body part 104 of the subject 106. For example, each or some of the one or more activity sensors 108 can be positioned adjacent to or proximate to the at least one muscle or the at least one joint of which activity is desired to be monitored. During use, the one or more activity sensors 108 output one or more sensing signals 109 indicative of the at least one characteristic. It is noted that the at least one muscle or at least one joint of which activity is to be sensed can include a plurality of muscles or a plurality joints. For example, in the case where the flexible compression garment 102 receives at least a portion of an upper arm and at least a portion of a forearm of the subject 106, the at least one muscle of the at least one body part 104 can include a plurality of muscles in each of the upper arm and lower arm of the at least one body part 104 and the at least one joint of the at least one body part 104 can include the elbow joint.

The garment system 100 further includes one or more actuators 110. The one or more actuators 110 are positioned relative to the flexible compression garment 102 and configured to cause the flexible compression garment 102 to selectively compress against or selectively relieve compression against the at least one body part 104 responsive to the one or more sensing signals 109 output by the one or more activity sensors 108. For example, the one or more actuators 110 can be embedded in the flexible compression garment 102, mounted interiorly inside of the flexible compression garment 102 in an interior space thereof in which the at least one body part 104 is received, or mounted exteriorly on the flexible compression garment 102.

The garment system 100 further includes a control system 112 operably coupled to the one or more activity sensors 108 and the one or more actuators 110. For example, the control system 112 can be wireless operably coupled to the one or more activity sensors 108 and the one or more actuators 110 or operably coupled via a wired connection, such as electrical wires. For example, the control system 112 can be sized and configured to be conveniently worn or carried by the subject 106, such as via straps 113 shown on the subject 106 in FIG. 1.

In an embodiment, the control system 112 further includes control electrical circuitry 114 configured to direct the one or more actuators 110 via one or more actuation signals 116 to cause the flexible compression garment 102 to selectively compress against or selectively relieve compression against the at least one body part 104 responsive to receiving the one or more sensing signals 109 from the one or more activity sensors 108. In an embodiment, the control system 112 further includes a power supply 118 (e.g., a battery, micro-battery, a thin film battery, a stretchable/flexible power supply, a fuel cell, an energy harvester, a kinetic energy harvester, a triboelectric nanogenerator, or other suitable power supply) that can power at least some of the components of the garment system 100, such as the control electrical circuitry 114, the one or more activity sensors 108, or the one or more actuators 110.

As will be discussed in more detail below, instructions that the control electrical circuitry 114 of the control system 112 employs for directing and controlling the operation of the one or more activity sensors 108 and the one or more actuators 110 can be pre-programmed in the control electrical circuitry 114, or programmed by the subject 106 or other person such as a medical professional like a doctor, a nurse, a physical therapist, a trainer, etc. For example, the programming of the control electrical circuitry 114 can be affected via at least one of software, firmware, programmable logical devices, or other technique for controlling the one or more activity sensors 108 and the one or more actuators 110 or other components of the garment system 100 in a selected manner.

During use in some operational situations, responsive to the one or more activity sensors 108 sensing the at least one characteristic of the at least one muscle or the at least one joint of the at least body part 104 that is related to muscle activity or joint activity thereof, the control electrical circuitry 114 directs the one or more actuators 110 to selectively compress against the at least one body part 104 to provide more support thereto or to improve muscle or joint functioning, such as increased blood flow or increased oxygenation to the at least one muscle or at least one joint of the at least one body part 104. For example, responsive to the one or more activity sensors 108 sensing the at least one characteristic of the at least one muscle or the at least one joint of the at least body part 104 that is related to muscle activity or joint activity thereof is over a threshold level, the control electrical circuitry 114 directs the one or more actuators 110 to selectively compress against the at least one body part 104. For example, the compression applied by the one or more actuators can be a gradient of compression along the at least one body part 104. In a more specific embodiment, the control electrical circuitry 114 can direct the one or more actuators 110 to cause the flexible compression garment 102 to selectively compress against at least one first portion of the at least one muscle of the at least one body part 104 with a first level of compression and selectively compress against at least one second portion of the at least one muscle or a second muscle of the at least one body part 104 with a second level of compression that is different than the first level of compression. As another example, the compression applied by the one or more actuators 110 can be one or more compression pulses applied to the at least one body part 104.

During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 directs the one or more actuators 110 to selectively relieve compression against the at least one body part 104, such as during a portion of an athletic activity in which the at least one muscle or the at least one joint of subject is minimally exerted or stressed, respectively. For example, responsive to the one or more activity sensors 108 sensing the at least one characteristic of the at least one muscle or the at least one joint of the at least body part 104 that is related to muscle activity or joint activity thereof is below a threshold level, the control electrical circuitry 114 directs the one or more actuators 110 to selectively relieve compression against the at least one body part 104.

In an embodiment, the garment system 100 can also be operated according to a feedback loop. For example, the control electrical circuitry 114 can direct the one or more actuators 110 to selectively compress or selectively relieve compression against the at least one body part 104 a first selected amount, followed by selectively compress or selectively relieve compression against the at least one body part 104 a second selected amount that is different than the first amount.

Although only one flexible compression garment 102 is shown in FIG. 1, in other embodiments, a plurality of flexible compression garments 102 can be worn on different body parts of the subject 106. In such an embodiment, each of the plurality of flexible compression garments 102 includes its own one or more activity sensors and one or more actuators that can be individually operably coupled to the control system 112 and independently operate according to directions from the control system 112.

As mentioned above, the one or more activity sensors 108 can be configured to sense at least one characteristic of the at least one muscle or the at least one joint of the at least body part 104. For example, the at least one characteristic can be at least one physical characteristic, at least one chemical characteristic (e.g., biochemical or biological), or at least one physiological characteristic of the at least one muscle or the at least one joint of the at least body part 104. More specifically, for example, the at least one characteristic can include at least one of nerve activity of the at least one muscle of the at least one body part 104, temperature of the at least one muscle or the at least one joint of the at least one body part 104, oxygenation of the at least one muscle or the at least one joint of the at least one body part 104, acoustic emission from the at least one muscle or the at least one joint of the at least one body part 104, or other suitable characteristic that can be correlated to muscle or joint activity. In an embodiment, the one or more activity sensors 108 are configured to only sense the at least one characteristic of the at least one muscle of the at least one body part 104, while in other embodiments, the one or more activity sensors 108 are configured to only sense the at least one characteristic of the at least one joint of the at least one body part 104.

In order to sense the at least one characteristic of the at least one muscle or the at least one joint, various different activity sensors can be used. For example, in any of the embodiments disclosed herein, the one or more activity sensors 108 can include at least one of an electromyography sensor, a thermal sensor, a muscle oxygenation sensor, an acoustic sensor, a chemical sensor, a biochemical sensor, or a biosensor. The one or more activity sensors 108 can be disposed at least partially on an interior surface of the flexible compression garment 102 defining an interior space that receives the at least one body part 104, or at least partially embedded in the flexible compression garment 102.

In an embodiment, the one or more activity sensors 108 are configured to sense onset of or a threshold level of muscle activity of the at least one muscle of the at least one body part 104. In such an embodiment, the control electrical circuitry 114 is configured to direct the one or more actuators 110 to selectively compress against the at least one body part 104 responsive to the one or more activity sensors 108 sensing the onset of muscle activity but prior to the muscle activity occurring. One suitable activity sensor configured to sense nerve impulses of the at least one muscle indicative of the onset of the muscle activity includes one or more electromyography sensors, which can be attached, adhered, or embedded within the flexible compression garment 102 or attached directly to the subject 106. For example, responsive to sensing the onset of muscle activity via the one or more electromyography sensors, the control electrical circuitry 114 can direct the one or more actuators 110 to cause the flexible compression garment 102 to selectively compress the at least one muscle or the at least one joint of the at least one body part 104. Examples of suitable electromyography sensors that can be used to practice one or more embodiments disclosed herein are disclosed in U.S. Patent Application Publication Nos. 20060058694 and 20130041235, and in Kim, et al., Science 333, 838-843 (2011), the disclosure of each of which is incorporated herein, in its entirety, by this reference.

In an embodiment, the one or more activity sensors 108 can include one or more passive infrared thermal sensors. For example, each passive infrared thermal sensor is positioned on or in the flexible compression garment 102 and configured to sense infrared radiation from the at least one muscle of the at least one body part 104. An increase in the infrared radiation can be indicative of or correlated with increased muscle temperature, which can be indicative of increased muscle activity. A decrease in the infrared radiation can be indicative of or correlated with decreased muscle temperature, which can be indicative of decreased muscle activity. For example, responsive to sensing an increase in or a threshold level of infrared radiation, the control electrical circuitry 114 may direct the one or more actuators 110 to cause the flexible compression garment 102 to selectively compress the at least one muscle or the at least one joint of the at least one body part 104. As another example, responsive to sensing a decrease in or less than a threshold level of infrared radiation, the control electrical circuitry 114 can direct the one or more actuators 110 to cause the flexible compression garment 102 to selectively relieve compression against the at least one muscle or the at least one joint of the at least one body part 104 due to muscle activity decreasing.

When the one or more activity sensors 108 are configured to sense temperature of the at least one muscle directly or indirectly, in an embodiment, the flexible compression garment 102 can include one or more fluid channels through which coolant can flow, a fluid coolant reservoir, and a pump configured to pump the fluid coolant from the reservoir through the one or more fluid channels. Thus, in such an embodiment, the control electrical circuitry 114 can direct the pump to pump fluid coolant from the fluid coolant reservoir through the one or more fluid channels to help cool the at least one muscle.

In an embodiment, the one more activity sensors 108 can include one or more muscle oxygenation sensors. For example, each muscle oxygenation sensor can include a near infrared sensor positioned and configured to deliver light in the near infrared spectrum to the at least one muscle of the at least one body part 104 and detect light reflected from the at least one muscle (e.g., tissue), thereby sensing absorption of the near infrared light by the muscle that differs in oxygenated and deoxygenated tissues. Examples of near infrared sensors for measuring the oxygenation of muscle tissues that can be used to practice one or more embodiments disclosed herein are disclosed in Hamaoka, et al., Phil. Trans. R. Soc. A (2011) 369, 4591-4604, which is incorporated herein, in its entirety, by reference. Changes in the absorption of near infrared light from the at least one muscle can be correlated with or can be indicative of increased muscle oxygenation. For example, changes in the absorption of the near infrared light can be associated with increased exertion or decreased muscle oxygenation (e.g., associated with overwork, cramping, or claudication).

In an embodiment, responsive to sensing a change in muscle oxygenation, the control electrical circuitry 114 can direct the one or more actuators 110 to cause the flexible compression garment 102 to selectively compress or selectively relieve compression against the at least one muscle or at least one joint of the at least one body part 104. For example, responsive to sensing an increase in muscle oxygenation over a threshold level, the control electrical circuitry 114 can direct the one or more actuators 110 to cause the flexible compression garment 102 to selectively compress the at least one muscle or at least one joint of the at least one body part 104. For example, responsive to sensing a decrease in muscle oxygenation below a threshold level, the control electrical circuitry 114 can direct the one or more actuators 110 to cause the flexible compression garment 102 to selectively relieve compression against the at least one muscle or the at least one joint of the at least one body part 104 due to muscle activity decreasing. In other embodiments, the one or more oxygenation sensors can be used to sense a change in joint oxygenation.

In an embodiment, the one or more activity sensors 108 can include multiple near infrared source-detector pairs that can measure spatial and regional differences in skeletal muscle oxygenation and/or localized changes of the at least one body part 104. For example, responsive to sensing a localized decrease in infrared radiation below a threshold level indicative of significantly decreased muscle oxygenation and blood flow associated with a muscle cramp, the control electrical circuitry 114 can direct the one or more actuators 110 to cause the flexible compression garment 102 to selectively compress against the at least one muscle of the at least one body part 104 to provide localized support and increase blood pressure. For example, responsive to sensing a varied decrease in infrared radiation indicative of a gradient of decreased muscle oxygenation and blood flow associated with muscle overexertion, the control electrical circuitry 114 can direct the one or more actuators 110 to cause the flexible compression garment 102 to selectively compress against at least one first portion of the at least one muscle of the at least one body part 104 with a first level of compression and selectively compress against at least one second portion of the at least one muscle or a second muscle of the at least one body part 104 with a second level of compression or to cause the flexible compression garment 102 to intermittently selectively compress against a part of the at least one muscle of the at least one body part 104 to provide localized to increase blood flow to the muscle.

In an embodiment, the one or more activity sensors 108 can include one or more acoustic transducers configured to irradiate the at least one muscle or the at least one joint of the at least one body part 104 with acoustic radiation (e.g., acoustic wave(s)) and receive reflected acoustic radiation responsive thereto. The received reflected acoustic radiation can be correlated with or can be indicative of muscle activity or joint activity of the at least one muscle or the at least one joint of the at least one body part 104. For example, a relatively stronger/more intense reflected acoustic radiation received by the one or more acoustic transducers can be indicative of relatively tenser, more active muscles, while a relatively weaker/less intense reflected acoustic radiation received by the one or more acoustic transducers can be indicative of relatively looser, less active muscles.

In an embodiment, the acoustic transducer includes an ultrasound transducer, and each of the acoustic radiation and the reflected acoustic radiation includes ultrasound radiation (e.g., ultrasonic wave(s)). The received reflected ultrasound radiation can be correlated with or can be indicative of at least one characteristic of a muscle activity or a joint activity of the at least one body part 104. For example, altered echogenicity detected by the one or more acoustic transducers can be indicative of swelling or inflammation of the at least one muscle. For example, altered echogenicity detected by the one or more acoustic transducers can be indicative of joint effusion of the at least one joint. For example, Doppler ultrasound sensing of the at least one muscle can detect increased blood flow within the at least one muscle, indicating increased activity of the at least one muscle. For example, Doppler ultrasound sensing of a ligament or tendon may detect limited activity within the ligament or tendon, indicating stress to the region. In an embodiment, responsive to the one or more acoustic transducers detecting a change in at least one characteristic of the at least one muscle or the at least one joint of the at least one body part 104, the control electrical circuitry 114 can direct the one or more actuators 110 to cause the flexible compression garment 102 to selectively compress or selectively relieve compression against the at least one muscle or at least one joint. For example, responsive to sensing echogenicity indicating an increase in muscle or joint activity, the control electrical circuitry 114 can direct the one or more actuators 110 to cause the flexible compression garment 102 to selectively compress the at least one muscle or at least one joint of the at least one body part 104. For example, responsive to sensing echogenicity indicating a decrease in muscle or joint activity, the control electrical circuitry 114 can direct the one or more actuators 110 to cause the flexible compression garment 102 to selectively relieve compression against the at least one muscle or at least one joint of the at least one body part 104 due to muscle activity decreasing. For example, responsive to sensing echogenicity indicating inflammation in the least one muscle or the at least one joint, the control electrical circuitry 114 can direct the one or more actuators 110 to cause the flexible compression garment 102 to selectively compress, and thereby support, the at least one muscle or at least one joint of the at least one body part 104.

In an embodiment, the one more activity sensors 108 can include one or more acoustic myography sensors positioned and configured to sense acoustic emission from the at least one muscle of the at least one body part 104. An example of an acoustic myography sensor for sensing muscle use suitable for practicing one or more embodiments disclosed herein is disclosed in Harrison, et al., Physiol Rep, 1(2): e00029; 2013, the disclosure of which is incorporated herein, in its entirety, by this reference. For example, responsive to sensing a high frequency by the acoustic myography sensor, indicative of increased muscle use, the control electrical circuitry 114 may direct the one or more actuators 110 to cause the flexible compression garment 102 to selectively compress the at least one muscle of the at least one body part 104.

In an embodiment, the one more activity sensors 108 can include one or more acoustic sensors positioned and configured to sense acoustic emissions from one or more body parts such as at least one joint of the at least one body part 104. For example, the one or more acoustic sensors can include passive acoustic sensors positioned adjacent to or proximate to the at least one joint (e.g., an elbow as illustrated in FIG. 1, wrist, or knee) so that the one or more passive acoustic sensors can receive/detect acoustic emissions from the at least one joint. Such emissions can be indicative of joint problems, such as aggravation of an arthritic or an osteoarthritic condition and resultant arthralgia. For example, responsive to sensing acoustic emission or an increase in acoustic emission from the at least one joint, the control electrical circuitry 114 may direct the one or more actuators 110 to cause the flexible compression garment 102 to selectively compress the at least one joint and the at least one muscle around the at least one joint of the at least one body part 104 to thereby alleviate arthralgia.

In an embodiment, the one more activity sensors 108 can include one or more of at least one chemical sensor, at least one biochemical sensor, or at least one biosensor configured to detect an analyte from the at least one muscle or the at least one joint of the at least one body part 104. For example, at least one chemical sensor, at least one biochemical sensor, or at least one biosensor can be configured to detect at least one of an ion, a salt, glucose, a lactate, lactic acid, or an inflammatory molecule from the at least one muscle or the at least one joint. For example, responsive to sensing an increase in lactic acid in the at least one muscle by a biosensor indicative of muscle fatigue, the control electrical circuitry 114 can direct the one or more actuators 110 to cause the flexible compression garment 102 to selectively compress the at least one muscle of the at least one body part 104.

In an embodiment, one more optional additional types of activity sensors 108' can be incorporated into the flexible compression garment 102 and operably coupled to the control electrical circuitry 114. For example, the one or more additional types of activity sensors can include one or more low profile heart rate sensors that are configured to sense a heart rate of the subject 106. In an embodiment, the one or more heart rate sensors can include an electrocardiography sensor or a pulse sensor (e.g., a pulse oximetry sensor). In an embodiment, the one or more heart rate sensors can include a pulse sensor for measuring a peripheral pulse, such as in a limb. Thus, in an embodiment, the pulse sensor can be selectively positioned on the flexible compression garment 102 to be proximate to an artery, such as a relatively large artery on the at least one body part 104 of the subject 106. Examples of low profile, stretchable and flexible heart rate and electrocardiography sensors are described in U.S. Patent Application Publication Nos. 20060058694 and 20130041235, previously incorporated by reference.

Responsive to sensing an increase in the heart rate of the subject 106 indicative of increased muscle activity, the control electrical circuitry 114 can direct the one or more actuators 110 to cause the flexible compression garment 102 to selectively compress the at least one muscle or at least one joint of the at least one body part 104. As another example, responsive to sensing a decrease in the heart rate of the subject 106 indicative of decreased muscle activity, the control electrical circuitry 114 can direct the one or more actuators 110 to cause the flexible compression garment 102 to selectively relieve compression against the at least one muscle or at least one joint of the at least one body part 104 due to muscle activity decreasing.

By way of another example and having applicability to any of the activity sensors 108 or optional additional types of activity sensors 108' disclosed herein, in an embodiment, actuating the one or more actuators 110 to cause the flexible compression garment 102 to selectively compress against the at least one body part 104 is responsive to the at least one characteristic sensed by one or more activity sensors being indicative of the at least one muscle being injured or being strained past a strain limit. In another embodiment having applicability to any of the activity sensors 108 disclosed herein, actuating the one or more actuators 110 to cause the flexible compression garment 102 to selectively compress against or selectively relieve compression against the at least one body part 104 is responsive to the at least one characteristic sensed by one or more activity sensors 108 being indicative of the at least one muscle being exerted. In another embodiment having applicability to any of the one or more activity sensors 108 disclosed herein, actuating the one or more actuators 110 to cause the flexible compression garment 102 to selectively compress against or selectively relieve compression against the at least one body part 104 can be responsive to the at least one characteristic sensed by the one or more activity sensors 108 being indicative of the at least one muscle being not exerted beyond a threshold. For example, the one or more activity sensors 108 can indicate that the at least one muscle is not being exerted at or near a physiological or functional limit thereof, and the flexible compression garment 102 adjusts the amount of compression applied to the at least one muscle to cause the muscle work harder, such as during strength training.

The one or more actuators 110 can be selected from a number of suitable different types of actuators. Additionally, as will be discussed in more detail below, the one or more actuators 110 may be positioned in a number of different configurations. For example, in any of the embodiments disclosed herein, the one or more actuators 110 can include at least one of one or more electroactive polymer actuators, one or more electroactive metallic actuators, one or more motors, or one or more hydraulic actuators.

In an embodiment, the one or more electroactive polymer actuators include one or more actuator elements at least partially formed from ferroelectric polymers, dielectric elastomers, or electrostrictive graft elastomers. Responsive to a voltage applied by the power supply 118 based on instructions from the control electrical circuitry 114, the electroactive polymer actuators may increase or decrease in length, diameter, or other dimension depending on the polarity of the applied voltage to cause the flexible compression garment 102 to selectively compress or relieve compression of the at least one body part 104. For example, suitable electroactive polymers for the electroactive polymer actuators include at least one of NuSil CF19-2186 commercially available from NuSil Technology of Carpinteria, Calif., silicone elastomers, acrylic elastomers (e.g., VHB 4910 acrylic elastomer commercially available from 3M Corporation of St. Paul, Minn.), polyurethanes, thermoplastic elastomers, copolymers comprising polyvinylidene difluoride ("PVDF"), pressure-sensitive adhesives, fluoroelastomers, polymers comprising silicone and acrylic moieties, or other suitable electroactive polymers.

In an embodiment, the one or more electroactive metallic actuators include one or more actuator elements at least partially formed from a shape memory material. For example, the shape memory material can include a nickel-titanium shape memory alloy, such as nitinol or other suitable nickel-titanium alloy composition. Responsive to the power supply 118 passing a current through the shape memory material to heat the shape memory material based on instructions from the control electrical circuitry 114, the electroactive metallic actuators may increase or decrease in length, diameter, or other dimension depending on the temperature to which the shape memory material is heated to cause the flexible compression garment 102 to selectively compress or relieve compression of the at least one body part 104.

Examples of such nickel-titanium shape memory alloys are currently commercially available from Dynalloy, Inc. and sold under the trade name Flexinol®. Flexinol HT® has a transition temperature of about 194° F., with an activation start temperature at about 190° F. and an activation finish temperature at about 208° F. Such nickel-titanium alloys can gradually and controllably contract in length about 2% to about 5% of their length or other dimension as they are heated from the activation start temperature to the activation finish temperature.

In an embodiment, the one or more motors include one or more micro-electro-mechanical actuators. For example, the one or more micro-electro-mechanical motors can include one or more micro-piezoelectric actuators, one or more micro-electrostatic actuators, or one or more micro-electromagnetic actuators. Examples of suitable micro-electromechanical motors that can be used to practice one or more embodiments disclosed herein are disclosed in Acoust. Sci. & Tech. 31, 2 (2010), the disclosure of which is incorporated herein, in its entirety, by this reference. As another example, one suitable micro-piezoelectric actuator is New Scale's SQUIGGLE™ motor.

Figure 2A:
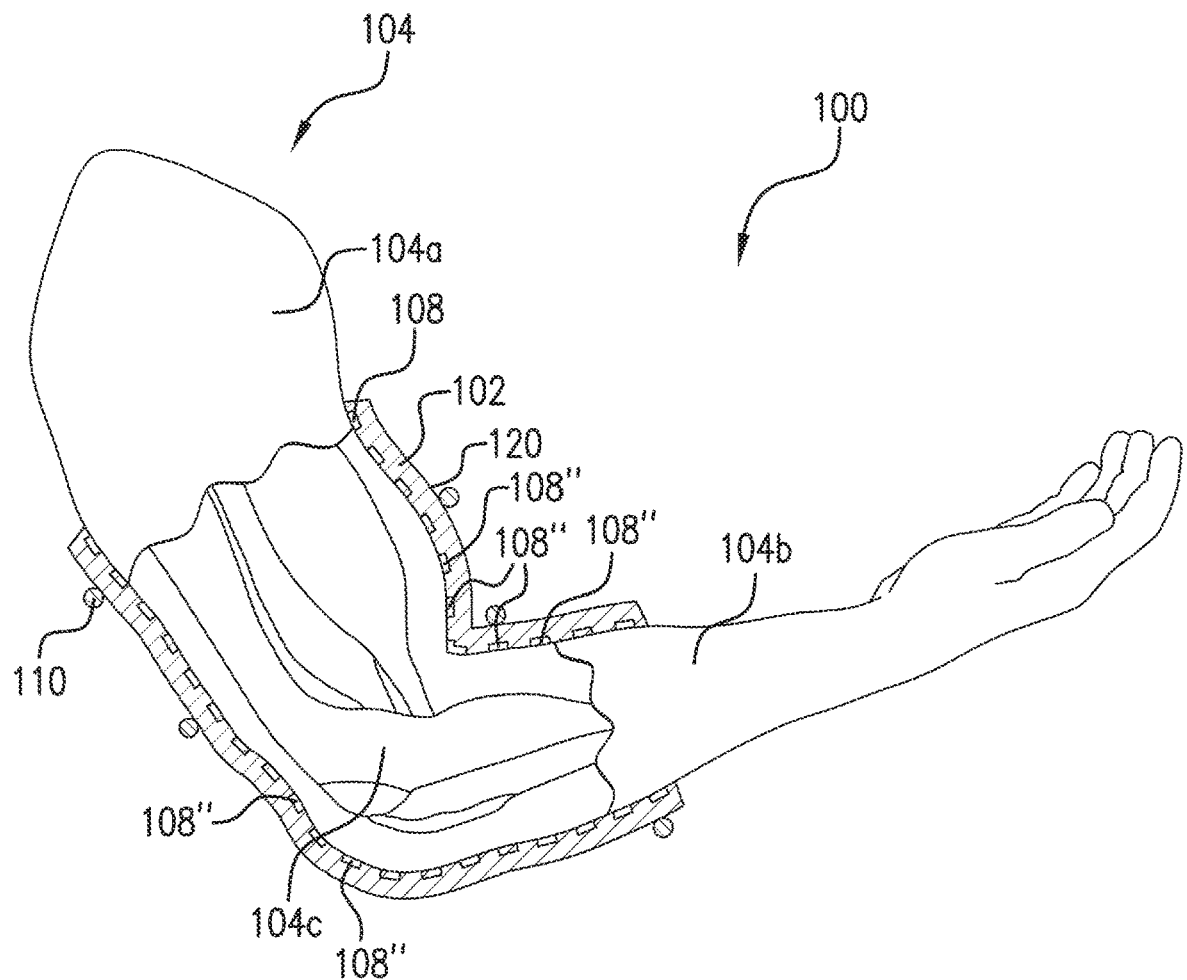
FIG. 2A is an isometric cutaway view of a flexible compression garment worn on an arm of a subject of the garment system shown in FIG. 1, according to an embodiment.
Figure 2B:
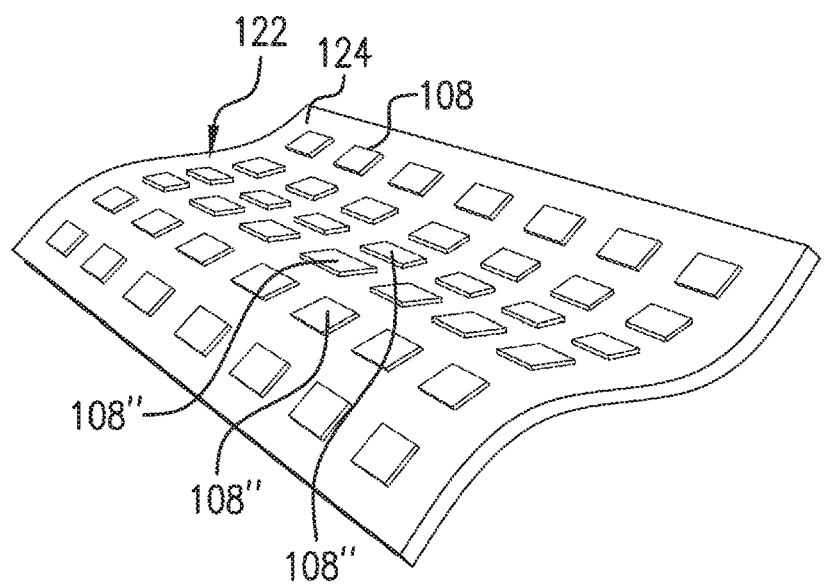
FIG. 2B is an isometric cutaway view of a section of the flexible compression garment shown in FIG. 2A, without the flexible compression garment shown being worn an arm of a subject, according to an embodiment.

FIGS. 2A and 2B are isometric cutaway views of an embodiment of the flexible compression garment 102 of the garment system shown in FIG. 1, which is worn on the at least one body part 104 of the subject 106, according to an embodiment. In the illustrated embodiment shown in FIGS. 2A and 2B, the at least one body part 104 is an arm of the subject, which includes an upper arm 104a, a forearm 104b, and an elbow joint 104c connecting the upper arm 104a and the forearm 104b together. The flexible compression garment 102 defines an exterior 120, and the one or more actuators 110 are configured as a single coiled actuator extending about a portion of the exterior 120 of the flexible compression garment 102. For example, the single coiled actuator can extend circumferentially along the exterior 120 of the flexible compression garment 102 in a substantially helical path and is positioned and configured to increase or decrease an interior space 122 (FIG. 2B) defined by an interior surface 124 (FIG. 2B) of the flexible compression garment 102 responsive to actuation thereof. However, in other embodiments, the one or more actuators 110 such as the single coiled actuator can be embedded internally within the flexible compression garment 102.

Referring to FIG. 2B, in the illustrated embodiment, the activity sensors 108 may be positioned on or at least partially embedded within the interior surface 124 of the flexible compression garment 102. For example, when at least some of the activity sensors 108 are configured as acoustic sensors for sensing acoustic emission from the elbow joint 104c, such activity sensors 108 can be positioned on or in the interior surface 124 of the flexible compression garment 102 so that they are located at or near the elbow joint 104c (or other joint, such as one that can be affected by arthritis) and labeled as activity sensors 108" in FIGS. 2A and 2B as merely an example.

Figure 2C:
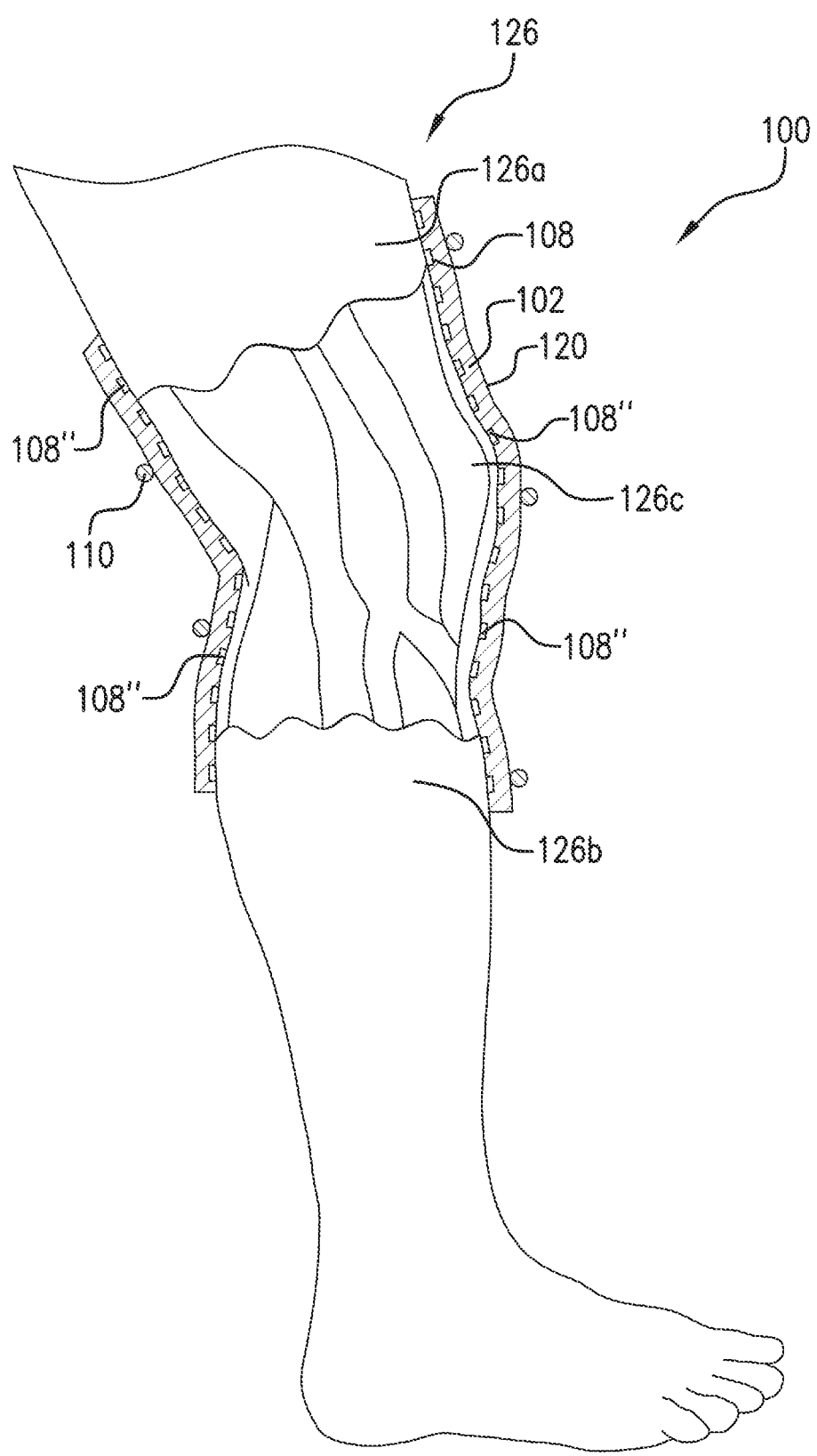
FIG. 2C is an isometric cutaway view of an embodiment of a flexible compression garment worn on a leg of a subject, according to an embodiment.
Figure 2D:
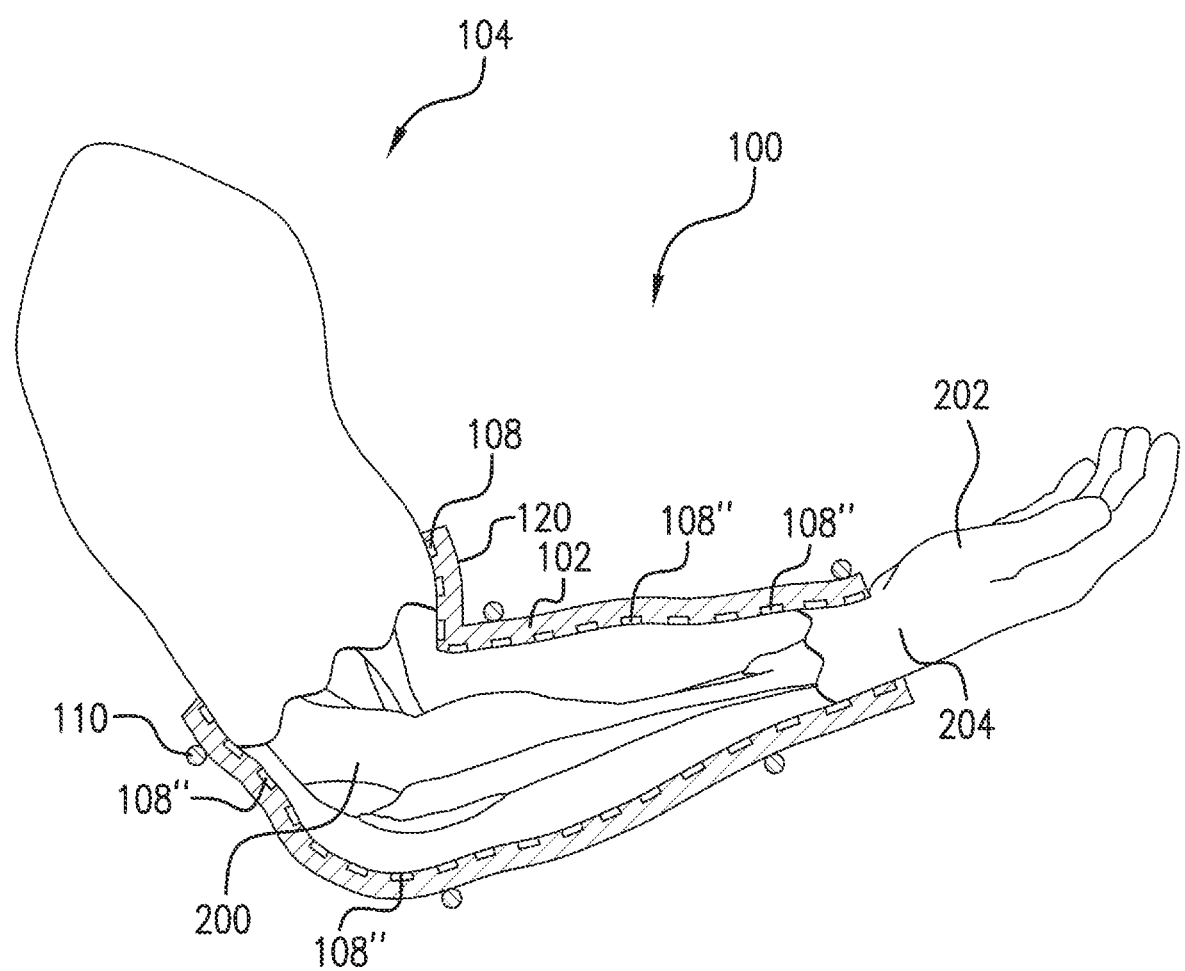
FIG. 2D is an isometric cutaway view of an embodiment of a flexible compression garment worn on a forearm and hand of a subject, according to an embodiment.

As previously discussed, the garment systems disclosed herein can be used on a number of different body parts besides an arm. For example, the at least one body part 104 can include a portion of a thigh, a portion of a lower leg, a portion of a hand, a portion of a foot, or a portion of a neck. FIG. 2C is an isometric cutaway view of an embodiment of the flexible compression garment 102 worn on a leg 126 of the subject 106. The flexible compression garment 102 can be configured to extend around a thigh 126a, a lower leg 126b, and a knee 126c that connects the thigh 126a and lower leg 126b together. As another example, FIG. 2D is an isometric cutaway view of an embodiment of the flexible compression garment 102 configured to be worn on a forearm 200, hand 202, and wrist 204 of the subject 106. Of course, in other embodiments, the flexible compression garment 102 can be configured for other body parts, such as the upper arm and shoulder, or neck of the subject 106. In other embodiments, the flexible compression garment 102 can be configured for other body parts that do not include a joint, such as a portion of a limb including, but not limited to, all or part of a thigh, a calf, a forearm, or an upper arm of the subject 106.

Figure 3A:
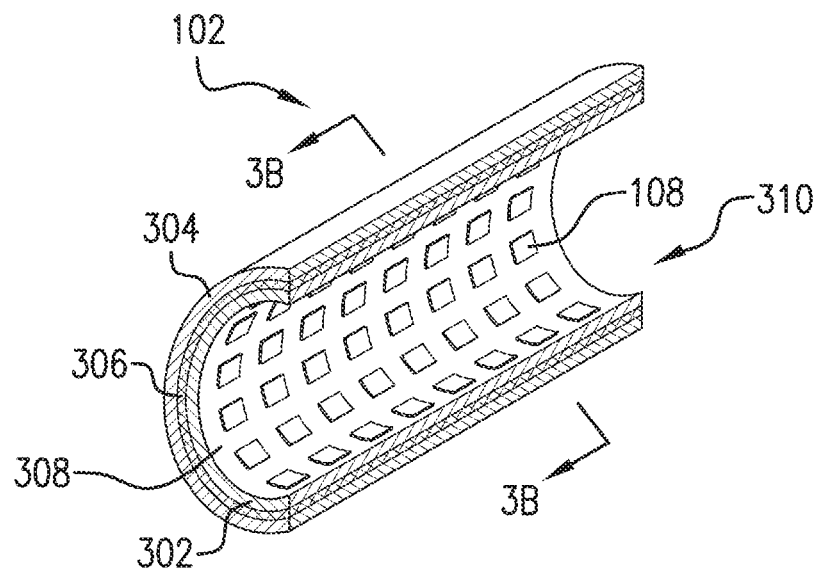
FIG. 3A is an isometric cutaway view of the flexible compression garment shown in FIG. 1, according to an embodiment.
Figure 3B:
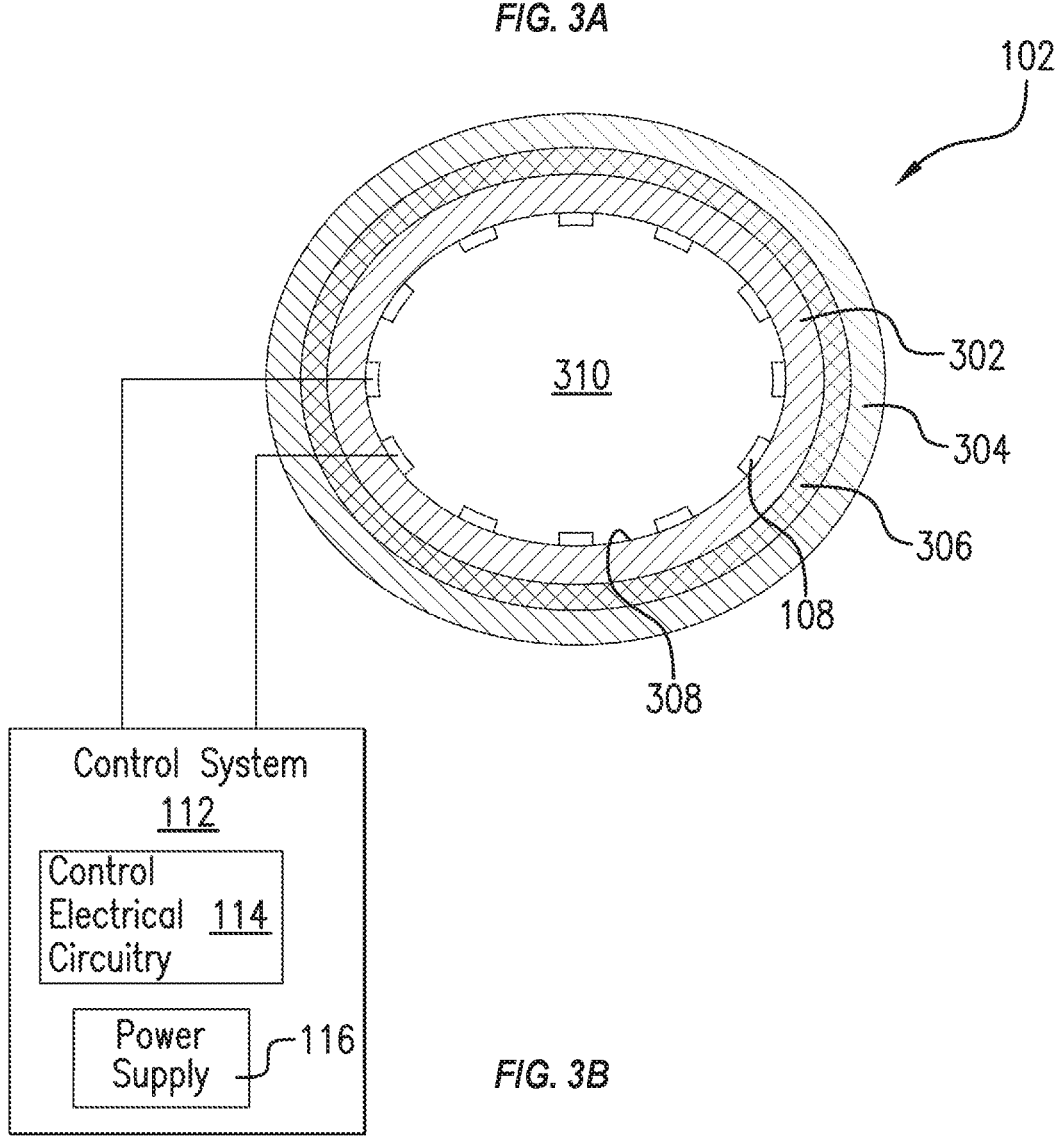
FIG. 3B is a cross-sectional view of the flexible compression garment shown in FIG. 3A taken along line 3B-3B thereof, according to an embodiment.

FIGS. 3A and 3B are isometric cutaway and cross-sectional views of the flexible compression garment 102 shown in FIG. 1, according to an embodiment. In the illustrated embodiment, the flexible compression garment 102 includes an inner garment body 302, an outer garment body 304, and a substantially tubular actuator 306 disposed between the inner garment body 302 and the outer garment body 304 in a concentric arrangement. For example, the substantially tubular actuator 306 is illustrated as being embedded within the flexible compression garment 102 and held between the inner garment body 302 and the outer garment body 304. As merely an example, the substantially tubular actuator 306 can be made from an electroactive polymer or a tube of shape memory alloy that is responsive to an appropriate actuation stimulus from the power supply 118 of the control system 112 so that a volume of an inner space 310 defined by the inner garment body 302 can increase or decrease responsive to actuation of the substantially tubular actuator 306.

In the illustrated embodiment, the one or more activity sensors 108 are disposed on an interior surface 308 of the inner garment body 302 that defines the interior space 310. However, in other embodiments, the one or more activity sensors 108 may be at least partially embedded within the inner garment body 302.

During use in some operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively compress against the at least one body part 104 to provide more support thereto or to improve muscle or joint functioning. During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively relieve compression against the at least one body part 104, such as during a portion of an athletic activity in which the at least one muscle or the at least one joint of subject is minimally exerted or stressed, respectively. During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively compress against the at least one body part 104 or to selectively relieve compression against the at least one body part 104, such as to aid a particular action of the at least one muscle or the at least one joint. For example, the particular action can be an athletic action undertaken by at least one particular limb, such as an arm swinging a bat or club.

Figure 3C:
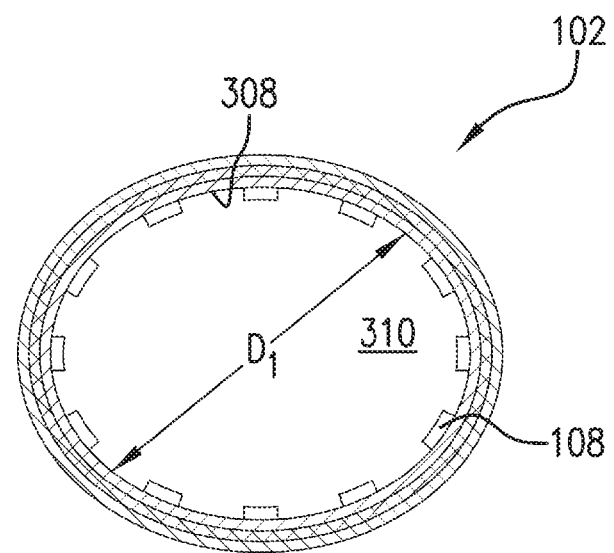
FIG. 3C is a cross-sectional view of the flexible compression garment shown in FIG. 3A prior to actuation of one or more actuators or at a low actuation level, according to an embodiment.
Figure 3D:
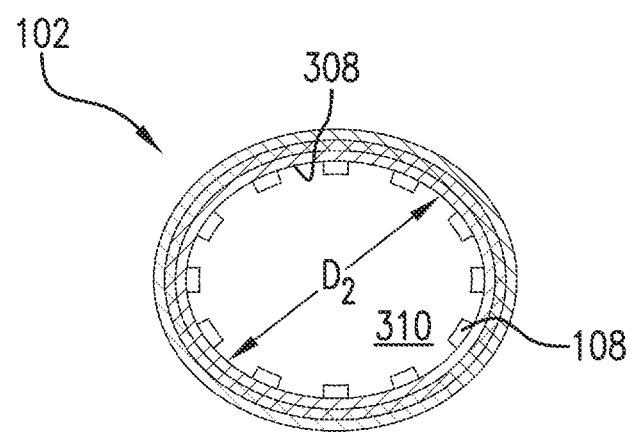
FIG. 3D is a cross-sectional view of the flexible compression garment shown in FIG. 3A after actuation of one or more actuators or at a relatively higher actuation level than in FIG. 3C, according to an embodiment.

FIGS. 3C and 3D are cross-sectional views of the flexible compression garment 102 shown in FIG. 3A prior to actuation of the actuator 306 or at a low actuation level, and after actuation of the actuator 306 or at a relatively higher actuation level than in FIG. 3C, respectively. As shown in FIG. 3C, prior actuation of the actuator 306 or at a low actuation level, the interior space 310 of the flexible compression garment 102 exhibits a relatively larger diameter D1 or other lateral dimension. As shown in FIG. 3D, after actuation of the actuator 306 or at a relatively higher actuation level than in FIG. 3C, the actuator 306 selectively compresses the flexible compression garment 102 against at least one body part of the subject such that the interior space 310 of the flexible compression garment 102 exhibits a relatively smaller diameter D2 or other lateral dimension. This contraction of the flexible compression garment 102 can be used to apply selective amounts of compression forces to the at least one body part of the subject. For example, the actuator 306 can cause narrowing of substantially the entire flexible compression garment 102 to the smaller diameter D2.

Figure 4:
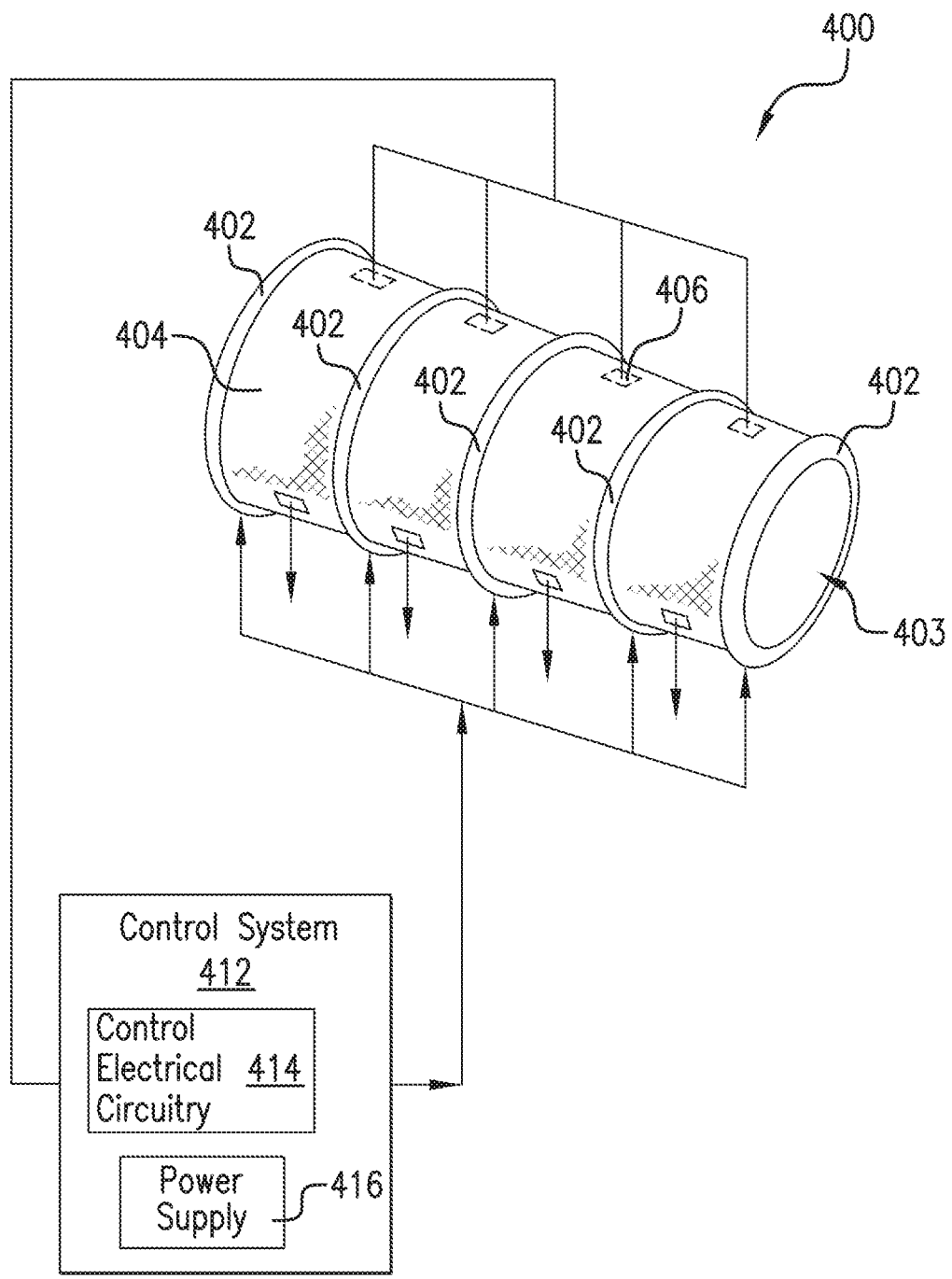
FIG. 4 is an isometric view of an embodiment of a garment system including a plurality of ring-shaped actuators, according to an embodiment.

FIG. 4 is an isometric view of an embodiment of a garment system 400 including a plurality of ring-shaped actuators 402. The garment system 400 includes a flexible compression garment 404 that can be made from the same materials as the flexible compression garment 102. The flexible compression garment 404 defines an interior space 403 for receiving at least one body part of a subject, such as an arm, leg, or other body part.

The plurality of ring-shaped actuators 402 are longitudinally spaced from each other. In the illustrated embodiment, the plurality of ring-shaped actuators 402 are disposed circumferentially about an exterior of the flexible compression garment 404. However, in other embodiments, the plurality of ring-shaped actuators 402 can be at least partially embedded within the flexible compression garment 404. As merely an example, each of the plurality of ring-shaped actuators 402 can be made from a ring electroactive polymer or a ring of shape memory alloy that is responsive to an appropriate actuation stimulus from a power supply 416 of a control system 412.

The garment system 400 further includes one or more activity sensors 406, which can be configured as any of the activity sensors disclosed herein. In the illustrated embodiment, the one or more activity sensors 406 are disposed within the interior space 403 of the flexible compression garment 404. However, in other embodiments, the one or more activity sensors 408 can be embedded within the flexible compression garment 404.

The control system 412 functions the same or similarly to the control system 112 in FIG. 1. For example, the control system 412 is operably coupled to the one or more activity sensors 408 and the plurality of ring-shaped actuators 402. Thus, during use in some operational situations, responsive to the one or more activity sensors 408 sensing the at least one characteristic of the at least one muscle or the at least one joint of the at least body part that is related to muscle activity or joint activity thereof, the control electrical circuitry 414 of the control system 412 directs the plurality of ring-shaped actuators 402 to selectively compress against the at least one body part to provide more support thereto or to improve muscle or joint functioning. Thus, the actuation of each of the plurality of ring-shaped actuators 402 decreases a diameter thereof. During use in other operational situations, responsive to the one or more activity sensors 408 sensing the at least one characteristic of the at least one muscle or the at least one joint of the at least body part that is related to muscle activity or joint activity thereof, the control electrical circuitry 414 of the control system 412 directs the plurality of ring-shaped actuators 402 to selectively relieve compression against the at least one body part, such as during a portion of an athletic activity in which the at least one muscle or at least one joint of a subject is minimally exerted or stressed, respectively. Thus, the actuation of each of the plurality of ring-shaped actuators 402 increases a diameter thereof.

Figure 5:
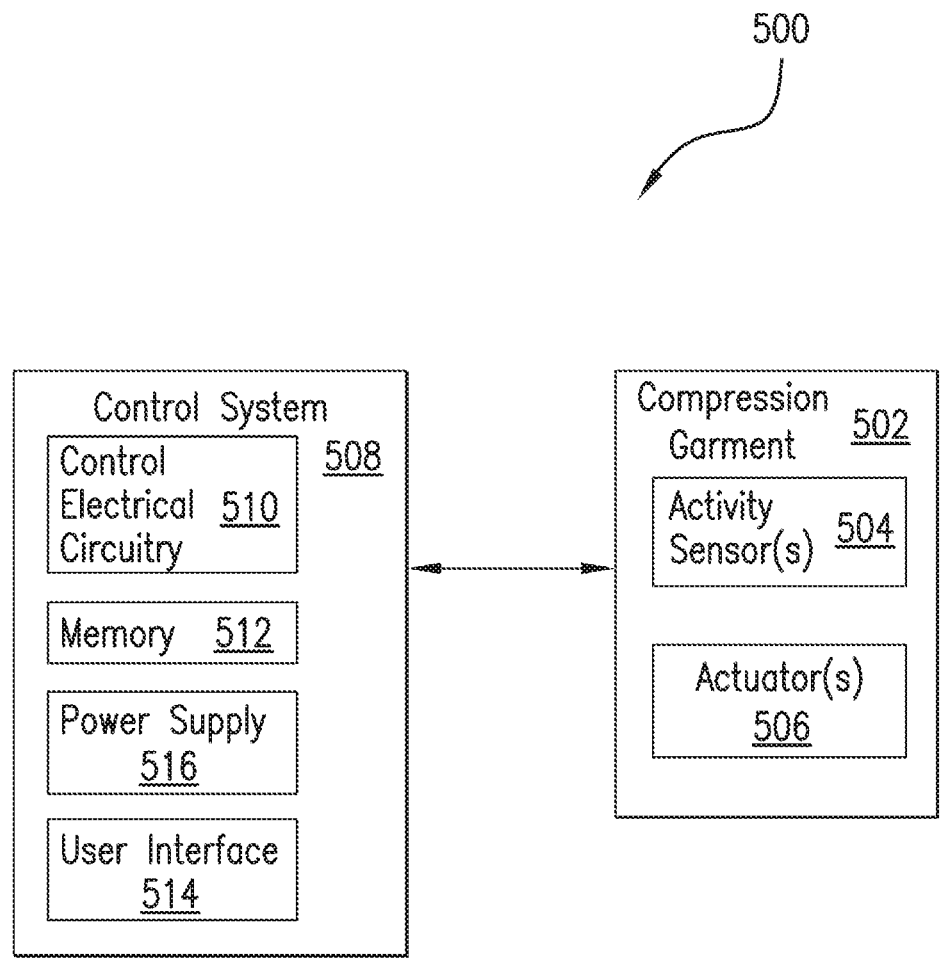
FIG. 5 is a functional block diagram of an embodiment of a garment system.

In some embodiments, the garment systems disclosed herein can include memory and a user interface that enables the subject or another person to program the manner in which the garment system operates. For example, FIG. 5 is a functional block diagram of an embodiment of a garment system 500. The garment system 500 includes a compression garment 502 including one or more activity sensors 504 and one or more actuators 506, as described in any of the embodiments disclosed herein. The garment system 500 further includes a control system 508 operably coupled to the one or more activity sensors 504 and the one or more actuators 506. The control system 508 includes control electrical circuitry 510 that controls the operation of the one or more activity sensors 504 or the one or more actuators 506, memory 512 operably coupled to the control electrical circuitry 510 that can be programmed with instructions via a user interface 514, and a power supply 516 that powers some or all of the components of the garment system 500.

The memory 512 can be programmed via the user interface 514 so that instructions for the operation of the garment system 500 are stored thereon. For example, the user interface 514 can include a keypad, monitor, touch screen, voice command recognition, desktop computer, laptop computer, cell phone, or combinations thereof that is operably coupled to the control electrical circuitry 510 of the control system 508. The user interface 514 can be operably coupled to the control electrical circuitry 510 via a wireless or wired communication connection. The subject that wears the garment system 500 or another party (e.g., a medical professional) can program instructions into the memory 512 for the operation of the one or more activity sensors 504 and the one or more actuators 506 via the user interface 514. Any method of operation for any of the garment systems disclosed herein can be programmed into the memory 512 with suitable instructions, as needed or desired. In an embodiment, the memory 512 is configured to store sensing data corresponding to the one or more sensing signals from the one or more activity sensors 504 and actuation data corresponding to the selective compression or the selective relief of compression of the flexible compression garment 502. Such sensing data and actuation data can be downloaded by the subject or other person (e.g., a medical professional) for analysis.

During operation, the control electrical circuitry 510 accesses and receives instructions from the memory 512 and directs the sensing operations of the one or more activity sensors 504 and actuation of the one or more actuators 506 at least partially based on instructions stored in the memory 512. For example, responsive to the instructions stored in the memory 512, the control system 508 can direct the one or more actuators 504 to cause the compression garment 502 to selectively compress against at least one part of the subject wearing the compression garment 502 responsive to the one or more activity sensors 504 sensing increased or sufficient muscle or joint activity of the subject. As another example, responsive to the instructions stored in the memory 512, the control system 508 can direct the one or more actuators 504 to cause the compression garment 502 to selectively relieve compression against the at least one part of the subject wearing the compression garment 502 responsive to the one or more activity sensors 504 sensing decreased or relatively low muscle or joint activity of the subject.

In an embodiment, the memory 512 stores sensing data corresponding to the one or more sensing signals from the one or more activity sensors 504 and stores actuation data corresponding to the selective compression or the selective relief of compression of the flexible compression garment 502, which can be downloaded by any of the user interfaces 514 disclosed herein (e.g., a cell phone, desktop computer, or laptop computer) or other computing device. For example, the user interface 514 can download the sensing data and the actuation data such as frequency and duration of compression and decompression of the at least one least body part via the flexible compression garment 502.

Figure 6:
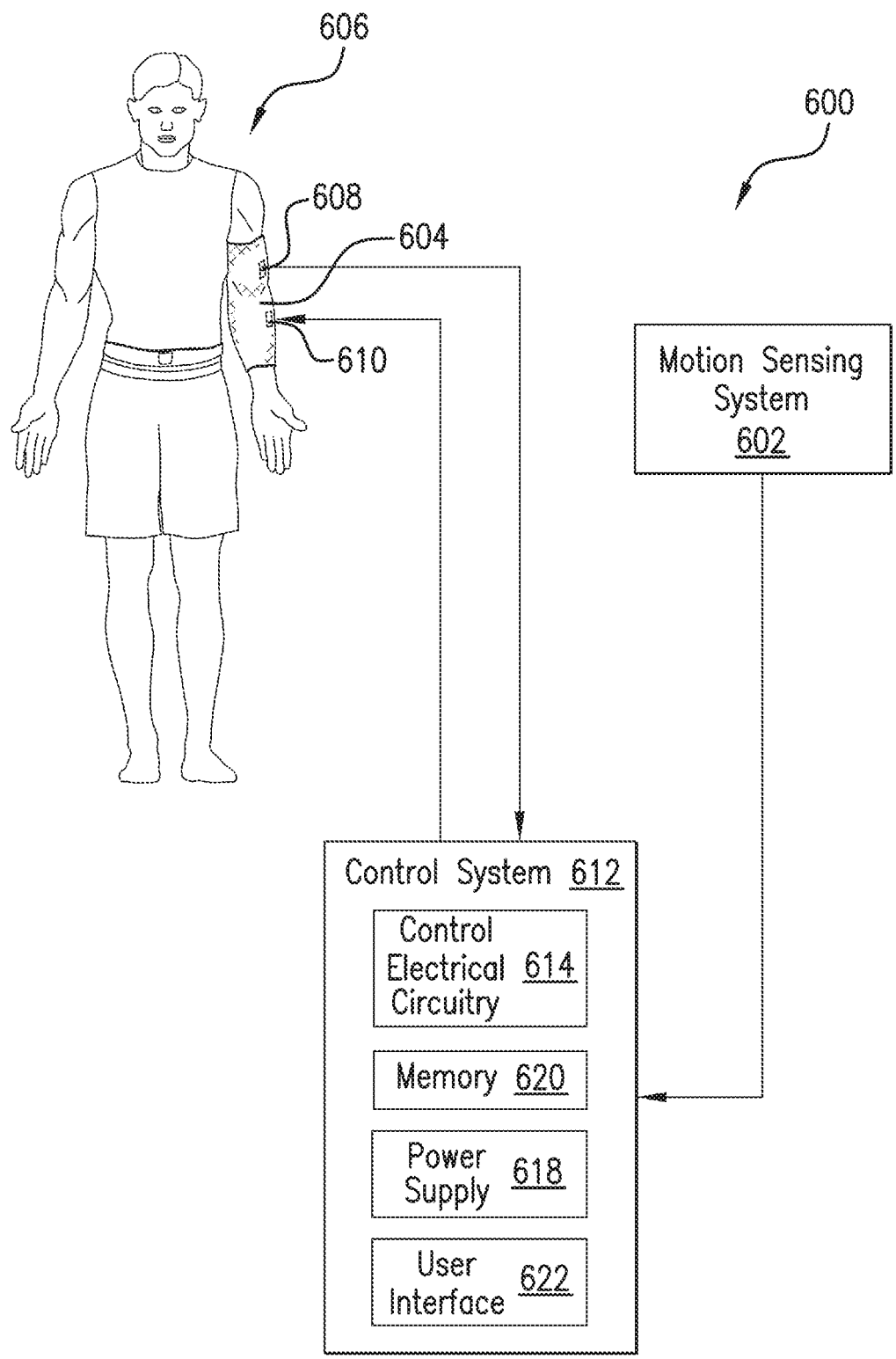
FIG. 6 is a functional block diagram of an embodiment of a garment system including a motion sensing system, according to an embodiment.

The garment systems disclosed herein can also be used in conjunction with a motion sensing system for teaching or correcting a subject's movement during different activities, such as walking, running, jumping, or specific sporting activities. FIG. 6 is a functional block diagram of an embodiment of a garment system 600 including a motion sensing system 602 and a compression garment 604 configured to be worn by a subject 606. For example, the motion sensing system 602 can be a Microsoft Kinect™ system or a machine vision sensing system that is configured to track physical movement of the subject 606, such as motion of one or more limbs of the subject. For example, such physical movement can be sporting activities, such as a baseball bat swing, golf swing, tennis racquet swing, or other type of activity, or general movement such as walking or arm motion for physical therapy. The compression garment 604 includes one or more activity sensors 608 and one or more actuators 610 shown schematically that can configured as any of the activity sensors and actuators disclosed herein.

The garment system 600 further includes a control system 612 having control electrical circuitry 614 configured to direct the one or more actuators 610 via one or more actuation signals 616 to cause the flexible compression garment 604 to selectively compress against or selectively relieve compression against at least one body part of the subject 606 responsive to receiving one or more sensing signals from the one or more activity sensors 608 and one or more motion signals 609 from the motion sensing system 602. The control system 612 further includes memory 620 operably coupled to the control electrical circuitry 614 that can be programmed with instructions via a user interface 622, and a power supply 618 (e.g., a battery or other suitable power supply) that can power at least some of the components of the garment system 600, such as the control electrical circuitry 614, the one or more activity sensors 608, or the one or more actuators 610.

The user interface 622 can include one or more of a screen or input device (e.g., keyboard, key pad, touchscreen, etc.) to receive input and communicate with a user of the garment system 600. The memory 620 can be programmed via the user interface 622 so that instructions for the operation of the garment system 600 are stored thereon. For example, the user interface 622 can include a keyboard, keypad, monitor, touch screen (e.g., touchpad), voice command recognition, a port, a clock, a disc drive, one or more buttons, one or more switches, or combinations thereof that are operably coupled to the control electrical circuitry 614 of the control system 612. The controller can be programmed with at least one operational program, one or more threshold levels, or entry of actuation commands via the user interface 622. For example, the subject that wears the garment system 600 or another party (e.g., a medical or athletic professional) can program instructions for the operation of the one or more activity sensors 608 or the one or more actuators 610 via the user interface 622.

In operation, responsive to receiving one or more sensing signals from the one or more activity sensors 608 and one or more motion signals 609 from the motion sensing system 602, the control electrical circuitry 614 of the control system 612 directs the one or more actuators 610 to cause the flexible compression garment 604 to selectively compress against or selectively relieve compression against the at least one body part of the subject 606. The selective compression or relief of compression is provided to direct the subject's 606 movement to correspond to a stored movement or movement pattern in the memory 620 of the control system 612. For example, the stored movement or movement pattern can be a model golf swing or other athletic movement as input via the user interface 622 by a golf professional or other athletic professional. The selective compression or relief of compression against the at least one body part (e.g., the subject's 606 arm) is provided to direct the subject's 606 movement to correspond to and substantially follow the movement or movement pattern stored in the memory 620. Thus, the garment system 600 can serve assist training the subject 606 in specific movements for sporting activities, or general movement such as walking for physical therapy. In another embodiment, responsive to receiving the input from the motion sensing system 602 via the one or more motion sensing signals 609, the memory 620 can be programmed with at least one operational program according to which the actuating the one or more actuators 610 occurs.

Figure 7:
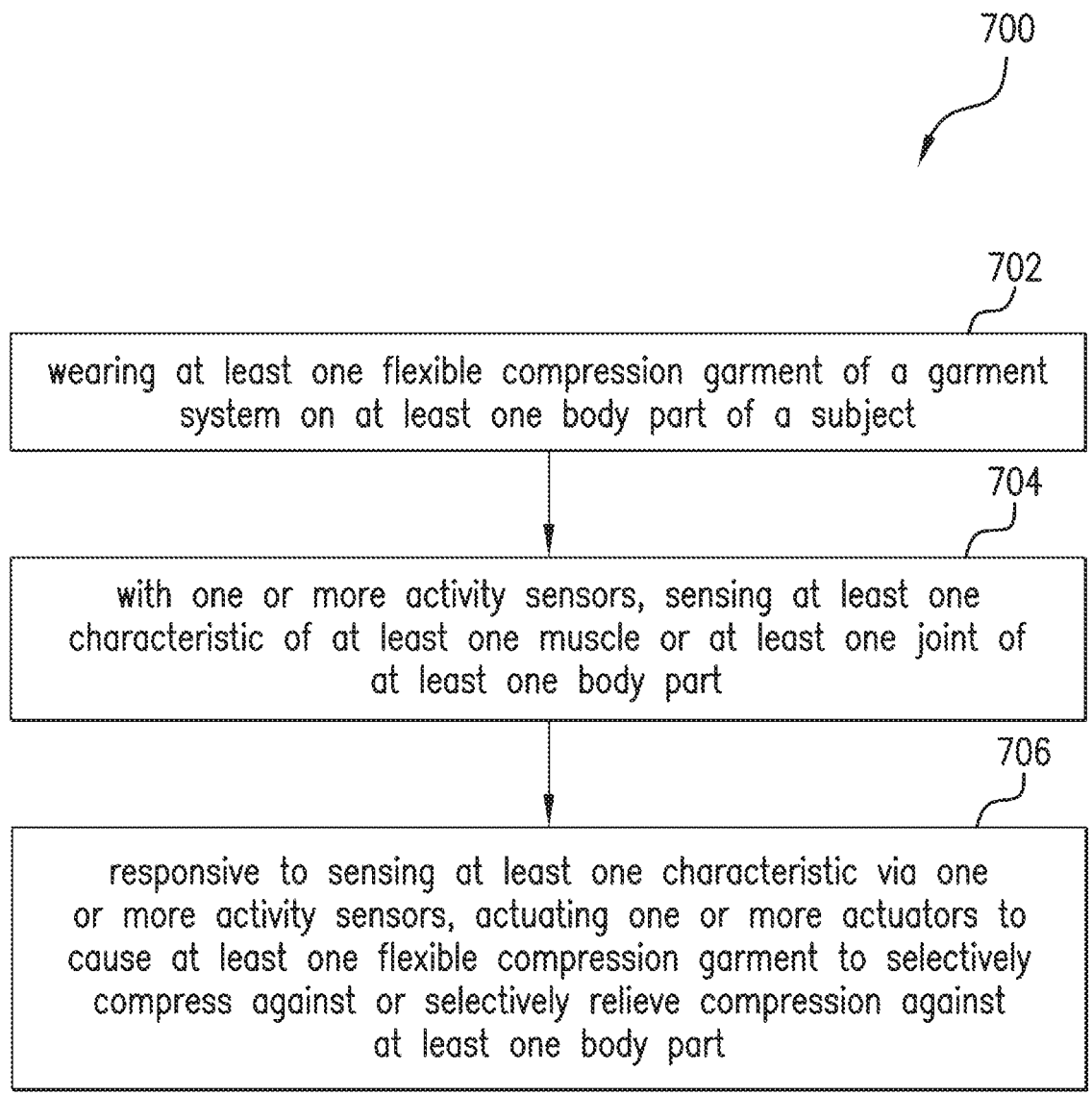
FIG. 7 is a flow diagram of an embodiment of a method of selectively compressing or relieving compression of at least one body part of a subject responsive to sensing feedback from one or more activity sensors, according to an embodiment.

FIG. 7 is a flow diagram of an embodiment of a method 700 of selectively compressing or relieving compression of at least one body part of a subject responsive to sensing feedback from one or more activity sensors. Instructions for any of the methods disclosed herein can be stored in memory of a garment system such as the memory 512 of the garment system 500.

The method 700 includes an act 702 of wearing at least one flexible compression garment of a garment system on at least one body part of a subject. For example, the at least one body part on which the at least flexible compression garment is worn includes at least a portion of an arm, at least a portion of a forearm, at least a portion of a wrist, at least a portion of a thigh, at least a portion of a lower leg, at least a portion of a neck, at least a portion of the head (including the jaw), or at least a portion of a chest. The garment system includes one or more activity sensors configured to sense at least one characteristic of at least one muscle or at least one joint of the at least body part that is related to muscle activity or joint activity thereof and one or more actuators configured to cause the at least one flexible compression garment to selectively compress against or selectively relieve compression against the at least one body part as disclosed in any of the garment systems disclosed herein, such as the garment system 100 shown in FIG. 1.

The method 700 further includes an act 704 of, with the one or more activity sensors, sensing the at least one characteristic of at least one muscle or at least one joint of the at least one body part. As previously discussed, the at least one characteristic can include at least one of nerve activity of the at least one muscle of the at least one body part, temperature of the at least one muscle or the at least one joint of the at least one body part, oxygenation of the at least one muscle of the at least one body part, acoustic emission from the at least one joint of the at least one body part, or other suitable characteristic that can be correlated to muscle or joint activity. Furthermore, in one or more embodiments, the one more activity sensors can sense only the muscle activity (e.g., one or more muscle activity sensors) or sense only joint activity (e.g., one or more joint activity sensors).

The method 700 also includes an act 706 of, responsive to sensing the at least one characteristic via the one or more activity sensors, actuating the one or more actuators to cause the at least one flexible compression garment to selectively compress against or selectively relieve compression against the at least one body part. For example, in an embodiment, actuating the one or more actuators to cause the at least one flexible compression garment to selectively compress against the at least one body part is responsive to the at least one characteristic sensed by one or more activity sensors being over or below a threshold level, such as indicative of the at least one muscle being injured, exerted, or strained past a strain limit. For example, such a threshold level can be stored in memory of a garment system such as the memory 512 of the garment system 500.

Figure 8:
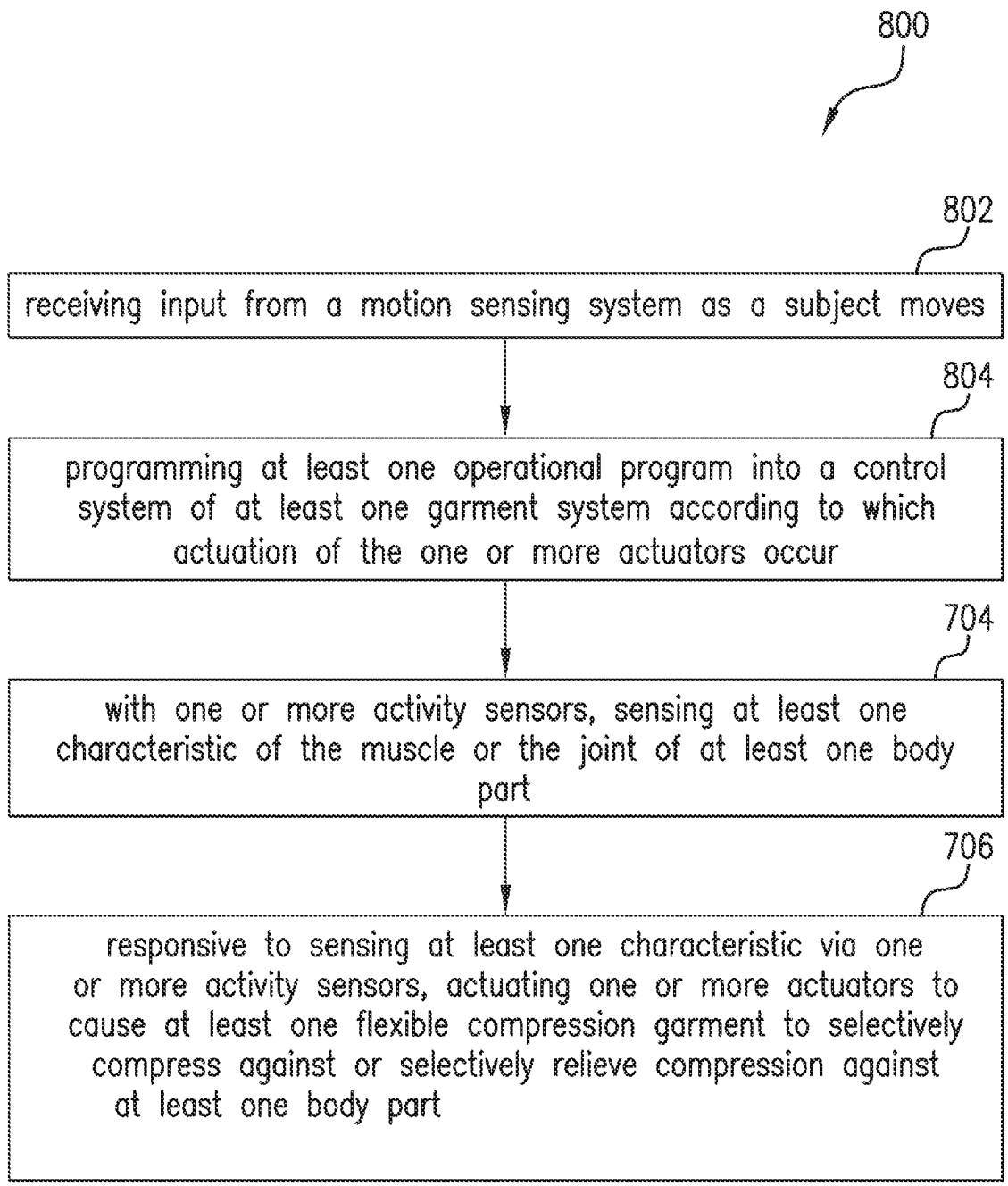
FIG. 8 is a flow diagram of an embodiment of a method in which a garment system receives input from a motion sensing system, according to an embodiment.

Referring to FIG. 8, an embodiment of a method 800 includes an act 802 of receiving input from a motion sensing system as the subject moves. The method 800 further includes, responsive to receiving the input, an act 804 of programming at least one operational program into a control system of the at least one garment according to which actuation of the one or more actuators occurs. The method 800 includes the act 704 of with the one or more activity sensors, sensing the at least one characteristic of at least one muscle or at least one joint of the at least one body part as disclosed above. The method 800 responsive to sensing the at least one characteristic via the one or more activity sensors, includes the act 706 of actuating the one or more actuators to cause the at least one flexible compression garment to selectively compress against or selectively relieve compression against the at least one body part as disclosed above.

The method 800 can include the act 704 disclosed above with respect to the method 700. For example, the method 800 can include sensing the at least one characteristic of at least one muscle or at least one joint of the at least one body part, with the one or more activity sensors, as disclosed above with respect to the act 704. In embodiments, the method 800 can include the act 706 as disclosed above with respect to the method 700. For example, the method 800 can include, responsive to sensing the at least one characteristic via the one or more activity sensors, actuating the one or more actuators to cause the at least one flexible compression garment to selectively compress against or selectively relieve compression against the at least one body part. Actuating the one or more sensors in the act 706 can be performed in accordance with at last one operational program, such as the at least one operational program input into the control system in the act 804 disclosed above.

In embodiments, any of the acts of the method 800 can be omitted or performed in a different order than presented.

Thus, in an embodiment, actuating the one or more actuators to cause the at least one flexible compression garment to selectively compress against or selectively relieve compression against the at least one body part occurs according to a pre-programmed at least one operational program. For example, the at least one operational program can be programmed into memory of a control system that controls the one or more actuators, such as the garment system 500 shown in FIG. 5. In an embodiment, the at least one operational program is related to skills training for at least one selected activity, such as strength training, golf, baseball, basketball, handball, tennis, football, billiards, darts, or Frisbee, or physical therapy.

In an embodiment, a flexible compression garment can be equipped to selectively deliver radiation (e.g., therapeutic radiation) to one or more regions within the at least one flexible compression garment, such as responsive to sensor data. The at least one flexible compression garment can be equipped with one or more therapeutic stimulation delivery devices to equipped selectively deliver the radiation to one or more regions within the at least one flexible compression garment. The at least one flexible compression garment can include one or more sensors (e.g., a plurality of sensors) positioned to sense at least one characteristic of at least one body part associated with the flexible compression garment (e.g., disposed therein) that is related to at least one of movement or a physiological state of the at least one body part (e.g., a motion, a pattern of motion, a conductance, pH, physiological analyte content, etc.). A control system (e.g., controller) can selectively control application of the radiation based upon sensed information of the at least one characteristic of at least one body part related to at least one of movement or a physiological state of the at least one body part.

Figure 9:
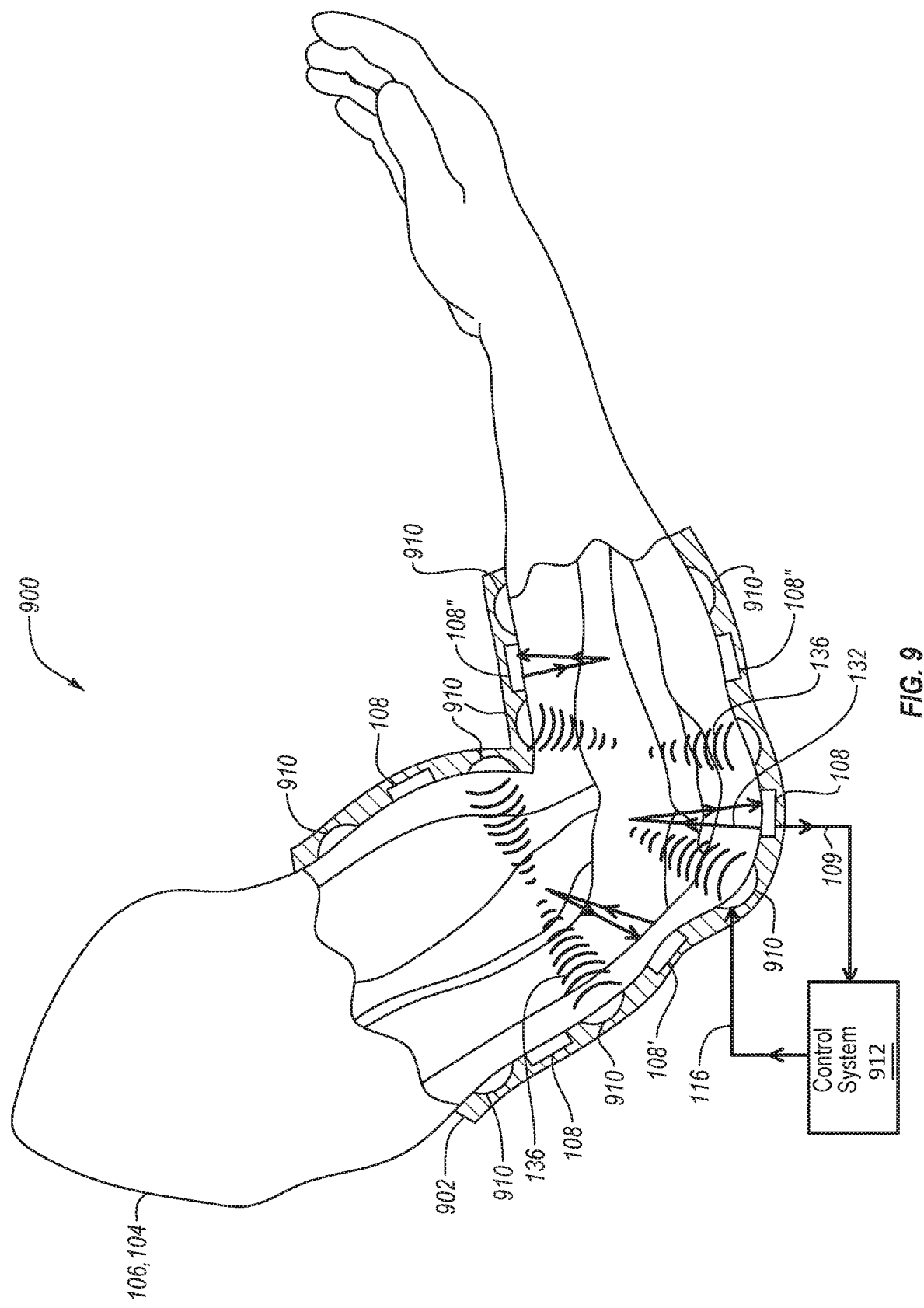
FIG. 9 is a partial cutaway view of a garment system, according to an embodiment.

FIG. 9 is a partial cutaway view of a garment system 900, according to an embodiment. The garment system 900 includes at least one flexible compression garment 902; one or more sensors 108, 108', or 108"; one or more TSDDs 910; and a control system 912 including control electrical circuitry. The at least one flexible compression garment 902 can include one or more sensors 108, 108', or 108" disposed therein or thereon. The at least one flexible compression garment 902 can include one or more TSDDs 910 disposed therein or thereon. The at least one flexible compression garment 902 can include a control system 912 (e.g., controller) associated therewith (e.g., disposed thereon or remote therefrom).

The at least one flexible compression garment 902 can be similar or identical to any of the flexible compression garments disclosed herein, in one or more aspects (e.g., material(s), wearable configuration, etc.). The at least one flexible compression garment 902 can include an interior surface defining an interior space sized and positioned to receive the at least one body part 104. That is, the at least one flexible compression garment 902 can be sized, shaped, and otherwise formed to be worn on at least one body part 104 of a subject 106. For example, the at least one flexible compression garment 902 can include a portion that is substantially tubular and configured to generally conform to the at least one body part of the subject 106, wherein the at least one body part includes at least a portion of an arm, at least a portion of an elbow, at least a portion of a forearm, at least a portion of a wrist, at least a portion of a hand, at least a portion of a finger, at least a portion of a thigh, at least a portion of a knee, at least a portion of a lower leg, at least a portion of an ankle, at least a portion of a foot, at least a portion of a toe, at least a portion of a neck, at least a portion of the head (including the jaw), at least a portion of a back, at least a portion of a spine, at least a portion of a torso, at least a portion of a waist, at least a portion of a gluteal region, at least a portion of the abdominal region, or at least a portion of a chest of the subject 106.

The one or more sensors 108, 108', or 108" can sense at least one characteristic of the at least one body part that is related to at least one of movement or a physiological state of the at least one body part. The one or more sensors 108, 108', or 108" can output one or more sensing signals 109 indicative of the at least one characteristic, such as via a wireless or wired connection to the control system 912. The one or more sensors 108, 108', or 108" can be positioned on, within, or at least partially embedded within the at least one flexible compression garment 902, such as on an inner or outer surface thereof. The one or more sensors 108, 108', or 108" can be positioned on the at least one flexible compression garment 902 at a position selected to detect one or more specific movements or physiological states of the at least one body part. For example, the sensor 108 can be positioned proximate to a bicep to detect electrical signals, strain measurements, or other indicia indicative of contraction, extension, or injury of the bicep. The one or more sensors 108, 108', or 108" can be operably coupled to the control system 912 and output sensed data, via one or more sensing signals 109, to the control system 912. In an embodiment, at least some of the one or more sensors 108, 108', or 108" can be wirelessly coupled or hardwired to the control system 912.

In an embodiment, the one or more sensors 108, 108', or 108" can detect at least one characteristic of the at least one body part that is related to at least one of movement or a physiological state of the at least one body part. For example, the at least one characteristic can include at least one of nerve activity of at least tissue in the region, an internal temperature of the region, an external temperature, blood flow in the region, tissue oxygenation in the region, a strain on the at least one body part, a conductance in the region, an impedance in the region, a pH in a body fluid in the region, a chemical composition of a physiological analyte in the region, an acoustic emission from tissue in the region, a biochemical activity in the region, changes of any of the foregoing exceeding a threshold value, or occurrence or cessation of any of the foregoing for a duration longer than a selected duration of time. In an embodiment, the at least one characteristic of the at least one body part that is related to at least one of movement or a physiological state of the at least one body part can include one or more of a motion of the subject (e.g., walking motions, change in global position, chest expansion and contraction of breathing, etc.), a motion of the at least one body part such as one or more limbs of the subject (e.g., running motion of legs, limping motion of legs, swinging motion of arms, etc.), a stationary condition of the subject (e.g., no change of global position for a selected duration of time), or a stationary condition of the at least one body part such as one or more limbs of the subject (e.g., sedentary or legs not moving for a selected duration of time while arms may be moving). Such characteristics related to movement can be detected by one or more motion sensors included in the one or more sensors 108, 108', or 108". For example, the one or more sensors 108, 108', or 108" can include an accelerometer, a GPS, or any other sensor configured to detect a characteristic related to movement of at least one body part. In an embodiment, the one or more sensors 108, 108', or 108" can sense characteristics indicative of onset of muscle activity, a conclusion of muscle activity, a threshold level of muscle activity in the region, muscular fatigue, tissue swelling, or an indication of pain (e.g., one or more chemical or electrical indications of pain).

In an embodiment, the one or more sensors 108, 108', or 108" can include at least one of an electrophysiological sensor, a myography sensor (e.g., myograph), a thermal sensor, a near infrared sensor, a blood flow sensor, a timer (e.g., clock), an oxygenation sensor, a chemical sensor, a motion sensor, a global positioning system ("GPS"), a strain sensor, a pressure sensor, a temperature sensor, an optical sensor (e.g., an LED, a pulse oximeter, etc.) an electrode, a bioimpedance sensor, a pH sensor, an acoustic sensor, or any other sensor suitable to detect any of the at least one characteristic of the at least one body part that is related to at least one of movement or a physiological state of the at least one body part described herein. Sensors not dedicated to directly sensing a motion may be termed physiological sensors. For example, physiological sensors can include electrophysiological sensors, chemical sensors, electrical sensors, a pH sensor, a timer, a strain sensor, a pressure sensor, etc.

The electrophysiological sensors can detect one or more electrical properties associated with biological cells or tissues, or fluids secreted therefrom, and can include one or more of an electroencephalograph (EEG) (e.g., for measuring electrical activity of the brain), electrocardiograph (ECG) (e.g., for cardiac electrical activity measurements), electromyograph (EMG) (e.g., for measuring electrical activity of muscle), the surface EMG (e.g., a noninvasive type of EMG), the microneurograph (e.g., for electrical activity measurements in nerve fibers), skin conductance sensor, a bioimpedance sensor, an electrooculograph, or the like. For example, an electrophysiology sensor such as an EEG, ECG, or EMG (e.g., surface EMG) can include one or more capacitive sensors or silicon metal oxide semiconductor field effect transistors (MOSFETs). For example, an electrophysiology sensor such as an ECG can include one or more of a dry electrode or a conducting polymer comprising adhesive polymer (e.g., polydimethylsiloxane) mixed with a conducting material such as silver microspheres, silver nanowires, or carbon nanotubes. For example, a surface EMG can include a piezoelectric thin film sensor. In an embodiment, the electrophysiological sensor(s) can include an array of electrophysiological sensors.

A myography sensor (e.g., myograph) can include one or more electromyography sensors, one or more accelerometer myography sensors, one or more mechanomyography sensors, or one or more acoustic myography sensors. The myograph sensor can detect a physiological parameter of the at least one body part, such as by detecting one or more properties associated with one or more muscles, and can include one or more of EMG, surface EMG, acoustic myography sensors (e.g., for measuring sound in muscle movement), mechanomyography sensors (e.g., for measuring oscillations in muscle contraction), accelerometer myography sensors, or the like. For example, a mechanomyography sensor can include (as a detector) a condenser microphone, an accelerometer, a laser-based instrument, and the like. For example, an acoustic myographic sensor can include an acoustic transducer. For example, an acoustic myographic sensor can include an acoustic sensor having a microphone.

In an embodiment, the one or more sensors 108, 108', or 108" can include an electrophysiological sensor to detect one or more electrical (e.g., bioelectrical) signals in the region. The electrophysiological sensor can include one or more electrodes. The electrophysiological sensor can be configured to detect one or more nerve signals in a region of the at least one body part, such as one or more electrical or chemical signals of one or more muscles in the at least one region of the at least one body part. The one or more electrodes can include one or more of ion-selective electrodes (e.g., potentiometric electrodes), an electrochemical sensor, a gold nanoparticle/aptamer modified electrodes, amperometric enzymatic electrodes, amplified sensor electrodes (e.g., including silicon metal oxide semiconductor filed effect transistors), reverse iontophoresis electrodes, micro-needles, etc. The amperometric enzymatic electrodes can detect sugars or derivatives thereof (e.g., glucose, lactate, etc.) in sweat, saliva, body tissue (e.g., blood or interstitial tissue) using glucose oxidase or lactate oxidase. The ion-selective electrodes can detect one or more electrolytes such as sodium, potassium, etc., or a pH of a fluid or tissue, such as sweat, saliva, body tissue (e.g., blood or interstitial tissue). The gold nanoparticle/aptamer modified electrodes can detect proteins in fluids, such as sweat, saliva, body tissue, etc. The amplified sensor electrodes can detect electrical sensors in fluids, such as sweat, saliva, body tissue, etc.

In an embodiment, the one or more sensors 108, 108', or 108" can include an electrophysiological sensor configured to measure bioelectrical signals, wherein the bioelectrical signals can be indicative of a pain state of the individual subject. In an embodiment, the electrophysiological sensor includes an EMG for detecting a bioelectrical signal in a muscle as a localized or systemic indicator of pain. For example, a surface EMG positioned on a biceps muscle measures bioelectric activity indicating overuse and fatigue associated with pain or the risk (e.g., probability) of pain. For example, a surface EMG positioned on a muscle during repetitive work can measure bioelectric activity indicative of repetitive injury stress and related pain or risk of pain. For example, a surface EMG positioned on a muscle during exercise can detect bioelectric signals indicative of a sustained muscle contraction (e.g., a muscle spasm or cramp) associated with pain. In an embodiment, the electrophysiological sensor includes an EMG for detecting a bioelectrical signal in a muscle positioned relative to a second at least one body part during a movement of one or more of the first at least one body part and the second at least one body part. For example, the garment system can be positioned on a wrist of the individual subject and the motion sensor can include an electromyograph configured to detect movement in one or more fingers.

In an embodiment, the one or more sensors 108, 108', or 108" include a sensor array or assembly. The sensor array can include the electrophysiological sensor, microneurograph, or myograph configured to distinctly measure electrical activity mediated by A delta (Aδ) nerve fibers (e.g., indicative of sharp, localized pain). In an embodiment, the sensor array can include the electrophysiological sensor, microneurograph, or myograph configured to distinctly measure electrical activity mediated by C nerve fibers (e.g., indicative of diffuse pain, such as that associated with inflammation). In an embodiment, the electrophysiological sensor, microneurograph, or myograph can be configured to measure electrical activity mediated by A delta (Aδ) fibers and C fibers, where the one or more sensing signals from the sensor assembly are transmitted to the control electrical circuitry only when the one of the A delta (Aδ) fibers or the C fibers are inactive when the other of the A delta (Aδ) fibers or the C fibers are active. Alternatively, the sensor array can transmit the one or more sensing signals when each of the A delta (Aδ) fibers and C fibers are active, whereby the control electrical circuitry is configured to disregard portions of the sensing signals corresponding to one of the A delta (Aδ) fibers or the C fibers.

In an embodiment, the one or more sensors 108, 108', or 108" can include a myograph (e.g., acoustic myography sensor or mechanomyography sensor) configured to measure a signal (e.g., an acoustic signal or a mechanical signal) associated with a muscle contraction, wherein the signal associated with a muscle contraction can be indicative of a pain state of the individual subject. For example, an acoustic myography sensor can measure sound waves arising from muscle fiber contractions to assess muscle activity to determine when a muscle or muscle group is being misused (e.g., overworked), leading to pain and injury.

In an embodiment, the one or more sensors 108, 108', or 108" can include the temperature sensor. For example, temperature sensors comprising thermal and/or optical sensors can detect increased tissue temperatures (e.g., in muscle or adjacent skin) associated with delayed onset muscle soreness (DOMS) (e.g., exercise-induced muscle damage), such as within the first hours post-exercise.

In an embodiment, the thermal or temperature sensor can include a passive infrared sensor positioned and configured to sense infrared radiation from the region. In such embodiments, the infrared radiation can be indicative of a temperature of a region of the at least one body part. In an embodiment, the thermal sensor can include a microwave device positioned to sense microwave radiation from at least a region of the at least one body part 104. The microwave radiation can be indicative of a temperature. In an embodiment, the oxygenation sensor can include a passive infrared sensor. In such embodiments, the infrared radiation can be indicative of an amount of oxygen in the blood in a region of the at least one body part.

In an embodiment, the one or more sensors 108, 108', or 108" can include an optical sensor. In an embodiment, the optical sensor can be configured to measure a blood flow. In an embodiment, the optical sensor can be configured to measure temperature associated with the body portion. In an embodiment, the optical sensor can be configured to measure a pressure, strain, or deformation characteristic associated with the body portion (e.g., in swollen tissue). In an embodiment, the optical sensor can measure a heart rate or respiratory rate. In an embodiment, the optical sensor can measure at least one of transmitted light or reflected light. For example, the optical sensor can include, but is not limited to, a photodiode, a light-emitting diode (LED), an LED coordinated with a photosensor (e.g., photodetector), a fiber optic sensor (e.g., fiber optic strand, fiber Bragg Grating sensors; fluoroptic sensors), a flexible photonic sensor, an oximeter (e.g., pulse oximeter), an imaging device such as a camera, or combinations thereof. In an embodiment, the physiological sensor can include a near infrared sensor configured to measure a physiological characteristic of the at least one body part, such as tissue oxygenation or a blood analyte (e.g., oxygen, carbon monoxide, met-hemoglobin, total hemoglobin, glucose, a protein, or a lipid), or to measure brain activity (e.g., prefrontal cortex activity associated with nociception). For example, hypoxemia in muscle, detectable by NIR oximetry, is associated with activation of nerve receptors and increased pain. For example, decreased blood flow in skin resulting in hypoxemia or ischemia as detected by the oximeter can be an indication of or associated with pain or a risk of pain, such as from pressure sores.

In an embodiment, the one or more sensors 108, 108', or 108" can detect changes in one or more physiological parameters indicative of autonomic nervous system responses, including, but not limited to changes in biopotentials, electrophysiological signals, heart rate, heart rate variability, arterial blood pressure, plethysmograph wave amplitude, skin conductance level, number of skin conductance fluctuations and their time derivatives, etc. Changes in the autonomic nervous system, including changes in biopotentials and electrophysiological signals, can be indicators of the presence of pain. For example, ECG can measure heart rate variability; a reduction of the heart rate variability power in the high frequency band (e.g., 0.15-0.4 Hz) can be indicative of pain onset. For example, an oximeter (e.g., a pulse oximeter or photo-plethysmograph) can assess vasoconstriction; a reduction in the photo-plethysmographic waveform amplitude caused by peripheral vasoconstriction and detectable by the oximeter can be indicative of pain. For example, skin conductance sensor can detect changes in skin conductance; changes in electro-galvanic skin properties, which can be measured by changes in the level and number of skin conductance fluctuations, can be indicative of the presence of pain. For example, surface EMG can detect changes in the bioelectric signal in the muscle; changes in muscle tone, which are directed by the autonomic nervous system, can be indicative of the presence of pain.

The one or more sensors 108, 108', or 108", (or control electrical circuitry) can extract sensed information and transmit the same in the sensing signal 109 (e.g., a detected electrophysiological signal). For example, the ECG captures electrophysiological signal from the heart and the signal can include features such as heart rate, interbeat interval, and heart rate variability that can be independently assessed (e.g., a reduction of the heart rate variability can be indicative of pain onset). For example, EMG captures signal from the muscle, and the signal includes such features as amplitudes, frequency, etc. that can be independently assessed (e.g., changes in the amplitude and entropy of an EMG signal can be indicative of the presence of pain). Extraction of the sensed information from the sensing signals 109 can aid in determination of the presence of an indication of pain.

In an embodiment, one or more of the one or more sensors 108, 108', or 108" (e.g., physiological sensors) are configured to combine two or more physiological parameters (e.g., autonomic response parameters) and provide a single multi-parameter sensing signal 109. In an embodiment, one or more of the one or more sensors 108, 108', or 108" are configured to provide signals encoding two or more physiological parameters related to a physiological state of the at least one body part to the control electrical circuitry, which can combine the information into a single multi-parameter signal. In an embodiment, the control system 912 is configured to assess a multi-parameter composite of autonomic signals to determine an indication of the presence of pain. In an embodiment, the physiological sensor can be configured to detect changes in one or more physiological parameters related to a physiological state of the at least one body part that are indicative of responses in the autonomic nervous system for use in quantifying a pain state. For example, quantifiable changes in biopotentials and electrophysiological signals, can be indicators of pain intensity. For example, higher skin conductance levels, as measured by a skin conductance sensor, can be indicative of high intensity pain.

In an embodiment, the one or more sensors 108, 108', or 108" can stimulate the region of the at least one body part with sensing radiation and receive reflected sensing radiation responsive thereto. For example, the sensor 108 in FIG. 9 can include an acoustic sensor. The acoustic sensor can receive acoustic emissions from the at least one body part or a specific region thereof and/or can emit acoustic radiation and receive reflected acoustic radiation. In an embodiment, the acoustic radiation and the reflected acoustic radiation can include ultrasound (e.g., ultrasonic) radiation. In such embodiments, the one or more sensors 108, 108', or 108" can include one or more ultrasound transducers, transmitters, receivers, or transceivers.

In an embodiment, the one or more sensors 108, 108', or 108" can include one or more motion sensors, which can include one or more of an accelerometer, a GPS, an infrared sensor, or any other sensor capable of detecting motion or a change of position of at least a portion of the subject. The motion sensors can to detect one or more of motion of the subject 106 (e.g., change in global position), a motion of the at least one body part such as one or more limbs of the subject 106, a stationary condition of the subject 106, a stationary condition of the at least one body part such as one or more limbs of the subject 106, or a duration since a last occurrence of any of the foregoing.

In an embodiment, the one or more sensors 108, 108', or 108" can include one or more chemical sensors which can detect one or more physiological analytes associated with the subject. For example, the one or more chemical sensors can detect one or more physiological analytes (e.g., a chemical, derivative thereof, or indicator thereof) present in sweat, tissue (e.g., blood or interstitial tissue), saliva, or any other body fluid. In an embodiment, the one or more chemical sensors can detect detect one or more of a sugar (e.g., a saccharide such as glucose), a salt, an organic compound (e.g., lactate, an alcohol, etc.), an electrolyte, a hormone (e.g., cortisol, pregnenolone, dehydroepiandrosterone ("DHEA"), testosterone, progesterone, estrogen, triiodothyronine ("T3"), and thyroxine ("T4")), a neuropeptide (e.g., neuropeptide Y, substance P, and calcitonin-gene-related peptide (CGRP)), a peptide, a protein (e.g., pro-inflammatory cytokine (IL-1$\alpha$, IL-$\beta$, IL-6, TNF$\alpha$, IL-8, etc.), a nucleotide, derivatives (e.g., salts or metabolites) of any of the foregoing, or oxygen. In an embodiment, the one or more chemical sensors can include an at least one electrode. In an embodiment, the one or more chemical sensors can include a transdermal sensor, such as an iontophoretic device. For example, a reverse iontophoresis sensor can be used to transdermally detect one or more analytes present in a tissue or body fluid of the subject.

In an embodiment, the physiological sensor includes the chemical sensor configured to measure a physiological analyte present in a tissue or body fluid of the subject that may be indicative of a pain state of the subject. In an embodiment, the chemical sensor can include a sensor for detecting an analyte in sweat. For example, the chemical sensor can include a sensor for detecting increased levels of a saccharide such as glucose or of a salt such as lactate or glutamate, in sweat. For example, the chemical sensor can include a sensor for detecting a hormone (e.g., cortisol or adrenaline). For example, the chemical sensor can include a sensor for detecting inflammatory mediators (e.g., a prostaglandin (e.g., PGE), bradykinin, serotonin, adenosine triphosphate, pyruvate, etc.) or a pro-inflammatory cytokine (IL-$\alpha$, IL-$\beta$, IL-6, TNF$\alpha$, IL-8). The chemical sensor can include a sensor for detecting a change in pH. For example, the chemical sensor can include a sensor for detecting an ion or electrolyte (e.g., hydrogen, sodium, potassium, chloride, calcium, magnesium, phosphate, etc.). In an embodiment, the chemical sensor includes a multiplexed sweat sensor array with an amperometric glucose sensor, an amperometric lactate sensor, or combinations thereof, which can include glucose oxidase and lactate oxidase. The multiplexed sweat sensor array can additionally or alternatively include ion-selective electrodes (e.g., for determination of sodium and potassium levels) with a reference electrode, which can include a polyvinyl butyral (PVB)-coated electrode. The multiplexed sweat sensor array can additionally or alternatively include a temperature sensor. In an embodiment, the chemical sensor can include a graphene-based sweat sensor. For example, the chemical sensor can include a sensor for detecting a protein (e.g., of a pro-inflammatory cytokine, inflammatory mediator, hormone, etc.) or peptide thereof in sweat. In an embodiment, the chemical sensor can include a transdermal sensor for sensing an analyte in tissue fluids (e.g., blood). For example, the chemical sensor can include a sensor configured for reverse iontophoresis (e.g., reverse iontophoretic extraction) to draw an analyte (e.g., glucose) from an interstitial space without puncturing the skin.

Changes in levels of physiological chemicals have been associated with increased muscle use or the presence of a pain condition (e.g., presence of an indication of pain). For instance, increases in lactate levels or in glucose levels (e.g., in response to released hormones), measurable in sweat or bodily tissues (e.g., interstitial tissues), can be associated with increased muscle use or the presence of pain. For example, increased levels of one or more hormones (e.g., cortisol, pregnenolone, DHEA, adrenocorticotrophic hormone (ACTH), a catecholamine (e.g., adrenaline or noradrenaline) testosterone, progesterone, estrogen, thyroid releasing hormone (TRH), triiodothyronine (T), thyroxine (T),) released in response to pain are measurable in sweat or other bodily fluids. For example, neuropeptides (e.g., neuropeptide Y, substance P and calcitonin-gene-related peptide (CGRP)) or other neurotransmitters (e.g., glutamate), which are released in response to pain are measurable in sweat or other bodily fluids. For example, pain (e.g., tenderness, allodynia, and hyperalgesia) is associated with sensitization of muscle nociceptors by endogenous mediators such as bradykinin and PGE released during movement or exercise. For example, increases or imbalances in levels of adenosine triphosphate (ATP), and electrolytes, as well as low pH generally can be associated with increased pain experienced by the individual subject; ATP and hydrogen ions are irritants that activate nerve endings by binding to receptor molecules, and pathological and pathophysiological changes of skeletal muscle are accompanied by a drop in pH. For example, increased tissue metabolism during exercise leads to decreased oxygen levels (detectable by oximetry), causing a drop in pH and accumulation of hydrogen atoms (detectable as above), which in turn can activate nerve endings to induce pain. For example, muscle spasm (persistent, involuntary muscle contraction) is accompanied by muscle ischemia, which leads to a drop in pH and the release of pain-producing substances such as bradykinin, ATP, and hydrogen ions. For example, an alteration in the levels of an electrolyte might be associated with ion channel (e.g., Transient Receptor Potential family members) in the activation of nociceptive receptors.

In an embodiment, the chemical sensor can include an electrochemical sensor. For example, the electrochemical sensor can include an amperometric enzymatic electrode, which utilizes glucose oxidase to detect glucose or lactate oxidase to detect lactate, or one or more ion-selective electrodes (e.g., potentiometric), which can detect electrolytes (e.g., sodium, potassium) and can be utilized for pH monitoring. In an embodiment, the electrochemical sensor can include a ligand, such as an aptamer. For example, a gold nanoparticle/aptamer-modified electrode can be used to detect a protein. In an embodiment, the chemical sensor can include microfluidics. In an embodiment, a sensor can include a dolorimeter or algesiometer.

In an embodiment, the chemical sensor can include a transdermal sampling component such as a one or more needles or micro-needles. Such micro-needles can access interior spaces of the at least one body part 104, such as dermal or sub dermal regions of the at least one body part 104, to detect one or more chemicals in fluids or body tissues therein.

In an embodiment, the chemical sensor can include an antagonist and/or agonist delivery device to deliver an antagonist and/or agonist, which can be composed to produce physiological response or physiological analyte. For example, the antagonist and/or agonist delivery device can include one or more of a patch, reservoir, or micro-needles having the agonist and/or antagonist therein. The antagonist and/or agonist delivery device can include a pilocarpine delivery device having pilocarpine therein. Upon activation, the pilocarpine delivery device can release pilocarpine thereby increasing perspiration and/or salivary function at the site. One or more additional chemical sensors can be used to examine the sweat and/or saliva for physiological analytes (e.g., chemicals or derivatives thereof, such as chloride, sodium, magnesium, etc.) and/or concentrations thereof. For example, a pilocarpine delivery device can include an iontophoretic device (e.g., a first electrode in combination with pilocarpine disposed between the skin and the first electrode, and a second (counter) electrode) configured to deliver pilocarpine) can be used to induce sweating using pilocarpine as an agonist. The one or more sensors 108, 108', or 108" can include a chemical or ion sensor set up to detect an amount of chloride or another ion in the sweat of the subject (e.g., determine if a subject is dehydrated or possibly has cystic fibrosis). Further antagonists or agonists can be used, such as capsaicin, cholinergic agonists, etc.

In an embodiment (not shown), at least one of the one or more sensors 108, 108', or 108" can be remote from the at least one compression garment 902, such as on one or more of a wearable device, a portable device (e.g., remote sensor device, a mobile phone, or a tablet) or array thereof, or a fixed device or station (e.g., scanning appliance on a desk, table, or wall; a room scanner; a motion capture device; etc.).

In an embodiment, at least one of the one or more sensors 108, 108', or 108" can be disposed at least partially on an interior surface of the at least one flexible compression garment (e.g., in contact with the at least one body part 104). For example, at least one of the one or more sensors 108, 108', or 108" can be partially embedded within the at least one flexible compression garment wherein a surface of the at least one of the one or more sensors 108, 108', or 108" is co-extensive with the interior surface (e.g., both contact the skin of a subject). In an embodiment, at least one of the one or more sensors 108, 108', or 108" can be positioned on the interior surface of the at least one flexible compression garment and extend therefrom. In an embodiment, at least some of the one or more sensors 108, 108', or 108" can positioned adjacent to or in the proximity of one or more TSDDs. For example, a sensor 108, 108', or 108" may detect at least one characteristic of the at least one body part that is related to at least one of movement or a physiological state of the at least one body part, such as in a specific region thereof, wherein the specific region is within an effective treatment range or direction of the one or more TSDDs adjacent thereto.

Referring back to FIG. 9, the at least one TSDD 910 of the garment system 900 can be positioned (with respect to the at least one compression garment 902) to apply radiation to the at least one body part, such as in a selected region thereof. In an embodiment and as shown in FIG. 9, the at least one TSDD 910 can include a plurality of TSDDs 910. In an embodiment, at least some of the plurality of TSDDs (e.g., all of the TSDDs) can be identical, or at least one of the plurality of TSDDs 910 can be of a different type or configuration (e.g., configured to emit a different type, intensity, or wavelength of radiation) than others of the plurality of TSDDs 910.

In an embodiment, the at least one TSDD 910 can include at least one acoustic emitter, such as a radio frequency emitter, an ultrasound emitter, etc. In an embodiment, the at least one TSDD 910 can include at least one ultrasound transducer. The at least one ultrasound transducer can be positioned (e.g., in or on the flexible compression garment) to apply acoustic radiation to the at least one body part 104. The at least one ultrasound transducer can emit one or more of low frequency acoustic radiation, high frequency acoustic radiation, low intensity acoustic radiation, high intensity acoustic radiation, or varying frequency and/or intensity acoustic radiation. In an embodiment, the at least one TSDD can emit therapeutic ultrasonic radiation having a frequency of at least about 1000 Hz (e.g., at least about 17,000 Hz), such as in a range of about 0.5 MHz to about 4 MHz, or more specifically a range of about 0.8 MHz to about 3 MHz. In such embodiments, ultrasonic radiation below about 1.5 MHz can be deemed low frequency, and ultrasonic radiation above about 2 MHz can be deemed high frequency. In an embodiment, the at least one TSDD can emit therapeutic ultrasonic radiation having an intensity of at least about 0.1 W/cm$^2$, such as in a range of about 0.1 W/cm$^2$ to about 700 W/cm$^2$, or more specifically a range of about 1 W/cm$^2$ to about 300 W/cm$^2$. The TSDDs 910 can be configured to delivery any combination of intensity and frequency disclosed herein.

In an embodiment, the at least one ultrasound transducer can apply acoustic radiation to the at least one body part 104 effective to block one or more nerves therein from receiving one or more nerve signals, such as blocking pain receptors. In an embodiment, the at least one ultrasound transducer can apply acoustic radiation to the at least one body part 104 effective to control a temperature (e.g., increase, decrease, or maintain) of a region of the at least one body part 104. For example, the at least one ultrasound transducer can emit one or more wavelengths, frequencies, or intensities of acoustic radiation effective to raise a temperature of a region of the at least one body part 104. The at least one ultrasound transducer can emit a steady wavelength, frequency, or intensity of acoustic radiation for a selected duration of time (e.g., continuously emit for the duration). For example, a selected wavelength of acoustic radiation can be emitted for at least about 1 second, such as about 1 second to about 1 hour, about 2 minutes to about 30 minutes, about 5 minutes to about 20 minutes, about 1 minute to about 3 hours, about 1 hour to about 4 hours, less than about 10 minutes, less than about 20 minutes, less than about 30 minutes, less than about 1 hour, or more than about 5 minutes. In examples, a selected wavelength of acoustic radiation can be emitted for less than 1 second (e.g., a fraction of a second, a millisecond, etc.). In an embodiment, the at least one ultrasound transducer can emit one or more pulses of a selected wavelength, frequency, or intensity of acoustic radiation. Each of the one or more pulses can be maintained for a selected duration of time such as any of those noted above, or on a scale of seconds or fractions of a second. For example, each of the one or more pulses can be at least about 0.1 seconds ("s"), such as about 0.1 s to about 10 s, about 1 s to about 5 s, about 2 s to about 4 s, about 3 s to about 7 s, about 6 s to about 10 s, about 0.1 s to about 3 s, more than about 1 s, more than about 10 s, more than about 5 s, less than about 10 s, less than about 5 s, or less than about 2 s.

In an embodiment, a first pulse can have a first wavelength, frequency, or intensity of acoustic radiation and at least a second pulse can have a second wavelength, frequency, or intensity of acoustic radiation. The second wavelength, frequency, or intensity of acoustic radiation can be higher or lower than the first wavelength, frequency, or intensity of acoustic radiation. In an embodiment, each successive wavelength, frequency, or intensity of acoustic radiation pulses after the first wavelength, frequency, or intensity of acoustic radiation can be increasing, decreasing, maintained, or vary according to a treatment regimen (e.g., a plurality of pulses of selected wavelength(s), frequency(s), or intensity(s) of acoustic radiation). The treatment regimen can be implemented according to instructions stored on the memory as executed by the control electrical circuitry (e.g., processor) of the control system 912.

In an embodiment, the at least one TSDD 910 can include at least one electrode positioned and equipped to deliver electromagnetic radiation to the at least one body part. For example, the at least one electrode can include one or more electrodes positioned and configured to stimulate a tissue in the at least one body part. For example, the at least one electrode can include one or more electrodes positioned and configured to block one or more nerve signals (e.g., pain signals) in the at least one body part.

In an embodiment, the at least one TSDD 910 can include at least one magnetic field generator positioned and equipped to deliver electromagnetic radiation (e.g., a magnetic field) to the at least one body part. For example, the at least one magnetic field generator can include one or more magnetic field generators positioned and configured to stimulate a tissue in the at least one body part. For example, the at least one magnetic field generator can include one or more electrodes, electromagnets, or coils positioned and configured to block one or more nerve signals (e.g., pain signals) in the at least one body part.

In an embodiment, the at least one TSDD 910 can include at least optical stimulator positioned and equipped to deliver optical stimulation (e.g., infrared radiation, visible light radiation, etc.) to the at least one body part. For example, the at least one optical stimulator can include one or more optical stimulators positioned and configured to stimulate a tissue in the at least one body part. For example, the at least one optical stimulator can include one or more electrodes positioned and configured to block one or more nerve signals (e.g., pain signals) in the at least one body part, such as via emitting low intensity pulsed infrared light. In an embodiment, the at least one optical stimulator can include an infrared light source, an ultraviolet light source, a visible light source, or a multispectral light source.

In an embodiment, the at least one TSDD 910 can include at least one thermal device positioned and equipped to deliver thermal stimulation (e.g., heat or cooling such as via infrared radiation, etc.) to the at least one body part. For example, the at least one thermal device can include one or more thermal devices (e.g., infrared light source or acoustic transducers) positioned and configured to stimulate a tissue in the at least one body part. For example, the at least one thermal device can include one or more thermal devices positioned and configured to block one or more nerve signals (e.g., pain signals) in the at least one body part, stimulate nerves, or heat one or more tissues, such as via emitting heat (e.g., infrared radiation).

In an embodiment, the at least one TSDD 910 can include at least microwave emitter positioned and equipped to deliver microwave stimulation (e.g., microwave radiation) to the at least one body part. For example, the at least one microwave emitter can include one or more microwave emitters positioned and configured to stimulate a tissue in the at least one body part. For example, the at least one microwave emitter can include one or more microwave emitters positioned and configured to block one or more nerve signals (e.g., pain signals) in the at least one body part, such as via emitting low intensity pulsed microwaves.

Any of the TSDDs 910 disclosed herein can be configured to emit a continuous stream or one or more pulses of therapeutic radiation therefrom. For example, an ultrasonic transducer can emit a plurality of pulses each lasting a selected duration and/or having gaps therebetween lasting a selected duration. The selected duration can be about 1 mms or more such as about 1 mms, about 10 mms, about 100 mms, about 500 mms, about 1 s, about 2 s, about 3 s, about 5 s, about 10 s, about 15 s, about 20 s, about 30 s, about 1 minute, about 2 minutes, about 3 minutes, about 4 minutes, about 5 minutes, about 10 minutes, about 15 minutes, about 20 minutes, about 30 minutes, about 1 hour, about 2 hours, about 3 hours, about 4 hours, about 6 hours, about 8 hours, about 12 hours, about 24 hours, or ranges including any combination of the foregoing times as endpoints. In an embodiment, the one or more pulses can include at least 2 pulses, at least, 3 pulses, at least 5 pulses, at least 10 pulses, at least 20 pulses, at least 50 pulses, at least 100 pulses, at least 300 pulses, at least 500 pulses, at least 1,000 pulses, or ranges of pulses including any combination of the foregoing numbers of pulses as endpoints. In an embodiment, the plurality of pulses can be delivered in a selected pattern (e.g., as directed by operational instructions from the control system). In an embodiment, the plurality of pulses can include combinations of any of the types of therapeutic radiations disclosed herein.

In an embodiment, the at least one TSDD 910 can include a plurality of TSDDs (e.g., ultrasound transducers), each positioned and configured to provide radiation (e.g., acoustic radiation) to the at least one body part 104. In an embodiment, the plurality of TSDDs can include a combination of one or more of any of the TSDDs disclosed herein. For example, the array of TSDDs 910 can include one or more of at least one electrode, at least one magnetic field generator, at least one optical stimulator, at least one thermal control device, or at least one microwave emitter. In an embodiment, the plurality of TSDDs (e.g., ultrasound transducers) can be arranged in an array effective to converge radiation (e.g., acoustic radiation) in a common region (e.g., a focal point) of the at least one body part 104, or provide coverage to a plurality of regions of the at least one body part 104. One or more of the plurality of ultrasound transducers (e.g., each) can emit any of the any of the frequencies, wavelengths, intensities, pulses, etc. of acoustic radiation disclosed herein. For example, one or more of the plurality of ultrasound transducers can emit low frequency acoustic radiation. In examples, the plurality of ultrasound transducers can emit a plurality of frequencies of acoustic radiation. In an embodiment, each of the plurality of ultrasound transducers can emit the same wavelength, frequency, or intensity of radiation. In an embodiment, at least some of the plurality of ultrasound transducers can emit a different wavelength, frequency, or intensity of radiation than another ultrasound transducer of the plurality of ultrasound transducers. In an embodiment, one or more of the plurality of ultrasound transducers (e.g., each) can emit one or more pulses of acoustic radiation or can continuously emit acoustic radiation for a selected duration of time.

In an embodiment, the one or more sensors 108, 108', 108" can include at least one scanning acoustic transducer which can apply scanning acoustic radiation 132 to tissue of the at least one body part 104 and receive reflected scanning acoustic radiation responsive thereto, and the at least one TSDD includes a therapeutic ultrasound transducer which can provide therapeutic acoustic radiation 136 to the at least one body part 104. The scanning acoustic radiation 132 and the therapeutic acoustic radiation 136 can differ from one another by one or more of wavelength, frequency, intensity, or duration of application. In an embodiment, the at least one scanning acoustic transducer and at least one therapeutic ultrasound transducer can both be included in a multipurpose ultrasound transducer (e.g., transceiver) configured to selectively emit both a scanning ultrasonic radiation 132 and a therapeutic acoustic (e.g., ultrasonic) radiation 136.

The garment system 900 can selectively direct application of therapeutic radiation responsive to sensing one or more characteristics of the at least one body part 104 related to at least one of movement or a physiological state of the at least one body part 104. Referring to FIG. 9, the control system 912 of the garment system 900 can be similar or identical to the any of the control systems disclosed herein in one or more aspects. For example, the control system 912 can be identical to the control system 508 or 612. The control system 912 can include one or more of control electrical circuitry (e.g., a processor), memory, a power supply, or a user interface. The memory (e.g., a machine readable memory storage medium) can include one or more operational instructions stored thereon. The memory can include a (non-transitory) memory storage medium operably coupled to control electrical circuitry (e.g., processing electrical circuitry). The control electrical circuitry can access and execute the one or more operational instructions stored on the memory storage medium. The control system 912 can be operably coupled to the one or more sensors 108, 108', or 108" to receive one or more sensing signals 109 therefrom. The one or more sensors 108, 108', or 108" can transmit sensed information to the controller via the one or more sensor signals 109. The control system 912 can selectively direct the one or more sensors 108, 108', or 108" to constantly scan, intermittently scan, or scan upon direction, a region of the at least one body part 104. The control system 912 can be operably coupled to one or more TSDDs 910. The control system 912 can selectively activate and/or control the one or more TSDDs 910 to selectively apply therapeutic radiation to the at least one body part 104. For example, the control electrical circuitry (e.g., processing electrical circuitry) can direct the at least one TSDD 910 to selectively apply radiation to the region of the at least one body part, responsive to one or more sensing signals 109 or determinations made based on the sensing signals 109.

A power supply can be operably coupled to any components of the control system 912 to provide power to the components. In an embodiment, the power supply can be disposed in or on the at least one flexible compression garment 902, such as in the control system 912 or on the flexible compression garment 902. In an embodiment, the control system 912 and/or the power supply can be remote from the at least one flexible compression garment, such as on a separate wearable device.

The control system 912 can determine if an activation condition is indicated by interrogating sensing information from the one or more sensors and execute operational instructions based on the determination. The operational instructions can include machine executable instructions for selectively controlling the one or more TSDDs 910. In an embodiment, operational instructions can include one or more treatment regimens composed to selectively treat at least one medical condition using the one or more TSDDs 910. The at least one medical condition can include one or more of arthritis, arthralgia, neuralgia, neuropathic pain, enthesalgia, myalgia, fibromyalgia, cephalgia, muscular pain, or traumatic pain. The one or more treatment regimens can include at least one of an active treatment, a preventative treatment, or a palliative treatment.

In an embodiment, the control electrical circuitry (e.g., processing electrical circuitry) can determine if an activation condition is indicated from the sensed information, such as responsive to receipt of the sensed information. The control electrical circuitry (e.g., processing electrical circuitry) can determine if the activation condition is indicated by comparing the sensed information in the one or more sensing signals 109 with one or more threshold levels stored in the memory storage medium corresponding to the sensed information. For example, the control electrical circuitry can compare the sensed information to one or more threshold values and determine if the sensed information indicates that a threshold value has been met or exceeded. For example, sensed information can include an amount of salt detected in sweat, and the control electrical circuitry can determine if the amount detected in the sweat meets, exceeds, or falls short of a threshold value indicated for dehydration, a physiological indication of pain, or any other condition. Responsive to the determination of the presence or absence of the activation condition (e.g., a threshold level is met, fell short of, or exceeded), the control electrical circuitry can selectively direct the at least on TSDD 910 to selectively control or apply (e.g., initiate, terminate, or alter) therapeutic radiation to a region of the at least one body part 104 (e.g., region from which the amount of salt was detected). For example, the control system 912 can selectively direct the at least one TSDD 910 to initiate, terminate, or alter application of the radiation to the region of the at least one body part 104 responsive to a determination of a presence or absence of the activation condition, such as only if the sensed information indicates that the subject is not moving, is at rest, or has been at rest for a selected duration. The one or more threshold values can be found in look up tables stored in the memory storage medium. The one or more threshold values can include a threshold value (e.g., upper or lower bound(s)) or range for any characteristic of the at least one body part that is related to at least one of movement or a physiological state of the at least one body part, such as a safe or optimum level of the at least one characteristic.

The one or more activation conditions can be at least partially based on sensed information or values indicative of a muscle cramp, a muscle spasm, a muscle contraction, a level of one or more of oxygenation or blood flow, pulse, heart rate, presence or amount of a physiological analyte (e.g., lactic acid) or a derivative thereof, movement of the subject (or one or more selected body parts thereof) such as for a selected duration of time, lack of movement of the subject (or one or more selected body parts thereof) for a selected duration of time, one or more of an elapsed time since initiation of a level of movement of the subject (e.g., running or a selected heart rate), an elapsed time since termination of a level of movement of the subject, an elapsed time since termination of change of position of the subject, an elapsed time since termination of movement of the subject, that the subject is moving in a specific pattern indicative of a specific activity, after an elapsed time of the specific activity of the subject, after an elapsed time since termination of the specific activity of the subject, a presence of physiological indicators of pain, etc.

In an embodiment, the one or more threshold values can include the duration of an activity or inactivity indicative of a specific state or activity. For example, the control system 912 can include one or more threshold values for durations stored therein. The one or more threshold values can indicate a duration after which, or prior to, an activation condition is indicated. For example, a duration since a last detected movement or level of movement from a body part, movement commenced, or a level of movement (e.g., selected heartrate, or selected amount of motion of the at least one body part such as one or more limbs) commenced can be set as a threshold for an activation condition. Such durations can be at least 1 minute, such as 1 minute to about 8 hours, 5 minutes to about 6 hours, about 15 minutes to about 4 hours, about 30 minutes to about 3 hours, about 1 hour to about 2 hours, more than about 10 minutes, more than about 30 minutes, more than about 1 hour, more than about 2 hours. In an embodiment, an activation condition can be indicated by a threshold value of a duration since a last occurrence of movement of the subject. In such embodiments, a motion sensor can detect one or more of a motion of the subject (e.g., movement from one place to another), a motion of the at least one body part such as one or more limbs of the subject (e.g., arms and/or legs moving to indicate walking or running), a stationary condition of the subject (e.g., a duration after which a subject is considered to be stationary), a stationary condition of the at least one body part such as one or more limbs of the subject (e.g., a duration after which the one or more limbs of the subject are considered to be stationary), or a duration since a last occurrence of any of the foregoing. The control system 912 can determine if the duration of time since the last occurrence of any of the foregoing indicates that the activation condition is present, such as if operational instructions require a subject to be stationary prior to application of therapeutic radiation from the one or more TSDDs 910.

In an embodiment, the memory can include activity information stored thereon that indicate a selected activity is taking place or specific condition is present or absent based on the sensed information from one or more different sensors. In an embodiment, activity information can include one or more patterns of movement or physiological criteria that correlate to a specific activity. In such embodiments, the control electrical circuitry can compare the sensed information with the activity information and determine what activity is taking place. For example, a specific pattern of movement may be correlated to jogging or bicycling, or a selected duration of inactivity may be correlated with an inactive state or sleeping.

In an embodiment, the controller can include a timer (e.g., clock) to provide information indicative of a time of day or a duration of one or more of an elapsed time since an activity has commenced, an elapsed time since an activity as terminated, an elapsed time since application of the therapeutic ultrasonic radiation has commenced, an elapsed time since application of the therapeutic ultrasonic radiation in a specific region of the at least one body part has commenced, or an elapsed time since application of the therapeutic ultrasonic radiation has terminated.

In an embodiment, the controller can receive the sensed information and determine a presence of an indication of pain. For example, specific values or patterns of the characteristic(s) of the at least one body part that is related to at least one of movement or a physiological state of the at least one body part can indicate that a subject is in pain.

Pain can be attributed to numerous physiological and neurological conditions and can be experienced by an individual subject according to a variety of pain states. A pain state includes a pain type, a pain level, a pain quality, or combinations thereof. For example, the pain states can include a pain-free state, an onset of pain, a pain pattern, chronic pain, acute pain, mixed pain state, a hyperalgesic pain state, an allodynic pain state, a breakthrough pain state, a neuropathic pain state, a nociceptive pain state, a non-nociceptive pain state, combinations thereof, or the like. Pain types can include, for example, nociceptive pain (e.g., due to mechanical, thermal, and/or chemical interactions), somatic pain, neuropathic pain, visceral pain, superficial pain, and psychogenic pain, where various pain types can be experienced according to particularized biological systems or locations (e.g., musculoskeletal, neuropathic, etc.) or can be nonlocalized. For example, pain types can include spontaneous pain (e.g., occurring in the absence of stimuli), evoked pain (e.g., occurring in response to stimuli), continuous pain, or intermittent pain. For example, pain levels can include intensity, severity, or magnitude of pain. Pain quality can include, but is not limited to, intensity, sharpness, dullness, burning, cold, tenderness, itch, cramping, radiating, tingling, throbbing, aching, tiring, deepness, shocking or electrical, stinging, etc., and combinations thereof. Assessment tools to evaluate a pain state can, for example, include instruments or combinations of instruments and related software designed to monitor physiological responses including chemical changes, biopotentials, muscle activation, and changes thereof. Assessment tools to evaluate a pain state can, for example, include instruments or combinations of instruments and related software designed to monitor autonomic responses as described herein. Assessment tools to evaluate a pain state, for example, can include subjective tools such as the Pain Quality Assessment Scale and the McGill Pain Questionnaire. An individual threshold for a pain can be set (e.g., programmed into the control system 912) for a subject based on the foregoing, or other objective or subjective considerations.

Pain is prevalent in human and animal populations. Some examples can include a majority of the human population (60% to 85%) is reported to experience back pain of muscular origin at some point in their lifetime, pain evoked by myofascial trigger points is experienced by approximately 30% of the population, approximately 50 million Americans experience arthritis (such as osteoarthritis or inflammatory arthritis), and at least 30% of patients with moderate chronic pain and more than 50% of patients with severe chronic pain fail to achieve adequate pain relief. The costs associated with traditional treatment of pain and the lack of treatment of pain (e.g., lost wages, disability, medical facility costs, etc.) can be large and widespread.

In addition, pain and movement are intrinsically interrelated. Movement is known to be related to cause, effect, prevention, and therapy of pain and its disorders. The systems, devices, and methods described herein generate sensing signals from one or more sensors (e.g., physiological sensors and/or motion sensors) positioned proximate at least one body part of a subject to provide indicators of a physiological state (e.g., a pain state) of the subject.

In an embodiment, the presence of an indication of pain can be based on one or more of nerve signals indicative of pain (e.g., electrical signals), an amount of one or more chemicals in a fluid of the subject (e.g., salt(s), glucose, lactate, hormone(s), peptides, etc.), or a specific pattern of movement (e.g., movement indicating limping or favoring a limb, moving slower than a normal rate, moving in a different pattern than a normal pattern), or changes of any of the foregoing. For example, changes in levels of physiological chemicals can be associated with increased muscle use or the presence of a pain condition. For example, increases in lactate levels or in glucose levels (e.g., in response to released hormones), measurable in sweat or bodily tissues (e.g., interstitial tissues), can be associated with increased muscle use or the presence of pain. In an embodiment, increased levels of one or more hormones (e.g., cortisol, pregnenolone, DHEA, testosterone, progesterone, estrogen, T3, and T4) released in response to pain are measurable in sweat or other bodily fluids. In an embodiment, neuropeptides (e.g., neuropeptide Y, substance P and CGRP or other neurotransmitters (e.g., glutamate)) released in response to pain are measurable in sweat or other bodily fluids. Such measured or detected physiological analytes can be compared to threshold values (e.g., a base level not associated with pain), patterns, or combinations of physiological analytes to determine a presence or absence of an indication of pain. For example, the control system can determine if a chemical indication of pain is present based at least in part on a detected presence or change in concentration of one or more analytes as disclosed herein. For example, the presence of an amount of lactate in sweat over a threshold value can indicate that a subject is in pain. The control electrical circuitry can direct the at least one TSDD 910 to selectively deliver the therapeutic radiation responsive to a determination that the subject is exhibiting a presence of an indication of pain.

In an embodiment, the presence of an indication of pain may include reference data (e.g., stored in the control system 912) of physiological and biomechanical information pertaining to an acute or traumatic injury that can include a strain, a sprain, or a tear of a muscle or soft tissue (e.g., ligament, tendon, enthesis, or other connective tissue). The reference data may include physiological and biomechanical information pertaining to a long-term or chronic medical condition that can include a joint-based non-inflammation condition (e.g., arthralgia, osteo-arthritis), a joint-based inflammation condition (e.g., rheumatoid arthritis, psoriatic arthritis, arthritis, ankylosing spondylitis, juvenile idiopathic arthritis and systemic lupus erythematosus), an enthesis-based condition (e.g., enthesitis), a tendon-based condition (e.g., tendonitis, tenosynovitis), a ligament-based condition (e.g., chronic strain), a nerve entrapment or compression based condition or syndrome (e.g., carpal tunnel entrapment, cubital tunnel entrapment, tarsal tunnel entrapment, radial nerve entrapment, meralgia paresthetica), and the like. The control system 912 can correlate any of the above reference data, or physiological and biomechanical information therein pertaining to an acute or traumatic injury, or a long-term or chronic medical condition (stored in the control system (e.g., the memory)) to one or more sensed characteristics of the subject to determine a presence of an indication of pain (e.g., an acute injury or chronic medical condition).

Movement of the at least one body part 104 or characteristics thereof can be indicative of pain experienced by the individual. For example, the conscious or unconscious fear that a motion will induce pain can alter the motion of a body part, indicating acute or chronic pain. For example, physiological adaptation to acute pain or chronic pain can cause short-term or long-term changes in motor function of a body part (e.g., increased or inhibited muscle activation), and as such can be indicative of pain. Alterations in movement of a body part can present, for example, as pronounced minimalization of motion or agitation affecting a body site (e.g., a muscle), a guarding motion, an awkward gait, a limp, redistribution of activity or stress, modifications in loading, pronounced use of non-dominant limb, reduced force output, lack of use of a body part, etc. For example, conscious or unconscious coping mechanisms (e.g., pronounced rubbing or massage of a body portion, etc.) can be indicative of pain. For example, involuntary responses (e.g., reflex, spasm, etc.) can be indicative of pain. In an embodiment, movement of the body part of the individual can be a source of, a cause of, or induce or worsen pain, and, as such, a particular movement can be determined to be associated with the pain. For example, a certain motion can be repeatedly associated—temporally—with an increase in pain (e.g., as indicated by changes in autonomic responses, measured by chemical sensors, electrophysiological sensors, biopotential sensors, etc. or by subjective reporting). In an embodiment, the one or more sensors can detect any of the above characteristics and the control system 912 can determine the presence of an indication of pain by comparing the detected movement to one or more known movements associated with pain (e.g., a limp, favoring an arm, etc.) stored therein.

The control electrical circuitry (e.g., processing electrical circuitry) can selectively direct the at least one TSDD 910 to initiate, terminate, or alter application of the therapeutic radiation to the region responsive to a determination that an activation condition is present or responsive to an instruction entered into the control system 912 via a user interface (e.g., a manual activation or shut off). The control system 912 can be operably coupled to the at least one TSDD 910 and can direct the at least one TSDD 910 to selectively apply radiation (e.g., therapeutic ultrasonic radiation) to a region of the at least one body part 104. The control electrical circuitry can direct the at least one TSDD 910 to selectively apply radiation to the region of the at least one body part responsive to the one or more sensing signals 109.

In an embodiment, the at least one TSDD 910 can be individually adjustable to be aimed (e.g., steerable), such as responsive to aiming instructions from the control system 912 (e.g., controller), a pre-programmed routine, or instructions from a remote control or computer. In an embodiment, the at least one TSDD 910 can include a plurality of steerable TSDDs each of which is individually adjustable to be aimed at to one or more portions of the at least one body part 104 of the subject 106, such as responsive to aiming instructions. The individually adjustable TSDDs can adjust automatically based on one or more aiming instructions. For example, the at least one TSDD 910 can include at least one (e.g., a plurality of) steerable therapeutic ultrasound transducer, which can be selectively aimed to emit therapeutic ultrasonic radiation. The aiming instructions can direct the at least one TSDD 910 to apply radiation to a region in which the one or more sensors 108 provide data that the controller determines indicates that an activation condition is present. The aiming instructions can be included in operational instructions. For example, the control system 912 can direct the therapeutic ultrasonic transducer to aim the therapeutic ultrasonic radiation to a specific portion of the region of the at least one body part 104 responsive to sensor information detected by the scanning acoustic transducer. The one or more sensors can include a plurality of sensing acoustic transducers configured to emit scanning ultrasonic radiation to the specific portion of the region of the at least one body part 104. In an embodiment, the control electrical circuitry can determine a location to direct the therapeutic ultrasonic radiation from the plurality of steerable therapeutic ultrasonic transducers, based at least in part on reflected acoustic radiation (e.g., indicating one or more activation conditions at the location). For example, the control electrical circuitry can identify soft tissue from the reflected acoustic radiation, and direct the plurality of steerable therapeutic ultrasonic transducers to emit the therapeutic ultrasonic radiation toward the soft tissue (e.g., focus therapeutic ultrasonic radiation from a plurality of steerable therapeutic ultrasonic transducers at a single point or region).

In an embodiment, the control electrical circuitry can independently direct at least one of the plurality of steerable therapeutic ultrasonic transducers to aim the therapeutic ultrasonic radiation therefrom to a first region of the at least one body part and at least some of the plurality of steerable therapeutic ultrasonic transducers to aim the therapeutic ultrasonic radiation therefrom to at least a second region of the at least one body part, responsive to sensor information detected by the plurality of sensors 108, 108', or 108" (e.g., sensing acoustic transducers).

In an embodiment, the control electrical circuitry can cause the at least one TSDD to terminate or adjust application of the radiation responsive to one or more sensing signals collected at the one or more sensors during the application of the radiation. For example, the one or more sensing signals collected during application of the radiation can include the temperature of the region in which the therapeutic radiation is applied. Such dynamic control is described in more detail below.

In an embodiment, the one or more operational programs or threshold values can be entered into the memory via the user interface of the control system 912. The user interface can be similar or identical to any user interface disclosed herein, such as user interface 622. In an embodiment, the user interface can include a display to communicate (e.g., provide visual and/or audio indications) to the user that one or more of an activation condition has been detected, a threshold level has or has not been detected, initiation of application of the radiation is imminent, termination of application of radiation is imminent, an amount of the radiation that will be applied to the region, a current amount of the radiation being applied to the region, an amount of time left for an operational program or currently applied radiation, an amount of time left before application of the radiation, or one or more controls for refusing, terminating, adjusting, or initiating application of the radiation. In an embodiment, the user interface can be configured to accept input from a user that identifies when a subject is in pain (or a level of said pain), and the sensors can detect one or more characteristics at that time and correlate the sensed information with a pain state or presence of an indication of pain for later reference. Such information can be stored in the memory.

The garment system 900 can include one or more compression actuators (FIGS. 1-4) operably coupled to the control system 912 (e.g., controller). The one or more compression actuators can be positioned relative to the at least one flexible compression garment 902, and configured to cause a portion of at least one flexible compression garment 902 to selectively compress against or selectively relieve compression against the at least one body part 104, such as in an intermittent pattern (e.g., peristaltic motion having a massaging effect). In such embodiments, the control system is configured to cause the one or more compression actuators to selectively compress against or selectively relieve compression against the at least one body part 104, responsive to one or more sensing signals indicative of the at least one characteristic, a pre-programmed routine, or a direction from a remote control or computer. The one or more actuators can be operated while the at least one TSDD 910 is applying therapeutic radiation, the one or more sensors 108, 108', or 108" are sensing the one or more characteristics, while the at least one TSDD 910 is not applying therapeutic radiation, or the one or more sensors 108, 108', or 108" are not sensing the one or more characteristics. For example, the one or more actuators can be operated prior to or after application of therapeutic radiation. Operational instructions can include executable instructions for actuating the one or more actuators, controlling the one or more TSDDs 910, and controlling the one or more sensors 108, 108', or 108". In an embodiment, the operational instructions and the control system can to synchronize an intermittent pattern of actuation of the compression actuators with blood flow in the at least one body part 104.

Figure 10A:
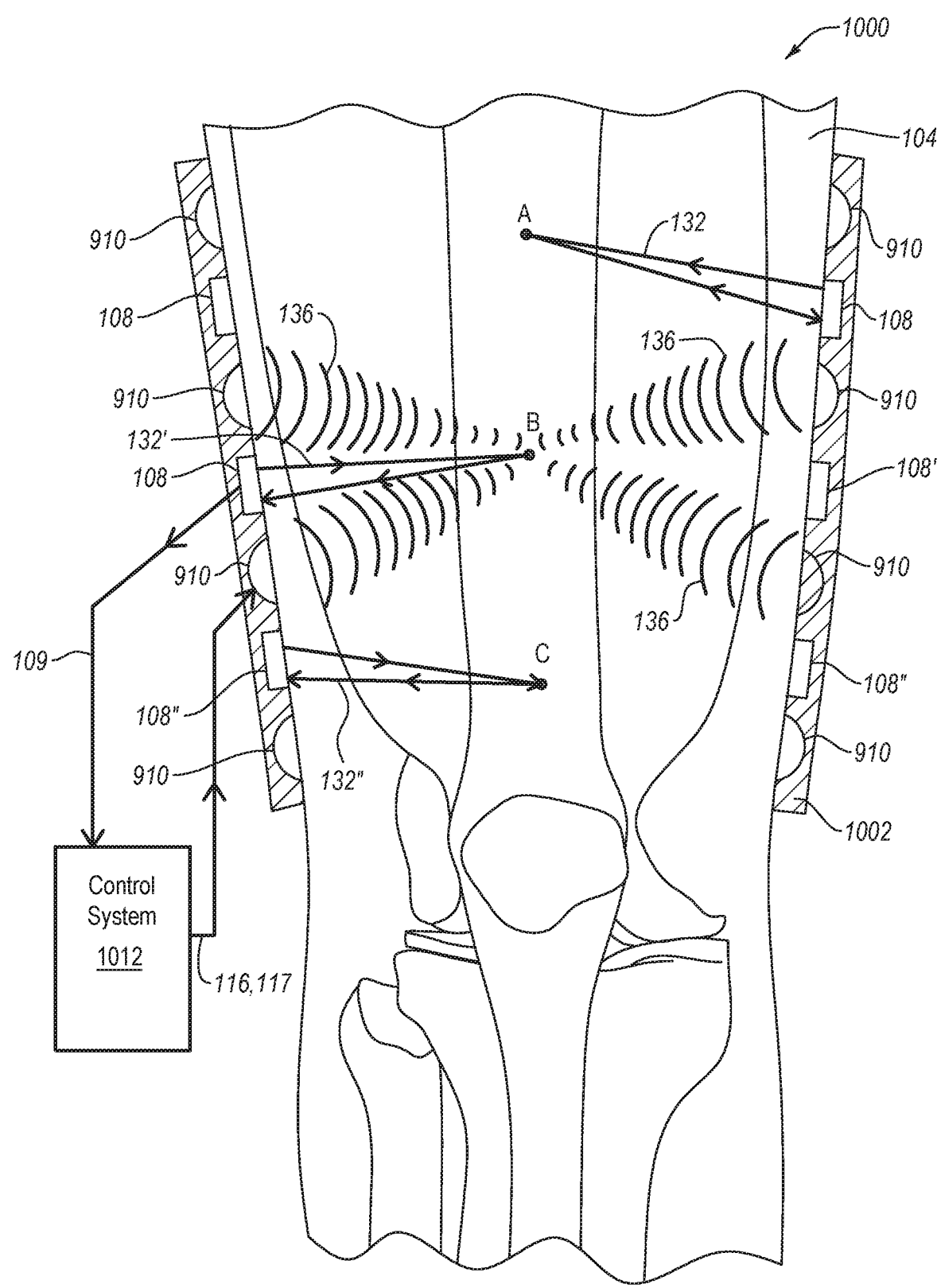
FIGS. 10A and 10B are partial cutaway views of a garment system including a flexible compression garment worn on a leg of a subject at different points during use, according to an embodiment.
Figure 10B:
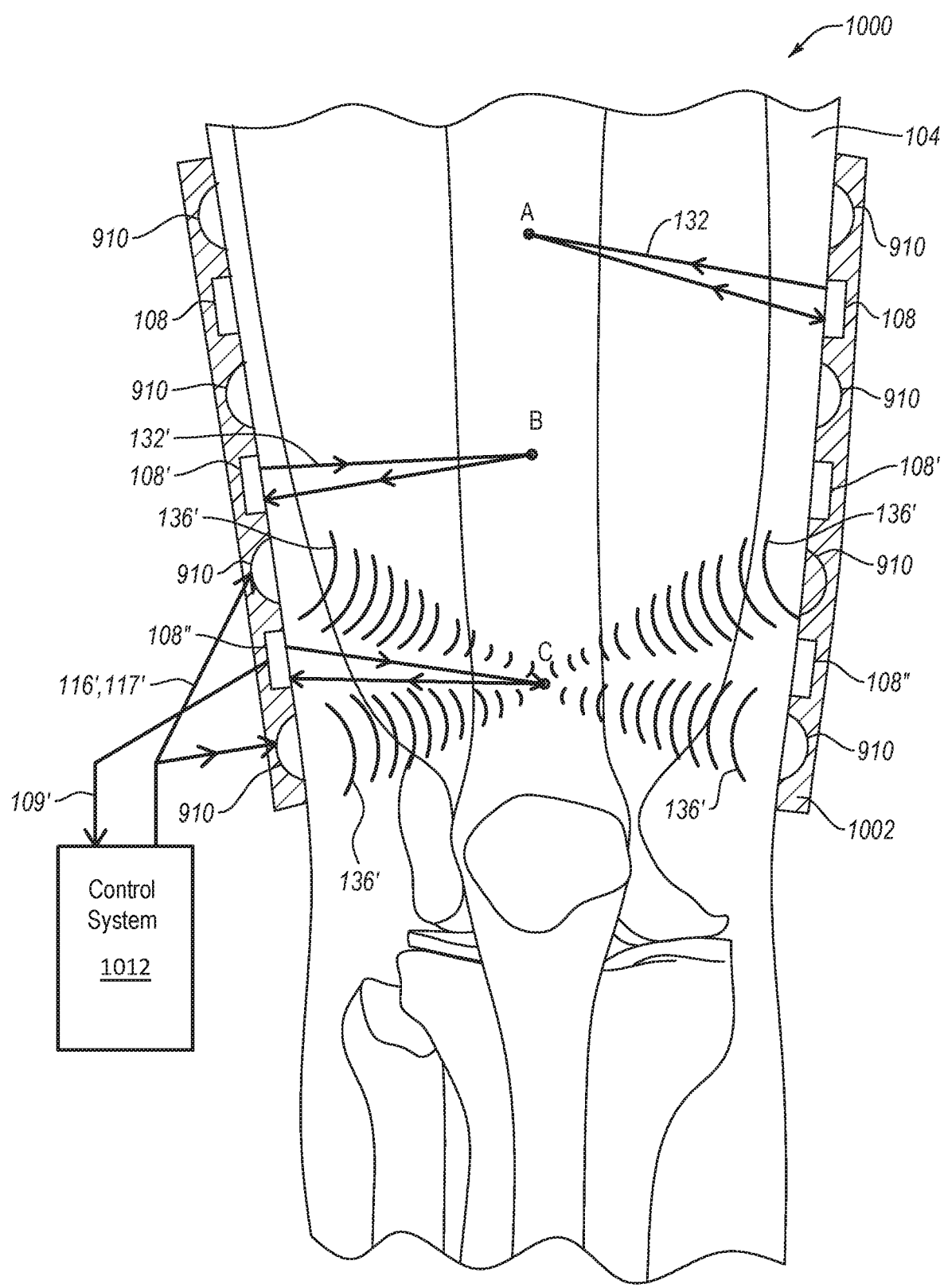

FIGS. 10A and 10B are partial cutaway views of a garment system 1000 including a flexible compression garment 1002 worn on at least one body part 104 (e.g., a leg) of a subject at different points during use, according to an embodiment. The garment system 1000 can dynamically apply (e.g., adjust during application) therapeutic radiation to at least one body part 104 using an array of TSDDs and one or more sensors, such as to detect an effect of the therapeutic radiation. FIG. 10A depicts the garment system 1000 at a first point during use, and FIG. 10B depicts the garment system 1000 at a second, subsequent point during use.

The garment system 1000 can include at least one flexible compression garment 1002, which may be similar or identical to any flexible compression garment disclosed herein (e.g., flexible compression garment 902), in one or more aspects. The garment system 1000 can include one or more sensors 108, 108', or 108", which may be similar or identical to any sensors disclosed herein, in one or more aspects. For example, the one or more sensors 108, 108', or 108" can sense (e.g., detect) at least one characteristic of the at least one body part that is related to at least one of movement or a physiological state of the at least one body part, the one or more sensors can also output one or more sensing signals 109 indicative of the at least one characteristic. The garment system 1000 can include one or more TSDDs 910, such as an array of TSDDs 910 as shown, any of which may be similar or identical to any TSDDs disclosed herein, in one or more aspects. The array of TSDDs 910 can be positioned to apply therapeutic radiation to the at least one body part 104, such as dynamically (e.g., changing a focal point thereof and/or having changing characteristics such as frequency, intensity, or wavelength, during application of the radiation) responsive to one or more sensing signals 109 or 109' sent during application of the therapeutic radiation. The garment system 1000 can include a control system 1012 similar or identical to any of the control systems disclosed herein (e.g., 612 or 912), in one or more aspects. The control system 1012 (e.g., controller) can be operably coupled to the one or more sensors 108, 108', or 108" to receive the one or more sensing signals therefrom and the one or more (e.g., array of) TSDDs 910. The control system 1012 includes control electrical circuitry configured to direct the one or more (e.g., array of) TSDDs 910 to dynamically apply the therapeutic radiation to a region of the at least one body part 104 responsive to one or more sensing signals. The control system 1012 includes a memory configured to store sensing information, threshold values, operational instructions, therapeutic radiation emission history, or any other information related to the subject or the garment system 1000. A power supply can be operably coupled to any components of the garment system 1000 and/or control system 1012 thereof to provide power to the components. In an embodiment, the power supply can be disposed in or on the at least one flexible compression garment 1002, or the power supply can be remote from the at least one flexible compression garment 1002, such as on a separate wearable device.

The one or more sensors 108, 108', or 108" can detect the at least one characteristic of the at least one body part 104 that is related to at least one of movement or a physiological state of the at least one body part as disclosed herein, such as at least one of nerve activity of at least tissue in the region, an internal temperature of the region, an external temperature, blood flow in the region, tissue oxygenation in the region, a strain on the at least one body part, a conductance in the region, an impedance in the region, a pH in a body fluid in the region, a chemical composition of a physiological analyte in the region, an acoustic emission from tissue in the region, biochemical activity in the region, motion of the subject, motion of one or more the at least one body part such as limbs of the subject, a stationary condition of the subject, or a stationary condition of the at least one body part such as one or more limbs of the subject, changes of any of the foregoing exceeding a threshold value, or occurrence or cessation of any of the foregoing for a duration longer than a selected duration of time. For example, the one or more sensors 108, 108', or 108" can sense characteristics indicative of an onset of muscle activity, muscular fatigue, a conclusion of muscle activity, a threshold level of muscle activity in the region, or one or more indications of pain (e.g., elevated lactate levels in sweat or body tissues).

The one or more sensors 108, 108', or 108" can include at least one sensing ultrasound transducer configured to emit sensing ultrasonic radiation 132 to a region of the at least one body part, and the control system 1012 can independently direct each of an array of therapeutic ultrasound transducers to aim at a specific portion of the region responsive to sensor information detected by the at least one sensing ultrasound transducer, a pre-programmed routine, or a direction from a remote control or computer. In an embodiment, the plurality of sensing ultrasound transducers can scan the at least one body part 104 such as in a first and second region thereof with sensing ultrasound radiation during application of therapeutic ultrasonic radiation, such as to monitor (e.g., detect) the at least one characteristic associated with movement or the at least one characteristic of a region the at least one body part.

The one or more sensors 108, 108', or 108" can be positioned to actively scan (e.g., sense or detect) the at least one body part 104 for the at least one characteristic or additional characteristics during application of therapeutic radiation (e.g., therapeutic ultrasound radiation) to the at least one body part 104. For example and as shown in FIG.

10A, a first set of sensors 108 can scan a region or point A such as with scanning acoustic radiation 132 and receive one or more sensing signals 109 (e.g., reflected scanning acoustic radiation) responsive thereto. A second set of sensors 108' can scan a region or point B such as with scanning acoustic radiation 132' and receive one or more sensing signals 109 responsive thereto. A third set of sensors 108" can scan a region or point C such as with scanning acoustic radiation 132" and receive one or more sensing signals 109 responsive thereto. The sensing signals 109 can be provided to the control system 1012. Responsive to the sensing signals 109, which may include sensing information of the at least one characteristic (e.g., characteristics indicative of onset of muscle activity, muscular fatigue, a conclusion of muscle activity, passage of a duration of time since an activity or level thereof, a threshold level of muscle activity in the region, or an indication of pain), the control system 1012 can direct the at least one TSDD 910 (e.g., at least one array of TSDDs) to selectively initiate, terminate, or alter application of the therapeutic radiation to the at least one body part 104, such as via one or more actuation signals 116 transmitted from the at least one TSDD from the control system 1012. For example, one or more sensing signals 109 can include sensing information that the control system 1012 determines indicates at least one characteristic that meets, exceeds, or falls short of a threshold value for the at least one characteristic. Such sensing signals 109 can be collected and transmitted to the control system 1012 during application of therapeutic radiation, and the control system 1012 can direct the at least one TSDD 910 to selectively initiate, terminate, or alter application of the therapeutic radiation to the at least one body part 104 via the one or more actuation signals 116. As shown, the sensing information collected by the (e.g., scanning acoustic radiation 132') can be relayed to the control system 1012 via the sensing signal 109. The control system 1012 can determine if an activation condition is present based on the sensing information in the sensing signal 109, such as by comparison to one or more threshold values stored therein.

As shown in FIG. 10A, the sensing information in sensing or scanning acoustic radiation 132 can indicate that an activation condition is not present at point A, while the sensing information in scanning acoustic radiation 132' can indicate that an activation condition is present at point B. Responsive to the indication of an activation condition, the control system can cause at least some of the plurality of TSDDs 910 (e.g., one or more arrays of TSDDs adjacent to point B) to selectively emit therapeutic radiation to point B (e.g., emit therapeutic ultrasonic radiation to point B or focus one or more of the array of TSDDs to point B). In an embodiment, the one or more sensors can be at least partially disposed in an interior space defined by the interior surface of the flexible compression garment. In an embodiment, the one or more sensors can be at least partially disposed on or in the at least one flexible compression garment (e.g., between one or more layers of the flexible compression garment). In an embodiment, at least one of the one or more sensors 108, 108', or 108" can be disposed remotely from the at least one flexible compression garment 1002, such as disposed on a wall, a room scanner, or a motion capture device.

In an embodiment, the one or more sensors 108, 108', or 108" can scan the region or focal point into which the therapeutic radiation is emitted or focused (or one or more different regions thereof), while the therapeutic radiation is emitted or focused in the region or focal point. In such embodiments, the one or more sensors 108, 108', or 108" can detect one or more of a change in the at least one characteristic, a steady state of the at least one characteristic, or a different at least one characteristic, and relay additional sensing information (e.g., via one or more sensing signals 109) indicating the same to the control system 1012. Responsive to receiving the additional sensing information, the control system (e.g., controller) can determine if the sensing information indicates that the activation condition is still present, a new activation condition is present, or if the application of therapeutic radiation from the one or more TSDDs 910 should be initiated (e.g., in a different region or a different type of therapeutic radiation), terminated, or altered (e.g., increase or decrease a frequency, intensity, wavelength, or duration). For example, the control system 1012 can determine if a duration (e.g., an activation condition) has been reached, which duration can include one or more of a duration of time since application of the therapeutic radiation has commenced, a duration of time since application of the therapeutic radiation was last administered, a duration of time since a specific level of movement terminated, or a duration of time since a specific level or type of movement commenced. Such determinations can be based on the control electrical circuitry comparing the one or more threshold values for the at least one characteristic to the sensed at least one characteristic as disclosed herein. The therapeutic radiation being applied can be altered or terminated based on the determination by the control system, all while therapeutic radiation is being applied.

The control system 1012 can cause the plurality of TSDDs 910 to stop emitting a first therapeutic radiation (e.g., first frequency of therapeutic ultrasonic radiation) and emit at least a second therapeutic radiation (e.g., second frequency of therapeutic ultrasonic radiation). The at least a second therapeutic radiation can be the same as the first therapeutic radiation in one or more aspects, or can differ from the first therapeutic radiation in one or more aspects, such as type (e.g., ultrasonic, infrared, etc.), frequency, intensity, wavelength, duration, pulse duration, etc. In an embodiment, the control system 1012 can cause at least a second plurality (e.g., array) of TSDDs emit at least a second therapeutic radiation, such as in addition to the first therapeutic radiation. For example, the control system 1012 can change the first therapeutic radiation to at least a second therapeutic radiation effective to penetrate the tissue of the subject to a different depth than the first of wavelength, frequency, or intensity of the first therapeutic radiation.

In an embodiment, the garment system 1000 can include at least one array of TSDDs 910 (e.g., two or more arrays of TSDDs, three or more arrays of TSDDs, four or more TSDDs, or less than 10 arrays of TSDDs), and the control system 1012 can be operably coupled to each array of the at least one array of TSDDs 910. In an embodiment, the array of TSDDs 910 can include an array of ultrasound transducers, each of which can apply therapeutic ultrasonic radiation to the at least one body part 104. In such embodiments, each ultrasound transducer of the of the array of ultrasound transducers can apply therapeutic ultrasonic radiation to the at least one body part effective to control (e.g., alter or maintain) one or more of a temperature of at least a region of the at least one body part, block one or more nerve signals, administer a medicament, or activate a medicament.

In an embodiment, the one or more sensors 108, 108', or 108" can include at least one sensing ultrasound transducer configured to apply sensing ultrasonic radiation to tissue of the at least one body part 104 and receive reflected sensing ultrasonic radiation responsive thereto. The array of TSDDs 910 can include an array of therapeutic ultrasound transducers configured to apply therapeutic ultrasonic radiation to the at least one body part 104. In such embodiments, each of the at least one sensing ultrasound transducers and at least one of the array of therapeutic ultrasound transducers includes a multipurpose ultrasound transducer configured to selectively emit both sensing ultrasonic radiation and therapeutic ultrasonic radiation (e.g., both low and high frequency ultrasonic radiation).

The control system 1012 can selectively control any of the arrays of TSDDs, such as while any of the other arrays of TSDDs are emitting therapeutic radiation. In an embodiment, one or more of the at least one TSDD can be selectively aimable, such as a steerable TSDD as described herein. The control system 1012 can direct the steerable TSDDs to aim or focus to a selected region or focal point, responsive to the sensing signals sent during application of the therapeutic radiation. For example, each ultrasound transducer of the of the array of ultrasound transducers can apply the therapeutic ultrasonic radiation to a common region in the at least one body part effective to control a temperature of the common region, collectively block one or more nerve signals, administer a medicament, or activate a medicament, responsive to one or more directions from the control system 1012. In an embodiment, at least one TSDD 910 (e.g., ultrasound transducer) of the array of TSDDs (e.g., ultrasound transducers) can emit the therapeutic (e.g., ultrasonic) radiation to a first region of the at least one body part 104 and at least another TSDD 910 (e.g., ultrasound transducer) of the array of TSDDs (e.g., ultrasound transducers) can emit therapeutic (e.g., ultrasonic) radiation to at least a second region of the at least one body part 104. In such embodiments, the first region can be laterally and/or vertically spaced from the at least a second region, such as being farther into the tissue of the at least one body part than the second region.

In an embodiment, the at least one ultrasound transducer of the array of ultrasound transducers can emit a first therapeutic ultrasonic radiation having one or more of a first wavelength, a first frequency, or a first intensity and at least another ultrasound transducer of the array of ultrasound transducers can emit one or more of at least a second therapeutic ultrasonic radiation having at least a second wavelength, at least a second frequency, or at least a second intensity differing from one or more of the first wavelength, the first frequency, or the first intensity. In an embodiment, the first frequency can be selected so that the first therapeutic ultrasonic radiation penetrates to a first depth in the at least one body part and the at least a second frequency is selected so that the at least a second therapeutic ultrasonic radiation penetrates to a second depth in the at least one body part, wherein the first depth and the second depth are different. The control system 1012 can control the first ultrasound transducer and the at least another transducer to selectively initiate, maintain, terminate, or alter one or more of the wavelength, frequency, or intensity of ultrasonic radiation, which may be responsive to determination of an activation condition as described above, a pre-programmed routine, or direction from a remote control or computer. In embodiments, at least one of the array of ultrasound transducers can emit a first therapeutic ultrasonic radiation having one or more of a first wavelength, a first frequency, or a first intensity, and subsequently the at least one of the array of ultrasound transducers can emit at least a second therapeutic radiation including one or more of the second wavelength, the second frequency, or the second intensity One or more of the at least one TSDD 910 can be equipped to emit low frequency (e.g., ultrasonic) radiation, high frequency (e.g., ultrasonic) radiation, a plurality of frequencies of (e.g., ultrasonic) radiation, low intensity (e.g., ultrasonic) radiation, high intensity (e.g., ultrasonic) radiation, any wavelength of (e.g., ultrasonic) radiation, a plurality of pulses of (e.g., ultrasonic) radiation, or a constant stream of (e.g., ultrasonic) radiation. For example, the at least one TSDD (e.g., ultrasound transducer) of the array of TSDDs (e.g., ultrasound transducers) configured to selectively emit one or more wavelengths, frequencies, or intensities of the therapeutic (e.g., ultrasonic) radiation is configured to adjustably increase or decrease the one or more wavelengths, frequencies, or intensities during application of the therapeutic radiation to the at least one region responsive to one or more actuation signals 116. One or more of the TSDDs can be configured to emit acoustic radiation such as therapeutic ultrasonic radiation, either continuously or in a plurality of pulses of acoustic radiation.

In an embodiment, the array of TSDDs can include one or more of at least one electrode, at least one magnetic field generator, at least one optical stimulator, at least one thermal control device, or at least one microwave emitter.

In an embodiment, at least one TSDD of the array of TSDDs can include at least one steerable TSDD (e.g., steerable ultrasound transducer), which can be aimed to a selected portion of the at least one body part 104 responsive to aiming instructions 117 delivered from the control system 1012 such as in operating instructions (e.g., actuation signals 116). In such embodiments, the aiming instructions 117 are configured to direct the at least one TSDD (e.g., ultrasound transducer) to aim therapeutic (e.g., ultrasonic) radiation to a region in which the one or more sensors 108, 108', or 108" provide data that the control system 1012 determines indicates an activation condition is present. In an embodiment, at least one steerable TSDD (e.g., ultrasound transducer) of an array of TSDDs can include a multi-element array wherein at least some elements of the multi-element array are oriented toward selected focal points and are individually and selectively controllable to deliver the therapeutic radiation to the selected focal point(s). In an embodiment, the at least one steerable TSDD can include a mechanically steerable TSDD such as an ultrasound transducer (e.g., a mechanically steerable ultrasound transducer) mounted on a mechanically steerable base, which may be selectively steerable to aim the ultrasonic radiation to a selected focal point or region.

In an embodiment, responsive to sensing one or more characteristics during application of therapeutic radiation, a pre-programmed routine, or a directions from a remote control or computer; the control system 1012 can send one or more aiming instructions 117 to the at least one of the array of ultrasound transducers to aim the at least one ultrasound transducer of the array of ultrasound transducers to a different region, or send one or more actuation signals 116 effective to terminate application of the therapeutic ultrasonic radiation or alter one or more of wavelength, frequency, or intensity of the therapeutic ultrasonic radiation.

In an embodiment, the control system 1012 (e.g., control or processing electrical circuitry therein) is programmed to determine if an activation condition is indicated by comparing the sensed information with one or more threshold levels stored in the memory storage medium corresponding to the sensed information, and determine if the sensed information exceeds the one or more threshold levels. Responsive to a determination of a presence or absence of the activation condition (determined from by the sensed information), the control system 1012 (e.g., control electrical circuitry) can selectively direct the array of therapeutic ultrasound transducers to initiate, terminate, or alter application of the therapeutic ultrasonic radiation to the region. The activation condition can include any of the activation conditions described herein. For example, the activation condition can include one or more of a level of oxygenation in the at least one body part, blood flow in the at least one body part, pulse in the at least one body part, heart rate, presence of lactic acid, or amount of lactic acid, movement of the subject, a stationary condition of the subject, an elapsed time since initiation of a threshold level of movement of the subject, an elapsed time since termination of a threshold level of movement of the subject; an elapsed time since termination of change of position of the subject, an elapsed time since termination of movement of the subject, a level motion of the subject above a threshold level of motion, a level of motion of the at least one body part such as one or more limbs of the subject above a threshold level of motion of the at least one body part such as one or more limbs of the subject, a level of motion below a threshold level of a stationary condition of the subject, a level of motion of the at least one body part such as one or more limbs of the subject below a threshold level of a stationary condition of the at least one body part such as one or more limbs of the subject, or a duration since a last occurrence of any of the foregoing beyond a respective threshold amount. In an embodiment, the activation condition can be indicated (e.g., selective control of the TSDDs can be initiated) only if the at least one characteristic only if the sensed information indicates that the subject is not moving or at rest, only if the sensed information indicates that the subject is moving in a specific pattern indicative of a specific activity, only after an elapsed time of the specific activity of the subject, or only after an elapsed time since termination of the specific activity of the subject, or only if there is a presence of an indication of pain, such as any of those disclosed herein.

As shown in FIG. 10A, responsive to sensing at least one characteristic with the second set of sensors 108', such as via the scanning acoustic radiation 132', the sensing signals 109 can be relayed to the control system 1012. The control system 1012 can determine if the sensing signal 109 indicates that an activation condition is present and send one or more actuation signals 116 and/or aiming instructions 117 (e.g., aiming signals) to at least some of the one or more TSDDs. The actuation signals 116 can be transmitted to one or more of the TSDDs 910, such as the TSDDs 910 adjacent to the region in which the scanning acoustic radiation 132' was transmitted effective to cause the one or more TSDDs to emit therapeutic acoustic radiation 136 (e.g., increase, decrease, or alter) to the region. For example, the TSDDs 910 adjacent to point B can be selectively activated by actuation signals 116. In an embodiment, the aiming instructions 117 can be relayed to one or more steerable TSDDs effective to cause the one or more steerable TSDDs to aim the therapeutic radiation emitted therefrom (and/or increase, decrease, or alter the radiation therefrom) toward the region.

One or more sets of the sensors 108, 108', and 108" can continuously or intermittently sense (e.g., scan) the at least one body part 104, such as at points A, B, and/or C, during application of therapeutic radiation to the at least one body part 104 at point B.

As shown in FIG. 10A, the set of sensors 108" can collect sensing information (e.g., infrared radiation, electrical signals, physiological analytes, acoustic emissions, scanning acoustic radiation 132", etc.) from the region adjacent to point C, while the therapeutic radiation is applied to the at least one body part at point B. At least some of the scanning acoustic radiation 132" applied to point C can be reflected back to the sensor 108". The scanning acoustic radiation 132" can be transmitted to the control system 1012 via the sensing signal 109'. The control system 1012 can determine that an activation condition is present at the point C using the sensing information in the sensing signal 109', and direct one or more TSDDs 910 adjacent to point C to initiate, terminate, or alter application of therapeutic radiation (e.g., therapeutic acoustic (e.g., ultrasonic) radiation 136') thereto.

As shown in FIG. 10B, the control system 1012 can provide one or more actuation signals 116' and/or aiming instructions 117' (e.g., aiming signals) to the TSDDs. The one or more actuation signals 116' can be selectively sent from the control system 1012 to one or more TSDDs (e.g., ultrasound transduces or an array thereof) adjacent to the point C to apply therapeutic radiation (e.g., therapeutic acoustic radiation 136', such as ultrasonic radiation) thereto. In an embodiment, the aiming instructions 117' can be relayed to one or more steerable TSDDs effective to cause the one or more steerable TSDDs to aim the therapeutic radiation emitted therefrom (and/or increase, decrease, or alter the radiation therefrom) toward the point C or region thereabout. In an embodiment, the TSDDs 910 can be selectively directed by the control system 1012 (according to operational instructions stored therein) to the adjust (e.g., initiate, increase decrease, terminate) or maintain the therapeutic radiation applied, during application of the therapeutic radiation and responsive to one or more sensing signals indicating that an activation is present, a pre-programmed routine (e.g., specific sequence of therapeutic radiation application characteristics), or direction from a remote control or computer. In such a manner, the garment system 1000 can dynamically apply therapeutic radiation (e.g., therapeutic ultrasonic radiation) to at least one body part 104. The one or more sensors 108, 108', or 108" can continuously or intermittently sense for the at least one characteristic in the at least one body part while the therapeutic radiation is being applied to provide dynamic monitoring and control of the at least one body part 104, TSDDs 910, and therapeutic radiation emitted therefrom.

During application of therapeutic radiation, the one or more sensors 108, 108', or 108" can sense (e.g., scan) the one or more characteristics in the region that the therapeutic radiation is directed. The control system 1012 can determine that that the activation condition is no longer present or a different activation condition is present in the region (e.g., point B) and direct the one or more TSDDs 910 to terminate, initiate, or alter application of therapeutic radiation to the region in the at least one body part 104, and/or initiate, terminate, or alter application of therapeutic radiation to one or more additional regions of the at least one body part 104. Accordingly, the dynamic scanning and control can additionally or alternatively be based on sensed information from the region to which the therapeutic radiation is being applied. The control system 1012 can selectively direct application of therapeutic radiation to a plurality of regions (e.g., points A, B, and C) of the at least one body part 104 or multiple body parts, such as simultaneously, sequentially, randomly, or in patterns (e.g., according to an operational instruction).

In an embodiment, the garment system 1000 can include one or more compression actuators, such as any of those disclosed herein, to cause a portion of the at least one flexible compression garment 1002 to selectively compress against or selectively relieve compression against the at least one body part 104. The control system 1012 can cause the one or more compression actuators to selectively compression against or release compression against the at least one body part (e.g., in an intermittent pattern), such as responsive to one or more sensing signals 109 and/or operational instructions (e.g., encompassed in an actuation signal 116). In an embodiment, the control system 1012 can synchronize an intermittent pattern of compression and/or release of compression with blood flow, heart rate, a motion (e.g., muscle tension), etc. in the at least one body part.

In some embodiments, the garment system 1000 can include one or more sensors 108, 108', or 108" positioned and equipped to sense at least one characteristic of the at least one body part 104 that is related to at least one of movement or a physiological state of the at least one body part 104, the one or more sensors 108, 108', or 108" further configured to output one or more sensing signals to the control system 1012 indicative of the at least one characteristic. The garment system 1000 can include an array of steerable ultrasound transducers positioned and configured to selectively and dynamically apply therapeutic ultrasonic radiation to one or more selected regions of the at least one body part 104. The garment system 1000 can include the control system 1012 operably coupled to the one or more sensors 108, 108', or 108" to receive the one or more sensing signals therefrom and can be operably coupled to the array of steerable ultrasound transducers. The control system 1012 can include control electrical circuitry (e.g., processing electrical circuitry or a processor) configured to direct the array of steerable ultrasound transducers to selectively aim and emit radiation to the one or more selected regions of the at least one body part 104 responsive to one or more sensing signals (e.g., having sensed information that the control system 1012 determines is an indication of a presence or absence of an activation condition), a pre-programmed routine, or direction from a remote control or computer. The control system 1012 can include a memory (e.g., memory storage medium) operably coupled to the control electrical circuitry, the memory having one or more machine readable programs (e.g., operating instructions) stored therein, wherein the control electrical circuitry can execute the one or more machine-readable programs. The garment system can include a power supply operably coupled to the control system 1012, the one or more sensors, and the array steerable of ultrasound transducers.

In an embodiment, the garment system 1000 can include at least one medicament delivery device operably coupled to the controller and configured to provide topical, transdermal, or intramuscular medicament delivery to the at least one body part, such as any of those disclosed herein. The control system 1012 (e.g., controller) can be programmed to selectively control the one or more compression actuators and/or the at least one medicament delivery device to selectively compress or relieve compression against the at least one body part or to selectively deliver the at least one medicament in the at least one medicament delivery device. For example, the control system 1012 is configured to cause the at least one medicament delivery device to selectively deliver the at least one medicament, responsive to an elapsed duration or time of day. In an embodiment, the elapsed duration can include duration since the selected level actively commenced or the selected level of activity terminated.

Figure 11:
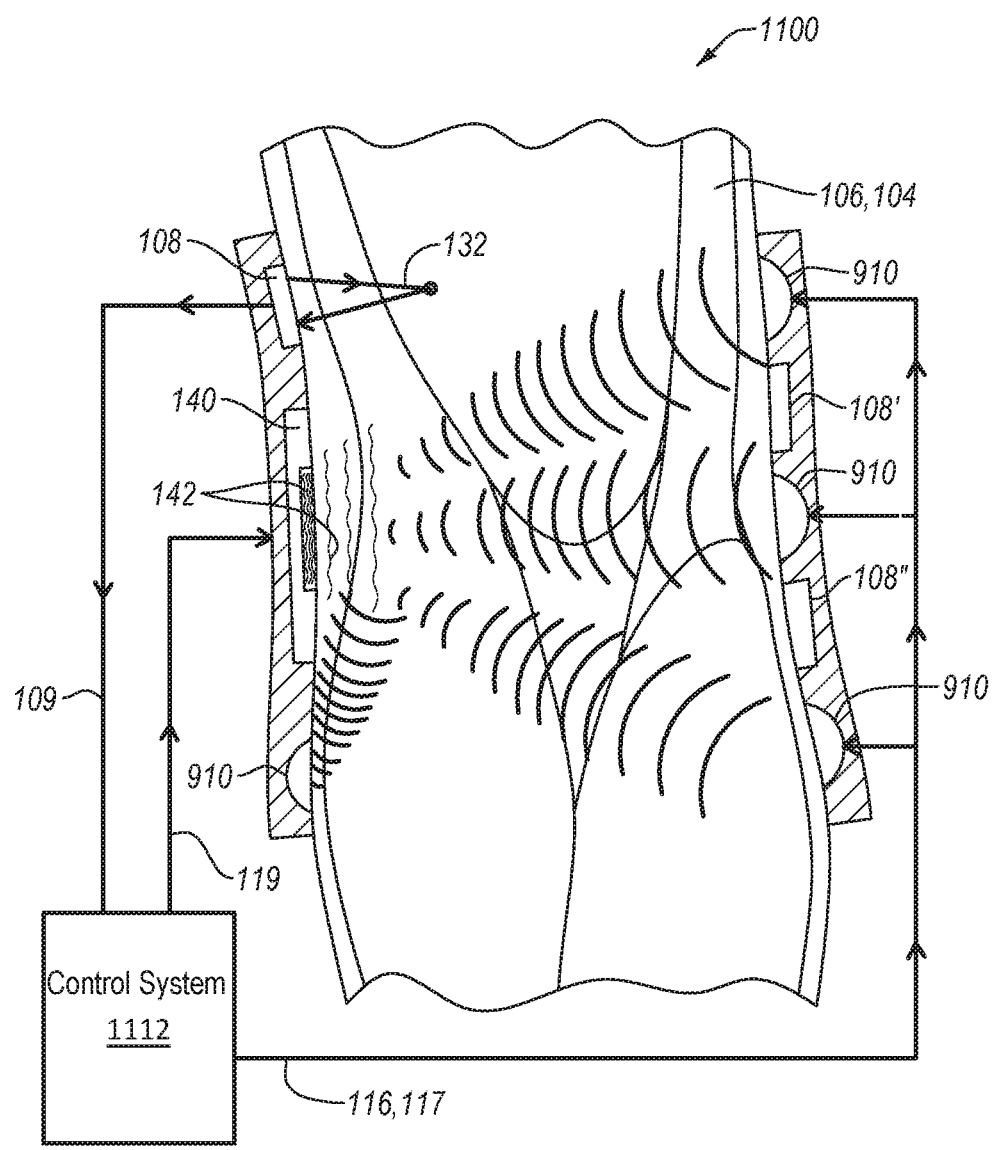
FIG. 11 is a partial cutaway view of garment system, according to an embodiment

FIG. 11 is a partial cutaway view of a garment system 1100, according to an embodiment. The garment system 1100 includes the flexible compression garment 1102; one or more sensors 108, 108', or 108"; at least one medicament delivery device 140; and one or more TSDDs 910. The garment system 1100 can include a control system 1112, which can be similar or identical to any of the control systems disclosed herein. The control system 1112 can be operably coupled to one or more of the one or more sensors 108, 108', or 108"; at least one medicament delivery device 140; and one or more TSDDs 910. The control system 1112 can be similar or identical to any of the control systems disclosed herein, in one or more aspects. For example, the control system 1112 can selectively control delivery of therapeutic radiation from the one or more TSDDs 910. The at least one medicament delivery device 140 can be operably coupled to the control system 1112 and be equipped (e.g., positioned and configured) to provide topical, transdermal, or intramuscular medicament delivery of at least one medicament 142 to the at least one body part 104. The control system 1112 can selectively control delivery of at least one medicament 142 from the at least one medicament delivery device 140, such as responsive to one or more sensing signals or determinations by the control system based thereon, a pre-programmed routine, or direction from a remote control or computer.

A power supply can be operably coupled to any components of the garment system 1100 (e.g., at least one TSDD 910 and/or at least one medicament delivery device 140) and/or control system 1112 (e.g., control electrical circuitry or memory (FIG. 5 or 6)) thereof to provide power to the components. In an embodiment, the power supply can be disposed in or on the at least one flexible compression garment 1102, or the power supply can be remote from the at least one flexible compression garment 1102, such as on a separate wearable device (FIG. 1). In such embodiments, the control system 1112 (e.g., control electrical circuitry) can direct the power supply to alter an actuation stimulus to the at least on TSDD 910 or at least one medicament delivery device 140, such as responsive to one or more sensing signals 109 indicative of the presence or absence of an activation condition. The control system 1112 can deliver an actuation signal 116 and/or aiming instructions 117 to the one or more TSDDs 910.

Alternatively to or in addition to controlling delivery of therapeutic radiation, the control system 1112 can selectively control delivery of at least one medicament 142 from the at least one medicament delivery device 140. For example, the control system 1112 can selectively control delivery of at least one medicament 142 from the at least one medicament delivery device 140 responsive to one or more sensing signals collected by the one or more sensors and/or a determination by the control system 1112 that the one or more sensing signals indicate that an activation condition is present in the at least one body part 104. For example, the control system 1112 (e.g., controller) can include an operational program thereon having executable instructions to selectively control the at least one medicament delivery device 140 to selectively deliver the at least one medicament 142, responsive to an elapsed duration or a time of day. Such operational instructions can be executed by the control electrical circuitry (e.g., processing electrical circuitry or processor). The elapsed duration can include a duration since a selected level of activity commenced, the selected level of activity terminated, a stationary state or condition commenced, a last application of therapeutic radiation, or a last application of the at least one medicament. The executable operating instructions, such as operational programs (e.g., stored in the memory), can selectively control delivery of therapeutic radiation (e.g., therapeutic ultrasonic radiation or infrared radiation) in addition to selectively controlling the delivery of the at least one medicament 142. The delivery of the at least one medicament 142 and the therapeutic radiation can be simultaneous, alternating, sequential, patterned, or random in relation to one another. For example, the medicament delivery signal 119 may be sent to the medicament delivery device 140 prior to actuation signals being sent to the at least one TSDD 910. In such embodiments, the medicament 142 can be delivered to the subject and the TSDDs 910 can subsequently activate or aid in dispersion of the medicament 142 by providing radiation thereto (e.g., changing a phase or viscosity of the medicament to flow more readily).

In an embodiment, the flexible compression garment 1102 can be similar or identical to any of the flexible compression garments disclosed herein, in one or more aspects. For example, the at least one flexible compression garment 1102 can be a tubular garment that is sized and shaped to fit in the arm of a subject 106, such as over an elbow region of the subject (e.g., at least one body part 104). In an embodiment, the one or more sensors 108, 108', or 108" are as previously described herein and can be disposed on the at least one flexible compression garment 1102, at least partially embedded therein, or housed remotely therefrom. The one or more sensors 108, 108', or 108" can detect emissions from the at least one body part, such as acoustic emissions, one or more physiological analytes in sweat, etc. The one or more sensors 108, 108', or 108" can emit scanning radiation 132 (e.g., sensing acoustic radiation having a different frequency, wavelength, or intensity than therapeutic radiation) and receive reflected scanning radiation. The detected emissions or reflected scanning radiation can include sensed information indicative of an activation condition. The one or more sensors 108, 108', or 108" can send the sensed information to the control system 1112 via one or more sensing signals 109. The sensed information in the sensing signals 109 can be received by the control system 1112 and read by the control electrical circuitry therein. The control electrical circuitry can compare the sensed information to one or more threshold values stored on one or more look-up tables in the memory to determine if an activation condition is present. In an embodiment, activation conditions can be determined to be present based upon meeting, exceeding, or falling short of a threshold level. For example, activation conditions can be indicated if the sensed information indicates that a level of salt in sweat does not meet a minimum threshold level. Responsive thereto, the control system 1112 can selectively control delivery of the at least one medicament 142 to the subject 106 and/or selectively control application of therapeutic radiation to the subject 106, such as in the region where the deficient salt content was detected.

The at least one medicament delivery device 140 can be positioned on or at least partially embedded within the at least one flexible compression garment 1102. The at least one medicament delivery device 140 can include a plurality of medicament delivery devices 140. The at least one medicament delivery device 140 can include at least one medicament 142. For example, at least some of a plurality of medicament delivery devices 140 can be configured to deliver a single identical medicament 142, or at least some of the plurality medicament delivery devices 140 can each be configured to deliver a different identical medicament 142.

The at least one medicament delivery device 140 can include a reservoir containing the at least one medicament 142. In an embodiment, the at least one medicament delivery device 140 can include an ultrasonic transducer configured to provide ultrasonic radiation effective to cause the reservoir holding the at least one medicament 142 to open or at least partially rupture. In an embodiment, the one or more TSDDs 910 can be selectively controlled (e.g., aimed) to provide ultrasonic radiation to the reservoir effective to at least partially rupture (e.g., break or open) the reservoir and deliver the at least one medicament 142. In an embodiment, garment system 1100 and/or the at least one medicament delivery device 140 can additionally or alternatively include one or more TSDDs 910 (e.g., ultrasonic transducer or infrared emitter) configured to provide therapeutic radiation (e.g., ultrasonic radiation or infrared radiation) to a region of the at least one body part 104 that the at least one medicament 142 is applied to. The TSDD(s) 910 (e.g., ultrasonic transducer) can apply therapeutic radiation (e.g., therapeutic ultrasonic radiation) to the region effective to increase an absorption rate of the at least one medicament 142 in the region, activate at least a component of the at least one medicament 142 in the region, alter a physical property (e.g., viscosity) of the at least one medicament, or control a temperature of the region (including a temperature of the medicament therein). For example, in an embodiment, the at least one medicament 142 can include a medicament that is altered in one or more of chemical composition, viscosity, or encapsulation responsive to exposure to ultrasonic radiation, electromagnetic radiation, or infrared radiation. In such embodiments, the at least one medicament delivery device 140 can include an ultrasonic transducer positioned to apply ultrasonic radiation to the medicament 142 effective to alter one or more of chemical composition, viscosity, or encapsulation of the medicament 142.

In an embodiment, the at least one medicament delivery device 140 can include one or more needles, such as a single needle operably coupled to a source of the at least one medicament 142. In an embodiment, the at least one medicament delivery device 140 can be operably coupled to a plurality of needles at least some of which are operably coupled to a source of the at least one medicament delivery device 140. In such embodiments, the control system 1112 can selectively control extension and retraction of the one or more needles and expulsion of the at least one medicament 142 from the at least one medicament source. For example, the at least one medicament delivery device 140 can include a plurality of microneedles or other microprotrusions fluidly coupled to the medicament source reservoir, wherein upon selective actuation, the at least some of the plurality of microneedles/microprotrusions can be advanced into the dermis of the subject and the reservoir can be compressed to cause the at least one medicament to travel through the plurality of microneedles/microprotrusions into the dermis of the subject. Such medicament delivery devices having one or more needles can be configured to provide topical, dermal, transdermal, and/or intramuscular delivery of one or more medicaments to one or more regions of the at least one body part 104.

In an embodiment, the at least one medicament delivery device can include an iontophoretic device, which can include one or more electrodes operably coupled to a power supply. In an embodiment, the one or more electrodes can include one or more microneedles operably coupled to a power supply. Responsive to direction from the control system 1112, the power supply can apply power to the one or more electrodes effective to drive the at least one medicament 142 into the at least one body part 104. The at least one medicament 142 can be disposed in a reservoir (e.g., a medicament soaked pad or capsule). In such embodiments, the reservoir can be disposed in contact with the dermis of the subject 106 and the one or more electrodes can contact (e.g., extend therethrough or be in fluid communication with) the reservoir effective to cause the at least one medicament to be present at the sight of application of an electrical bias effective to deliver the at least one medicament 142 via iontophoresis.

In an embodiment, the at least one medicament delivery device 140 includes a medicament-containing patch placed in contact with the skin of the subject 106. In such embodiments, the garment system 1100 and/or medicament delivery device 140 can include one or more TSDDs that are positioned and/or steerable to apply radiation to the patch or regions of the at least one body part 104 adjacent to the patch effective to cause the medicament 142 to activate, melt, disperse, or otherwise be delivered to the at least one body part 104.

In an embodiment, the at least one medicament 142 can include one or more of an anesthetic, an analgesic, an anti-biotic, an anti-inflammatory (e.g., a non-steroidal anti-inflammatory drug such as aspirin, ibuprofen, naproxen, or a COX-2 inhibitor), a rubefacient, a warming agent, a coagulant (e.g., styptic), an anti-coagulant, a cooling agent, a salicylate, a vasodilator, a vasoconstrictor, an antiseptic, a hormone, a steroid, a corticosteroid, a vitamin, a nutrient, a mineral, or any other medicament composed to treat a physical condition or symptom. For example, in an embodiment, the cooling agent can include one more ketals, carboxamides, cyclohexyl derivatives (e.g., menthols including one or more isomers thereof), or any other suitable cooling agent. The at least one medicament 142 can be a solid (e.g., powder), a gel, a liquid, a foam, or gas. In an embodiment, the one or more medicaments can be dispensed as a fluid (e.g., a liquid, an oil, a cream, a lotion, an ointment, a gas, a foam, etc.). The fluid can be a mixture of one or more medicaments, such as in a solution, dispersion, emulsion, suspension, gel, or any of mixture of the foregoing.

The at least one flexible compression garment 1102 can include one or more TSDDs 910 on, or at least partially embedded therein. The one or more TSDDs 910 can be as describe above. For example, the one or more TSDDs 910 can include ultrasonic emitters (e.g., ultrasound transceiver) and/or steerable TSDDs. The one or more TSDDs can be selectively controlled as described herein, such as in addition to or alternatively to the at least one medicament delivery device 140. For example, the control system 1112 can selectively control the one or more TSDDs 910 via one or more of actuation signals 116 or aiming instructions 117. The control system 1112 can selectively control the one or more TSDDs 910 to apply therapeutic radiation to the at least one body part 104 or a selected region thereof, responsive to one or more sensing signals or a determination based thereon. The control system 1112 can selectively control the one or more TSDDs 910 to apply therapeutic radiation to a selected region of the at least one body part where the medicament 142 is or was dispensed, such as to activate the at least one medicament 142 or change a viscosity or other property thereof. The control system 1112 can selectively control the one or more TSDDs 910 to apply therapeutic radiation to a selected region of the at least one body part where the medicament 142 is not or was not dispensed.

In an embodiment, the garment system 1000 can include one or more compression actuators, such as any of those disclosed herein.

Any of the embodiments of garment systems disclosed herein can include at least one medicament delivery device 140, such as in addition to one or more TSDDs and/or one or more compression actuators.

Figure 12:
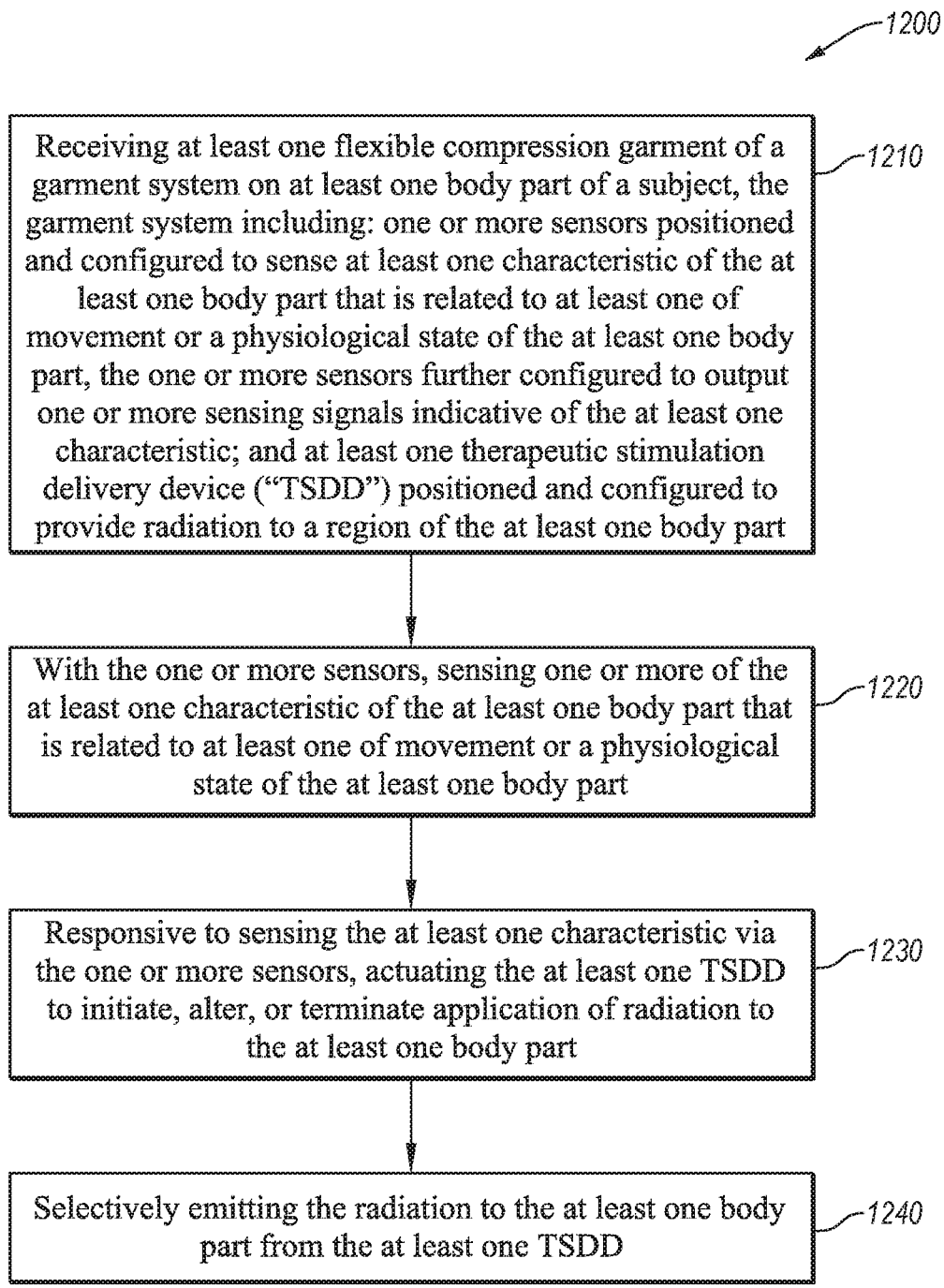
FIG. 12 is a flow diagram of an embodiment of a method of selectively delivering radiation to at least one body part of a subject responsive to sensing feedback from one or more sensors, according to an embodiment.

FIG. 12 is a flow diagram of an embodiment of a method 1200 of selectively delivering radiation to at least one body part of a subject responsive to sensing feedback from one or more sensors. The method 1200 can include an act 1210 of receiving at least one flexible compression garment of a garment system on at least one body part of a subject. The garment system can include one or more sensors positioned and configured to sense at least one characteristic of the at least one body part that is related to at least one of movement or a physiological state of the at least one body part, the one or more sensors further configured to output one or more sensing signals indicative of the at least one characteristic. The garment system can include at least one TSDD positioned and configured to provide radiation to a region of the at least one body part. The method 1200 can include an act 1220 of sensing one or more of the at least one characteristic of the at least one body part that is related to at least one of movement or a physiological state of the at least one body part, with the one or more sensors. The method 1200 can include the act 1230 actuating the at least one TSDD to initiate, alter, or terminate application of radiation to the at least one body part, responsive to sensing the at least one characteristic via the one or more sensors. The method 1200 can include the act 1240 of selectively emitting the radiation to the at least one body part from the at least one TSDD.

In some embodiments, one or more of the acts 1210-1240 can be omitted or can be performed in a different order than presented above. For example, in some embodiments, the act 1210 can be omitted.

The act 1210 of receiving at least one flexible compression garment of a garment system on at least one body part of a subject can include donning the at least one flexible compression garment. The act 1210 of receiving at least one flexible compression garment of a garment system on at least one body part of a subject can include putting the at least one flexible compression garment on another person such as a patient, client, or ward. The garment system of act 1210 can include any of the garment systems or components thereof disclosed herein. For example, the garment system can include at least one flexible compression garment (e.g., a plurality of flexible compression garments); and one or more of at least one TSDD, one or more sensors, a control system, at least one medicament delivery device, or one or more compression actuators. In an embodiment, one or more flexible compression garments of the at least one flexible compression garment can include one or more of at least one TSDD, one or more sensors, a control system, at least one medicament delivery device, or one or more compression actuators. In an embodiment, some flexible compression garments of the plurality of flexible compression garments can include only certain ones of at least one TSDD, one or more sensors, a control system, at least one medicament delivery device, or one or more compression actuators, while the garment system, as a whole, includes all or some of the above (e.g., a controller for a plurality of flexible compression garments is hosted on only one of the plurality of flexible compression garments, while each of the plurality of flexible compression garments includes one or more sensors and TSDDs).

In an embodiment, the garment system of act 1210 can include a control system (e.g., controller) having control electrical circuitry and a memory (e.g., memory storage medium) operably coupled to the control electrical circuitry, wherein the memory includes one or more machine readable programs stored thereon and the control electrical circuitry is configured to execute the one or more machine readable programs.

The act 1210 of receiving at least one flexible compression garment of a garment system on at least one body part of a subject can include receiving the at least one flexible compression garment on at least a portion of an arm, at least a portion of a forearm, at least a portion of a wrist, at least a portion of a hand, at least a portion of a thigh, at least a portion of a lower leg, at least a portion of a foot, at least a portion of a neck, at least a portion of an abdomen, at least a portion of a back, or at least a portion of a chest. The act 1210 of receiving the at least one flexible compression garment on at least one body part can include positioning the at least one flexible compression garment on another person (e.g., a patient, ward, child, etc.) or on oneself.

The act 1220 of sensing one or more of the at least one characteristic of the at least one body part that is related to at least one of movement or a physiological state of the at least one body part, with the one or more sensors, can include sensing at least one of nerve activity of at least tissue in a region of the at least one body part, an internal temperature of the region, an external temperature, swelling, inflammation, blood flow in the region, tissue oxygenation in the region, a strain on the at least one body part, a conductance in the region, an impedance in the region, a pH in a body fluid in the region, an amount of physiological analyte in the region, an acoustic emission from tissue in the region, a biochemical activity in the region, changes of any of the foregoing exceeding a threshold value, or occurrence or cessation of any of the foregoing for a duration longer than a selected duration of time. In an embodiment, 1220 sensing one or more of the at least one characteristic of the at least one body part that is related to at least one of movement or a physiological state of the at least one body part can include sensing one or more of a motion of the subject, a motion of the at least one body part such as one or more limbs of the subject, a stationary condition of the subject, or a stationary condition of the at least one body part such as one or more limbs of the subject. In an embodiment, sensing one or more of the at least one characteristic of the at least one body part that is related to at least one of movement or a physiological state of the at least one body part includes sensing at least one characteristic that is related to at least one of movement or a physiological state of a plurality of body parts. For example, the sensing can include sensing at least one characteristic that is related to at least one of movement of both legs and/or arms (or any combination of body parts) of a subject. In an embodiment, the sensing can include at least one characteristic that is related to a physiological state a back and leg of the subject, or any combination of body parts of a subject.

In an embodiment, the method 1200 can further include including transmitting one or more sensing signals from the one or more sensors to the control system (e.g., controller). The one or more sensing signals can include sensed information indicating the at least one characteristic of the at least one body part that is related to at least one of movement or a physiological state of the at least one body part. The sensed information can include information indicative of an activation condition. In such embodiments, the method 1200 can include storing, in the controller (e.g., in the memory storage medium), at least one of the one or more sensing signals from the one or more sensors or actuation data corresponding to actuation of the at least one TSDD.

The act 1230 of actuating the at least one TSDD to initiate, alter, or terminate application of radiation to the at least one body part, responsive to sensing the at least one characteristic via the one or more sensors can include sending one or more actuation signals to the at least one TSDD, such as via the control system (e.g., from the control electrical circuitry thereof). In an embodiment, the at least one TSDD can include a plurality of TSDDs, and actuating the at least one TSDD includes actuating at least one (e.g., at least some or each) of the plurality of TSDDs. In such embodiments, the act 1230 of actuating the at least one TSDD can include actuating the plurality of TSDDs, such as actuating each to emit therapeutic radiation to separate regions of the at least one body part. In some embodiments, the act 1230 of actuating the at least one TSDD can include actuating the plurality of TSDDs to emit (e.g., focus) therapeutic radiation to a single region or focal point in or on the at least one body part.

The act 1230 of actuating the at least one TSDD to initiate, alter, or terminate application of radiation to the at least one body part, responsive to sensing the at least one characteristic via the one or more sensors can include sending one or more actuation signals to the at least one TSDD. The one or more actuation signals can encode or contain instructions for the at least one TSDD to emit a selected wavelength, frequency, intensity, and/or duration of therapeutic radiation (e.g., therapeutic ultrasonic radiation) to the at least one body part. In an embodiment, the act 1230 of actuating the at least one TSDD to initiate, alter, or terminate application of radiation to the at least one body part, responsive to sensing the at least one characteristic via the one or more sensors can include sending one or more actuation signals to the at least one TSDD can include sending aiming instructions to the at least one TSDD. Sending aiming instructions to the at least one TSDD can be effective to cause the at least one TSDD to aim therapeutic radiation to a selected region or point in the at least one body part. In embodiments, the act 1230 of actuating the at least one TSDD to initiate, alter, or terminate application of radiation to the at least one body part, can be responsive to a pre-programmed routine stored in the memory, direction from a remote device (e.g., entered by a user or automatically by the device) such as a controller or a computer, or direction entered into the system by a user (e.g., the subject wearing the at least one flexible compression garment, a medical professional, a parent, a care taker, etc.).

In an embodiment, the controller includes a user interface configured to indicate an activation status of the garment system to a user and to accept input therefrom, and the method 1200 includes initiating, terminating, or adjusting application of radiation to the at least one body part from the at least one TSDD with the user interface, such as via manual input by a user (e.g., the subject or a medical professional).

The act 1240 of selectively emitting the radiation to the at least one body part from the at least one TSDD can include selectively emitting one or more of acoustic radiation (e.g., sound or ultrasound), electromagnetic radiation (e.g., heat, radio, etc.), or optical radiation (e.g., infrared, UV, or visible light). The act 1240 of selectively emitting the radiation to the at least one body part from the at least one TSDD can include selectively emitting one or more of ultrasonic or infrared radiation to the at least one body part. The act 1240 of selectively emitting the radiation to the at least one body part from the at least one TSDD can include selectively emitting one or more frequencies, intensities, or wavelengths of radiation to the at least one body part or a region thereof. For example, selectively emitting one or more frequencies, intensities, or wavelengths of radiation to the at least one body part or a region thereof can include selectively emitting one or more frequencies of ultrasonic radiation into the at least one body part, such as responsive to one or more actuation signals from the control system. The act 1240 of selectively emitting the radiation to the at least one body part from the at least one TSDD can include emitting therapeutic radiation (e.g., therapeutic ultrasonic radiation) into the at least one body part, where the therapeutic radiation has a different wavelength, frequency, intensity, or timing than scanning radiation (e.g., radiation emitted from the one or more sensors for the purpose of interrogating a region of the at least one body part). In an embodiment, selectively emitting radiation to the at least one body part from the at least one TSDD can includes selectively emitting the radiation for a selected duration of time. The selected duration of time can include at least about 1 second, about 5 seconds, about 10 seconds about 20 seconds about 30 seconds, about 1 minute, about 2 minutes, about 5 minutes, about 10 minutes, about 15 minutes, about 30 minutes, about 30 minutes, about 1 hour, about 2 hours, about 3 hours, about 4 hours, about 6 hours, about 8 hours, about 12 hours, or ranges of time including any combination of the preceding as endpoints. In an embodiment, selectively emitting radiation to the at least one body part from the at least one TSDD can includes selectively emitting the radiation in a selected number of pulses each having a selected duration and a selected gap therebetween.

In an embodiment, the at least one TSDD can include a plurality of TSDDs. In such embodiments, the act 1240 of selectively emitting the radiation to the at least one body part from the at least one TSDD can include selectively emitting the radiation to a plurality of regions of the at least one body part with the plurality of TSDDs. In some embodiments, wherein selectively emitting the radiation to the at least one body part from the at least one TSDD includes selectively emitting radiation from the plurality of TSDDs to a single region of the at least one body part. For example, selectively emitting the radiation from the plurality of TSDDs to a single region of the at least one body part can include converging (e.g., focusing), in the single region (e.g., focal point), the radiation emitted from at least some (e.g., at least two) of the plurality of TSDDs.

In an embodiment, the act 1240 of selectively emitting the radiation to the at least one body part from the at least one TSDD can include selectively emitting the radiation to at least a region of the at least one body part from the at least one TSDD effective to stimulate tissue in the at least one region, such as responsive to determining that the subject is in an inactive state, responsive to determining the duration since the subject initiated a physical activity, a pre-programmed routine (e.g., a timed routine), or direction by a remote control or computer.

The act 1240 of selectively emitting the radiation to the at least one body part from the at least one TSDD can include selectively emitting ultrasonic radiation to at least a region of the at least one body part from the at least one TSDD effective to increase a temperature of tissue in the at least one region, such as responsive to determining the presence of an indication of pain. For example, selectively emitting the radiation to at least a region of the at least one body part from the at least one TSDD effective to stimulate tissue in the at least one region can include emitting ultrasonic radiation effective to increase the temperature in the at least one region. In an embodiment, selectively emitting the radiation to at least a region of the at least one body part from the at least one TSDD effective to stimulate tissue in the at least one region can include emitting therapeutic radiation (e.g., therapeutic ultrasonic radiation) effective to block pain receptors in the at least one region.

In an embodiment, the act 1240 of selectively emitting the radiation to the at least one body part from the at least one TSDD can include selectively emitting the radiation for a first duration in a first region of the at least one body part, and selectively emitting the radiation for a at least a second duration in at least a second region of the at least one body part. In such embodiments, the first region can include a first depth of a tissue of the subject and the at least a second region can include at least a second depth of the tissue. In an embodiment, the first region can include a first tissue of the subject (e.g., a first muscle) and the at least a second region can include at least a second tissue (e.g., a second muscle or skin) of the subject.

In an embodiment, at least some of the one or more sensors and at least some of the one or more TSDDs can emit a similar or identical type of radiation (e.g., ultrasonic, infrared, etc.). For example, the one or more sensors can include at least one scanning ultrasound transducer configured to transmit and receive scanning ultrasonic radiation, and sensing one or more of at least one characteristic associated with movement or at least one characteristic of a region of at least one body part can include sensing with at least one scanning ultrasound transducer. Further, the at least one TSDD can include at least one therapeutic ultrasound transducer configured to emit therapeutic ultrasonic radiation, and selectively emitting radiation to the at least one body part can include emitting therapeutic ultrasonic radiation from the at least one therapeutic ultrasound transducer. In such embodiments, the scanning radiation and the therapeutic radiation can differ from one another by one or more of frequency, wavelength, intensity, or duration of application. For example, the therapeutic radiation can have a greater intensity and duration that the scanning radiation.

In an embodiment, the method 1200 can include determining if the at least one characteristic of a region indicates a threshold level of the at least one characteristic has been reached, exceeded, or not met. For example, the control system (e.g., memory) can store a plurality of threshold levels for any of the at least one characteristics disclosed herein, and the control electrical circuitry can compare the sensed information to one or more of the threshold values to determine if the sensed information meets, exceeds, or falls short of the one or more threshold values. Depending on the at least one characteristic, the control system can determine that an activation condition is present based on the met, exceeded, or not met threshold value (e.g., a pulse is dangerously low or high, or an inactivity state is indicated by a lack of movement for a selected duration of time). The memory can store an operational program for actuating one or more of the TSDDS, compression actuators, and/or medicament dispensing devices, and the control electrical circuitry can execute the same based on the determination that an activation condition is present. For example, the method 1200 can include selectively emitting the radiation to at least a region of the at least one body part from the at least one TSDD effective to stimulate tissue in the at least one region, responsive to determining if the at least one characteristic indicates that a threshold level has been reached.

The method 1200 can include determining at least one physiological characteristic of a region of the at least one body part such as at least one of a nerve activity of tissue in the region; an internal temperature of the region; an external temperature; blood flow in the region; tissue oxygenation in the region; a strain on the at least one body part; a conductance in the region; an impedance in the region; a pH in a body fluid in the region; a presence or amount of a physiological analyte in the region; an acoustic emission from tissue in the region; a biochemical activity in the region; any of the foregoing meeting, exceeding, or falling short of a threshold value for a selected duration of time; changes of any of the foregoing meeting, exceeding, or falling short of a threshold value; or occurrence or cessation of any of the foregoing for a duration longer than a selected duration of time. In an embodiment, the selected duration of time can be at least about 1 second, such as about 10 seconds, about 30 seconds, about 1 minute, about 2 minutes, about 5 minutes, about 10 minutes, about 20 minutes, about 30 minutes, about 1 hour, about 2 hours, about 3 hours, about 4 hours, about 6 hours, about 8 hours, about 12 hours, or ranges including any combination of the foregoing as endpoints. In an embodiment, selectively emitting the radiation to at least a region of the at least one body part from the at least one TSDD effective to stimulate tissue in the at least one region, can be responsive to determining the at least one characteristic of a region, a pre-programmed routine, or direction from a remote control or computer (as automatically directed by the device or by a user of the device).

The method 1200 can further include an act of determining a presence of an indication of pain, at least partially based on the one or more sensing signals, using the control system. For example, the control system can determine the presence or absence of an indication of pain by detecting one or more physiological analytes or amounts thereof known to be associated with a pain response from an animal (e.g., human) subject, such as in a fluid or tissue of the subject. In an embodiment, the control system can interrogate sensed information delivered in the sensing signals for information correlated to a pain condition or response. The control system can compare the sensed information to one or more corresponding threshold values to determine if a subject is exhibiting characteristics indicative of pain. The characteristics associated with pain can be any of those disclosed herein. For example, specific values or patterns of the characteristic(s) of the at least one body part that is related to at least one of movement or a physiological state of the at least one body part can indicate that a subject is in pain. In an embodiment, the control system can determine a presence of an indication of pain based on one or more of nerve signals indicative of pain (e.g., electrical signals), an amount of one or more chemicals in a fluid of the subject (e.g., salt(s), glucose, lactate, hormone(s), peptides, etc.), a specific pattern of movement (e.g., movement indicating limping or favoring a limb, moving slower than a normal rate, moving in a different pattern than a normal pattern), changes of any of the foregoing, or any other criteria for determining a presence of pain disclosed herein. For example, changes in levels of physiological chemicals can be associated with increased muscle use or the presence of a pain condition. Specifically, increases in lactate levels or in glucose levels (e.g., in response to released hormones), measurable in sweat or bodily tissues (e.g., interstitial tissues), can be associated with increased muscle use or the presence of pain.

A threshold value can be compared against a detected concentration of a physiological analyte or an amount of the at least one characteristic to determine if the at least one characteristic sensed by the one or more sensors indicates a presence of an indication of pain (e.g., provide inference that the subject is in pain). In an embodiment, increased levels of one or more hormones (e.g., cortisol, pregnenolone, DHEA, testosterone, progesterone, estrogen, T3, and T4) released in response to pain are measurable in sweat or other bodily fluids. In such embodiments, baseline levels or a threshold level can be compared against the sensed levels of the same, such as by the control system. In an embodiment, neuropeptides (e.g., neuropeptide Y, substance P and CGRP or other neurotransmitters (e.g., glutamate)) released in response to pain are measurable in sweat or other bodily fluids. Such measured or detected physiological analytes can be compared to threshold values (e.g., a base level not associated with pain), patterns, or combinations of physiological analytes to determine a presence or absence of an indication of pain. For example, the control system can determine if a chemical indication of pain is present based at least in part on a detected presence or change in concentration of one or more physiological analytes. In an embodiment, the presence of an amount of lactate in sweat over a threshold value can indicate that a subject is in pain. In an embodiment, electrical signals detected by the one or more sensors and known to correspond to pain receptors can be detected indications of pain. The control electrical circuitry can direct the at least one TSDD to selectively deliver the radiation responsive to a determination that the subject is exhibiting a presence of an indication of pain.

In an embodiment, a determination of the presence of an indication of pain can including sensing movement of a subject or one or more body parts of the subject, and determining therefrom that a motion or plurality of motions indicate a presence of pain. Movement of the body portion of the individual can be a preventative treatment or therapeutic treatment of pain. For example, lack of movement or repetition of a movement can be indicative of an increased risk for pain, while sensed and recorded motions indicative of appropriate therapeutic or preventative movements can be indicative of a decreased risk for pain. Muscle fatigue can be associated with, can induce, or can be an indicator of muscle pain.

Motion of the body portion can provide an indication as to when a therapeutic radiation treatment can be employed. For example, garment system can provide treatment to the subject when the at least one body part is undergoing motion determined (e.g., previously or simultaneously) to be associated with an increase in pain, such as providing a palliative treatment. For example, garment system can provide treatment to the individual subject when there has been a lack of motion in the at least one body part of the subject or the subject has been at rest for a duration of time above a threshold duration. The threshold duration can be at least about 1 minute, such as about 1 minute to about 10 hours, or about 5 minutes to about 5 hours, about 10 minutes to about 1 hour, about 20 minutes to about 40 minutes, about 30 minutes to about 1 hour, or more than about 30 minutes. Treatment of the individual subject to induce movement can be a preventative measure (e.g., to induce movement to prevent onset of arthralgia, myalgia, etc.). For example, the garment systems and methods herein can provide treatment to the subject when the subject is at rest. Treatment of the subject during a rest state can provide a convenient and non-interruptive mechanism to treat pain (e.g., chronic or long-term pain) or a medical condition experienced by the subject.

The one or more sensors can include one or more motion sensors configured to detect one or more of a movement of at least one body part and a position of the at least one body part. The movement of the at least one body part, the position of the at least one body part, or combinations thereof can be indicative of a pain state of the subject. For example, the motion of the body portion can be indicative of pain experienced by the subject, such as where the motion includes a guarding motion, an awkward gait, a limp, pronounced use of non-dominant limb, pronounced rubbing or massage of the at least one body part (e.g., repeated or deep massage), or the like, or combinations thereof. The movement of the at least one body part, the position of the at least one body part, or combinations thereof can be indicative of a risk of increased pain experienced by the subject, for example, when the movement has been determined to be temporally associated with pain (e.g., as indicated by changes in autonomic responses) or when a movement (e.g., a lack of movement) or repetition of movement indicates a risk of pain.

The one or more motion sensors can generate a sensing signal based on a repeated motion of the body portion. For example, the garment system can be positioned on a wrist of a subject and the one or more motion sensors can measure a repeated flexing or bending of the wrist, such as during movement of the hand or one or more fingers. The one or more motion sensors can measure a number of repetitions of a movement of a body portion. For example, the system can be positioned on a finger of a subject and the motion sensor measures the number of repetitions that the particular finger is flexed or bent. In an embodiment, the control system an use a counter or a timer in conjunction with the one or more motion sensors to determine a duration over which the movements detected by the sensors are taking place.

The one or more motion sensors can measure a speed of a movement of at least one body part. The one or more motion sensors can measure a force of a movement of at least one body part. The one or more motion sensors can measure a duration of a movement of at least one body part. The duration can include one or more of a total duration of movement within a period of time (e.g., duration encompassing multiple repetitions of movement) and a total duration of movement for a single repetition of movement. The period of time over which the movement is measured can include, but is not limited to, seconds (e.g., 10 seconds, 30 seconds), a minute, 20 minutes, 30 minutes, an hour, a portion of a day during which a subject is awake and active, a portion of a day during which a subject is asleep or otherwise inactive, a day, or longer duration.

In an embodiment, the control system can include programming (e.g., operational instructions) effective to execute a treatment (e.g., application of therapeutic radiation, compression, or at least one medicament) when the sensing signals from the one or more motion sensors indicate that the at least one body part experienced a particular type of movement, or a particular type of movement for a selected duration, or an absence of a selected type of movement(s) for a selected duration. For example, the sensing signals from the one or more motion sensors can indicate that the at least one body part experienced a particular type of movement, such as a predetermined high velocity of movement, a high level of force output, a too-rapid step (e.g., indicating tripping), a movement in a particular direction (e.g., indicating a twisting of a joint), or the like, which can indicate an increased risk of pain. For example, the sensing signals from the one or more motion sensors might indicate pronounced minimalization of motion or agitation affecting a body site (e.g., a muscle), e.g., "guarding". For example, the sensing signals from the motion sensor can indicate that the at least one body part experienced a particular type of movement such as experiencing a predetermined velocity of movement (e.g., the individual subject is slowing down), an awkward gait, a limp, pronounced use of non-dominant limb, or the like, which can indicate a level of discomfort or pain experienced by the individual subject. Responsive to such sensed information in the sensing signals, the control system can determine that there is a presence of an indication of pain and instruct the at least one TSDD to selectively emit radiation into the at least one body part to treat the indicated pain.

In an embodiment, selectively emitting the radiation to at least a region of the at least one body part from the at least one TSDD effective to stimulate tissue in the at least one region can be responsive to determining the presence of an indication of pain. In an embodiment, the method 1200 can include selectively emitting ultrasonic radiation to at least a region of the at least one body part from the at least one TSDD effective to block pain receptors in the at least one region, responsive to determining the presence of an indication of pain.

The methods herein can include determining at least one characteristic of the at least one body part that is to movement of the at least one body part, such as a presence or absence of movement, a direction of said movement, a distance of said movement, a pattern of said movement, a duration of said movement, force exerted by said movement, etc. For example, the method 1200 can include determining if the subject is in an inactive state, at least partially based the one or more sensing signals, with the control system. For example, the control system of method 1200 can determine that a subject is in an inactive state by sensing the movement of the subject or one or more body parts thereof (e.g., arms, legs, etc.) over a duration of time. If the control system receives sensing signals indicating that a subject has not moved or certain ones of the one or more body parts have not moved for a threshold duration (e.g., 10 minutes, 30 minutes, 1 hour, 2 hours, 4 hours, 8 hours, ranges including any of the preceding as endpoints), the control system can determine that the subject (or a body part thereof) is in an inactive state. In an embodiment, the one or more sensors can detect a heart rate or pulse of a subject and the control system can determine that if the heart rate or pulse is below a threshold level and/or for a selected duration of time, the subject is inactive (at least below a threshold level or heart rate or pulse), such as resting, sitting at a desk, or sleeping. The above determinations of activity or inactivity can be determined by the control system at least partially based on the sensing signals containing the sensed information. The above determinations of activity or inactivity can be determined by the control system at least partially based on one or more threshold levels stored in the control system. The control system (e.g., the control electrical circuitry or processor) can include operational instructions stored in the memory to compare the sensed information to one or more look-up tables correlating to the sensed at least one characteristic stored in the memory. The control system can determine that an activation condition is present or absent based on the sensed information being above, meeting, or being below a threshold value. For example, the sensed information can indicate that a glucose level in sweat is above a threshold for a level associated with a pain response in a subject, and responsive thereto, execute an operational program that instructs one or more TSDDs (and/or medicament delivery devices and/or compression actuators) to selectively initiate, alter, or terminate application of radiation (e.g., therapeutic ultrasonic radiation) to the at least one body part of the subject to alleviate the pain or treat a condition correlated to be causing the pain.

In an embodiment, the method 1200 include determining a duration since the subject initiated a physical activity, with the controller, using the sensed information in the one or more sensing signals sent from the one or more sensors. For example, the one or more sensors can sense a movement of the subject, movement(s) of one or more body parts of the subject (e.g., arms and/or legs), or patterns of any of the foregoing, and the control system (e.g., control electrical circuitry) can compare the same to one or look-up tables stored in the memory or to a timer initiated at the instant of receiving the sensing signals. The control system can determine a duration since the subject has initiated a movement of the subject, movement(s) of one or more body parts of the subject, patterns of any of the foregoing, or a specific activity indicated by any of the foregoing, using the one or more sensing signals. The control system can correlate the a movement of the subject, movement(s) of one or more body parts of the subject, or patterns of any of the foregoing to the one or more look-up tables to determine if the subject is participating in a specific activity (e.g., a specific exercise, work-out, sport, etc.).

In an embodiment, the method 1200 can include determining if the subject is injured. For example, the sensing signals can indicate that a subject is favoring a limb (e.g., limping). The control system can include look-up tables and threshold values of characteristics of movement indicating that a subject is limping and therefore injured, and can determine the limb that is injured. The control system can compare the sensed information in the sensing signals to the look-up tables and/or threshold values to determine if a subject is exhibiting signs of being injured. Responsive to a determination that the subject is exhibiting signs of being injured, the control system can provide actuation signals to the one or more TSDDs (and/or compression actuators and/or medicament delivery devices) to provide treatment (e.g., therapeutic radiation, compression, or medicament(s)) to the at least one body part. For example, the method 1200 can include determining if the at least one characteristic of a region indicates a muscle cramp, a muscle contraction, or muscle spasm. Such a determination can be made using electrical signals (e.g., nerve impulses) detected in the at least one body part, physiological analytes (e.g., salt concentrations in sweat), or acoustic information (e.g., scanning acoustic radiation) from the at least one body part. The sensing information can indicate that a subject is exhibiting signs correlated to one or more of a muscle cramp, a muscle contraction, or muscle spasm. Responsive to determining if the at least one characteristic indicates a muscle cramp, a muscle contraction, or muscle spasm, the method 1200 can include selectively emitting the radiation to at least a region of the at least one body part from the at least one TSDD effective to stimulate tissue in the at least one region.

In an embodiment, the garment system can include one or more compression actuators configured to cause at least a portion of the at least one flexible compression garment to compress against or relieve compression against the at least one body part, and the method 1200 can include selectively actuating the one or more compression actuators to compress or relieve compression against the at least one body, such as responsive to determining that an activation condition is present. The one or more compression actuators can be similar or identical to any of the same disclosed herein.

In an embodiment, the garment system can include at least one medicament delivery device operably coupled to a controller and positioned and equipped provide topical, transdermal, or intramuscular medicament delivery to the at least one body part, and the method 1200 can include selectively controlling delivery of the at least one medicament from the at least one medicament delivery device, such as responsive to determining that an activation condition is present. For example, the method 1200 can include actuating the one or more medicament delivery devices to selectively deliver the at least one medicament. The medicament delivery device and the at least one medicament can be similar or identical to any of the same disclosed herein. In an embodiment, the controller includes programming to cause the at least one medicament delivery device to selectively deliver the at least one medicament, such as responsive to the one or more sensing signals indicative of the at least one characteristic or presence of the activation condition based thereon.

In an embodiment, actuating the one or more medicament delivery devices can include compressing or bursting a reservoir holding the one or more medicaments. In an embodiment, actuating the one or more medicament delivery devices can include directing radiation (e.g., ultrasonic radiation) to a reservoir holding the one or more medicaments, effective to at least partially rupture the reservoir. In an embodiment, the method 1200 can include actuating the one or more TSDDs to emit radiation to a region in which the at least one medicament has been, is, or will be dispensed, such as to activate at least one component of the medicament, aid in absorption or delivery of the at least one medicament by a tissue, or change a phase or viscosity of the at least one medicament.

In an embodiment, methods of selectively delivering radiation to at least one body part can include actively or dynamically scanning the at least one body part during application of radiation and dynamically adjusting, terminating, or initiating application of the therapeutic radiation thereto. For example, method can include sensing a characteristic (e.g., temperature) of the at least one body part while selectively emitting the radiation to the at least one body part. As explained in more detail below, methods can include dynamically applying (e.g., terminating or adjusting) application of the radiation to the at least one body part, responsive to a sensed characteristic (e.g., temperature) in the at least one body part, while the therapeutic radiation is being applied.

Figure 13:
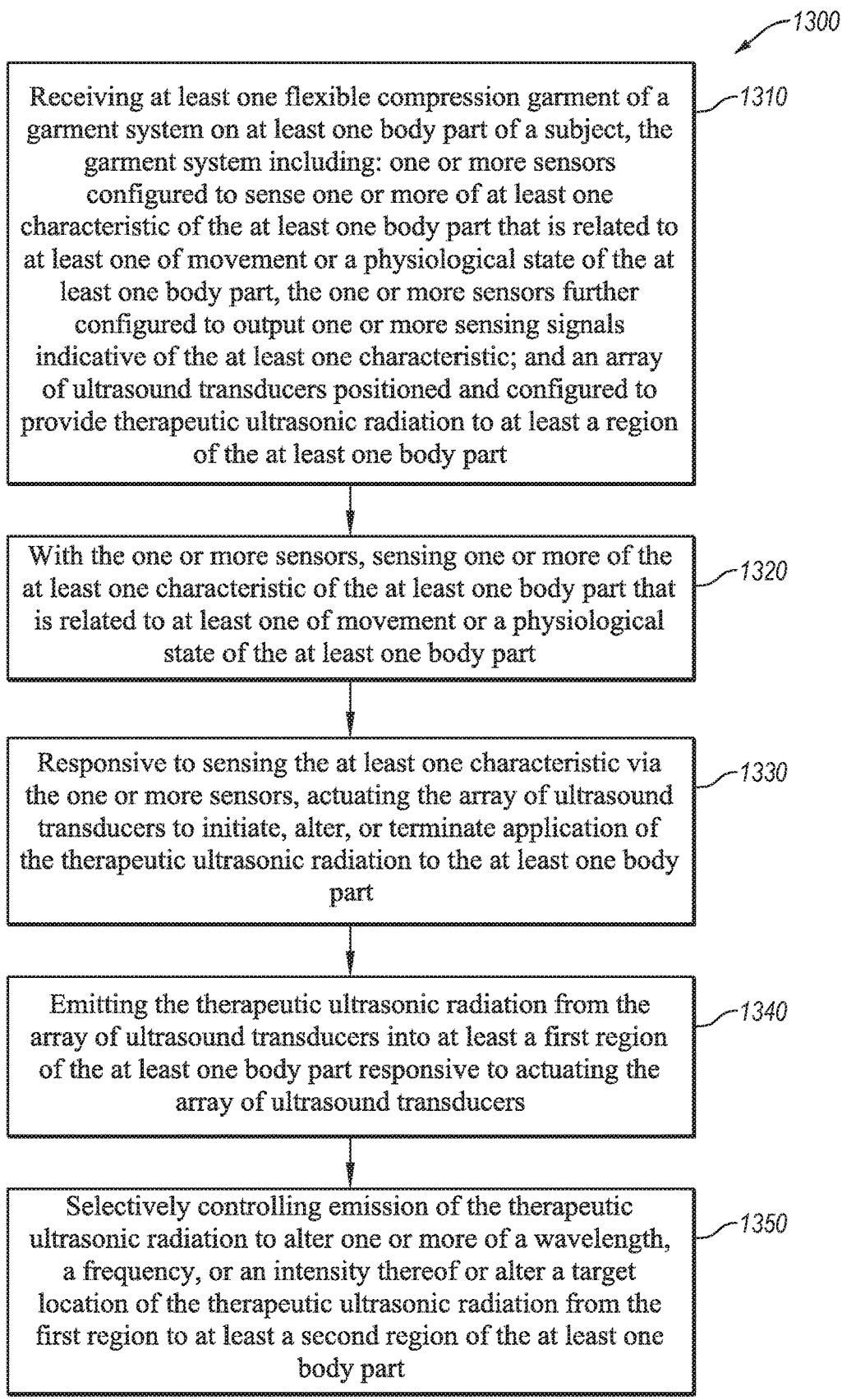
FIG. 13 is a flow diagram of an embodiment of a method of selectively and dynamically delivering radiation to at least one body part of a subject responsive to sensing feedback from one or more sensors while the radiation is being delivered, according to an embodiment.

FIG. 13 is a flow diagram of an embodiment of a method 1300 of selectively and dynamically delivering radiation to at least one body part of a subject responsive to sensing feedback from one or more sensors while the radiation is being delivered. The method 1300 can include an act 1310 of receiving at least one flexible compression garment of a garment system on at least one body part of a subject, the garment system including one or more sensors configured to sense one or more of at least one characteristic of the at least one body part that is related to at least one of movement or a physiological state of the at least one body part, the one or more sensors further configured to output one or more sensing signals indicative of the at least one characteristic; and an array of ultrasound transducers positioned and configured to provide therapeutic ultrasonic radiation to at least a region of the at least one body part. The method 1300 can include an act 1320 of with the one or more sensors, sensing one or more of the at least one characteristic of the at least one body part that is related to at least one of movement or a physiological state of the at least one body part. The method 1300 can include the act 1330 of responsive to sensing the at least one characteristic via the one or more sensors, actuating the array of ultrasound transducers to initiate, alter, or terminate application of the therapeutic ultrasonic radiation to the at least one body part. The method 1300 can include the act 1340 of emitting the therapeutic ultrasonic radiation from the array of ultrasound transducers into at least a first region of the at least one body part responsive to actuating the array of ultrasound transducers. And, the method 1300 can include the act 1350 of selectively controlling emission of the therapeutic ultrasonic radiation to alter one or more of a wavelength, a frequency, or an intensity thereof or alter a target location of the therapeutic ultrasonic radiation from the first region to at least a second region of the at least one body part.

In some embodiments, one or more of the acts 1310-1350 can be omitted or can be performed in a different order than presented above. For example, in some embodiments, the act 1310 can be omitted.

The act 1310 of receiving at least one flexible compression garment of a garment system on at least one body part of a subject, can be similar or identical to the act 1210 described above, in one or more aspects. For example, the act 1310 of receiving at least one flexible compression garment of a garment system on at least one body part of a subject can include donning the at least one flexible compression garment, or putting the at least one flexible compression garment on another person such as a patient, client, or ward. As another example, receiving at least one flexible compression garment of a garment system on at least one body part of a subject can include receiving the at least one flexible compression garment on one or more of at least a portion of an arm, at least a portion of a forearm, at least a portion of a wrist, at least a portion of a hand, at least a portion of a thigh, at least a portion of a lower leg, at least a portion of a foot, at least a portion of a neck, at least a portion of an abdomen, at least a portion of a back, or at least a portion of a chest. The garment system of act 1310 can include any of the garment systems or components thereof disclosed herein, such as the garment system 1100. For example, the garment system can include at least one flexible compression garment (e.g., a plurality of flexible compression garments); an array of array of TSDDs; an array of sensors; a control system; and optionally one or more of at least one medicament delivery device, or one or more compression actuators. Any of the preceding can be disposed on or at least partially embedded in the at least one flexible compression garment. In an embodiment, some flexible compression garments of the plurality of flexible compression garments can include only certain ones of the array of TSDDs, the array of sensors, the control system, the at least one medicament delivery device, or one or more compression actuators, while the garment system, as a whole, includes combinations of the above (e.g., a controller for a plurality of flexible compression garments is hosted on only one of the plurality of flexible compression garments, while each of the plurality of flexible compression garments includes one or more sensors and TSDDs).

The act 1310 can include using a garment system including a control system (e.g., controller) having control electrical circuitry and a memory storage medium operably coupled to the control electrical circuitry, wherein the memory storage medium includes one or more machine readable programs stored thereon and the control electrical circuitry is configured to execute the one or more machine readable programs effective to control the at least one TSDD (e.g., array of ultrasound transducers). The control system can include one or more operational instructions (e.g., operational programs) stored therein configured to direct the garment system to dynamically apply (e.g., adjust application) the therapeutic radiation, such as changing or altering one or more of wavelength, frequency, intensity, or duration of the therapeutic radiation applied responsive to sensing information and collected during application of the therapeutic radiation. In such a manner, the control system can dynamically (e.g., continuously, incrementally, periodically, etc.) adjust aspects of the therapeutic radiation being applied during application of the same.

The act 1320 of with the one or more sensors, sensing one or more of the at least one characteristic of the at least one body part that is related to at least one of movement or a physiological state of the at least one body part can be similar or identical to the act 1220 of sensing one or more of the at least one characteristic of the at least one body part that is related to at least one of movement or a physiological state of the at least one body part disclosed above, in one or more aspects. For example, the act 1320 of with the one or more sensors, sensing one or more of the at least one characteristic of the at least one body part that is related to at least one of movement or a physiological state of the at least one body part can include sensing at least one of nerve activity of at least tissue in a region of at the least one body part, an internal temperature of the region, an external temperature, blood flow the region, tissue oxygenation in the region, a conductance in the region, an impedance in the region, a pH in a body fluid in the region, an amount of a physiological analyte in the region, an acoustic emission from tissue in the region, biochemical activity in the region, changes of any of the foregoing exceeding a threshold value, or occurrence or cessation of any of the foregoing for a duration longer than a selected duration of time.

The act 1320 can be dynamically carried out during application of a treatment, such as to monitor the effects of the treatment. For example, the act 1320 of with the one or more sensors, sensing one or more of the at least one characteristic of the at least one body part that is related to at least one of movement or a physiological state of the at least one body part can include sensing one or more of the at least one characteristic of the at least one body part that is related to at least one of movement or a physiological state of the at least one body part while therapeutic radiation is being applied to the at least one body part, selective compression is being applied to the at least one body part, at least one medicament is being dispensed to the at least one body part, or combinations of any of the foregoing. In an embodiment, sensing one or more of at least one characteristic is continuously or intermittently carried out during one or both of emitting the therapeutic ultrasonic radiation into at least a first region of the at least one body part or selectively controlling emission of the therapeutic ultrasonic radiation.

In an embodiment, sensing one or more of the at least one characteristic of the at least one body part that is related to at least one of movement or a physiological state of the at least one body part can include sensing one or more of a motion of the subject, a motion of the at least one body part such as one or more limbs of the subject, a stationary condition of the subject, a stationary condition of the at least one body part such as one or more limbs of the subject, or at least one characteristic that is related to at least one of movement or a physiological state of a plurality of regions or a plurality of body parts, such as prior to or during application of a therapeutic treatment (e.g., therapeutic radiation or a medicament).

In an embodiment, the method 1300 can include transmitting one or more sensing signals from the one or more sensors to the control system.

In an embodiment, the one or more sensors includes at least one scanning ultrasound transducer configured to transmit and receive scanning ultrasonic radiation, and sensing one or more of at least one characteristic associated with movement or at least one characteristic of a region of at least one body part can include sensing the one or more of at least one characteristic associated with movement or at least one characteristic of a region of at least one body part with at least one scanning ultrasound transducer. In such embodiments, the scanning ultrasonic radiation can be a different wavelength, a different frequency, a different intensity, or emitted at a different time than the therapeutic ultrasonic radiation.

The act 1330 of responsive to sensing the at least one characteristic via the one or more sensors, actuating the array of ultrasound transducers to initiate, alter, or terminate application of the therapeutic ultrasonic radiation to the at least one body part can include sending one or more actuation signals to the array of ultrasound transducers. The one or more actuation signals can include operating instructions encoding directions for selected characteristics of emission of the therapeutic radiation. For example, the one or more actuation signals can include information selected to cause the therapeutic ultrasonic transducers to emit a selected frequency, wavelength, intensity, duration, or pattern of therapeutic ultrasonic radiation. The one or more actuation signals can include information selected to cause the therapeutic ultrasonic transducers to emit at least a second selected frequency, wavelength, intensity, duration, or pattern of therapeutic ultrasonic radiation, or direct the therapeutic ultrasonic radiation to a different region of the at least one body part than was originally targeted. The act 1330 responsive to sensing the at least one characteristic via the one or more sensors, actuating the array of ultrasound transducers to initiate, alter, or terminate application of the therapeutic ultrasonic radiation to the at least one body part can include can additionally or alternatively be responsive to a pre-programmed routine (e.g., a timed routine stored in the memory of the controller), direction from a remote device (e.g., remote control or computer), or direction of a user (as entered into the controller, remote control or computer). For example, actuating the array of ultrasound transducers to initiate, alter, or terminate application of the therapeutic ultrasonic radiation to the at least one body part can be responsive to one or both of sensing the at least one characteristic and a pre-programmed routine, wherein the pre-programmed routine is initiated by the sensing.

The act 1340 of emitting the therapeutic ultrasonic radiation from the array of ultrasound transducers into at least a first region of the at least one body part responsive to actuating the array of ultrasound transducers can include emitting a first frequency, wavelength, intensity, duration, or pattern of therapeutic ultrasonic radiation from at least one of from the array of ultrasound transducers (e.g., all, or all transducer around a specific region of the at least one body part). In an embodiment, emitting the therapeutic ultrasonic radiation to the at least one body part from the array of ultrasound emitters includes selectively emitting therapeutic ultrasonic radiation from the array of ultrasound transducers to a single region or point in the at least one body part.

In an embodiment, emitting the therapeutic ultrasonic radiation into at least a first region of the at least one body part is carried out at one or more of a wavelength, a frequency, an intensity, a duration, or a position effective to stimulate a tissue in the at least one body part, such as tissue in at least a first region or the at least a second region. In an embodiment, emitting the therapeutic ultrasonic radiation into at least a first region of the at least one body part is carried out at one or more of a wavelength, a frequency, an intensity, a duration, or a position effective to block pain receptors in the at least one body part, such as in at least a first region or the at least a second region thereof. In an embodiment, emitting the therapeutic ultrasonic radiation into at least a first region of the at least one body part is carried out at one or more of a wavelength, a frequency, an intensity, a duration, or a position effective to increase a temperature of tissue in the at least a first region or the at least a second region.

The act 1350 of selectively controlling emission of the therapeutic ultrasonic radiation to alter one or more of a wavelength, a frequency, or an intensity thereof or alter a target location of the therapeutic ultrasonic radiation from the first region to at least a second region of the at least one body part can include changing one or both of altering one or more of a first wavelength, a first frequency, or a first intensity; or altering a target location of the therapeutic ultrasonic radiation from the first region to at least a second region of the at least one body part.

In an embodiment, selectively controlling emission of the therapeutic ultrasonic radiation includes altering a target location of the therapeutic ultrasonic radiation. For example, altering a target location of the therapeutic ultrasonic radiation can include altering a target location of the therapeutic ultrasonic radiation from a first region or point to at least a second region or point. In an embodiment, selectively controlling emission of the therapeutic ultrasonic radiation includes altering one or more of a first wavelength, frequency, or intensity thereof applied in a first region to a second wavelength, frequency, or intensity thereof applied to the first region or to at least a second region. For example, selectively controlling emission of the therapeutic ultrasonic radiation can include applying a first therapeutic ultrasonic radiation to a first region and moving the target location to apply a second therapeutic ultrasonic radiation to a second region, wherein the first region is laterally and/or vertically spaced from the second region in the at least one body part. In an embodiment, altering a target location of the therapeutic ultrasonic radiation can include causing the array of ultrasound transducers to emit ultrasonic radiation at a different depth in the at least one body part than the at least a first region. In an embodiment, altering a target location of the therapeutic ultrasonic radiation can include causing the array of ultrasound transducers to emit ultrasonic radiation at a different lateral location in the at least one body part than the at least a first region.

In an embodiment, selectively controlling emission of the therapeutic ultrasonic radiation into at least a first region of the at least one body part is carried out at one or more of a wavelength, a frequency, an intensity, a duration, or a position effective to block pain receptors in the at least one body part, such as in at least a first region or the at least a second region thereof. In an embodiment, selectively controlling emission of the therapeutic ultrasonic radiation into at least a first region of the at least one body part is carried out at one or more of a wavelength, a frequency, an intensity, a duration, or a position effective to increase a temperature of tissue in the at least a first region or the at least a second region.

In an embodiment, one or both of emitting the therapeutic ultrasonic radiation into at least a first region of the at least one body part or selectively controlling emission of the therapeutic ultrasonic radiation can include selectively emitting the therapeutic ultrasonic radiation to a plurality of regions of the at least one body part from the array of ultrasound transducers. In an embodiment, one or both of emitting the therapeutic ultrasonic radiation into at least a first region of the at least one body part or selectively controlling emission of the therapeutic ultrasonic radiation can include applying the therapeutic ultrasonic radiation for a selected duration of time, such as any of the durations disclosed herein. In an embodiment, one or both of emitting the therapeutic ultrasonic radiation into at least a first region of the at least one body part or selectively controlling emission of the therapeutic ultrasonic radiation can include applying the therapeutic ultrasonic radiation according to one or more treatment regimens (e.g., a treatment regimen stored in operating instructions in the memory and executed by the control electrical circuitry). The treatment regimens can include a treatment regimen composed to selectively treat at least one medical condition. In an embodiment, the at least one medical condition can include one or more of arthritis, arthralgia, dehydration, muscle fatigue, muscle cramps, muscle spasms, neuropathic pain, muscular pain, or traumatic pain. In an embodiment, the one or more treatment regimens include at least one of an active treatment, a preventative treatment, or a palliative treatment.

In an embodiment, emitting the therapeutic ultrasonic radiation into at least a first region of the at least one body part can include selectively terminating or altering application of the therapeutic ultrasonic radiation to a first region, and selectively controlling emission of the therapeutic ultrasonic radiation can include applying therapeutic ultrasonic radiation to at least a second region of the at least one body part. In an embodiment, the first region can include a first depth of a tissue of the subject and the at least a second region can include at least a second depth of the tissue. In an embodiment, the first region can include a first tissue of the subject and the at least a second region can include at least a second tissue. For example, a first region can include a tendon and the at least a second region can include a muscle. In an embodiment, selectively controlling emission of the therapeutic ultrasonic radiation includes applying a different wavelength, a different frequency, or a different intensity of the therapeutic ultrasonic radiation (e.g., a second therapeutic ultrasonic radiation) than the therapeutic ultrasonic radiation emitted in the first region, effective to cause the therapeutic ultrasonic radiation to penetrate into the at least one body part to a different depth than in the at least a first region.

The method 1300 can include determining if an activation condition is present based on one or more of at least one characteristic of the at least one body part that is related to at least one of movement or a physiological state of the at least one body part, such as detected by the one or more sensors and determined by the control system. For example, the method 1300 can include determining that an activation condition (e.g., adjustment is necessary to the therapeutic ultrasonic radiation being applied) is present based on at least one physiological characteristic of a region of the at least one body part such as at least one of nerve activity of at least tissue in the region, an internal temperature of the region, an external temperature, blood flow in the region, tissue oxygenation in the region, a strain on the at least one body part, a conductance in the region, an impedance in the region, a pH in a body fluid in the region, an amount of a physiological analyte in the region, an acoustic emission from tissue in the region, biochemical activity in the region, or occurrence or cessation of any of the foregoing for a duration longer than a selected duration of time, as disclosed above. Determining at least one physiological characteristic of a region of the at least one body part can be carried out during application of the therapeutic ultrasonic radiation. In an embodiment, determining at least one characteristic of a region of the at least one body part (or an activation condition is present based thereon) can be continuously or intermittently carried out during one or both of emitting the therapeutic ultrasonic radiation into at least a first region of the at least one body part or selectively controlling emission of the therapeutic ultrasonic radiation. In an embodiment, one or both of emitting the therapeutic ultrasonic radiation into at least a first region of the at least one body part or selectively controlling emission of the therapeutic ultrasonic radiation can be responsive to determining at least one characteristic of a region of the at least one body part; determining that an activation condition is present based on the same; a pre-programmed routine; or direction from a remote control, computer, or user.

In an embodiment, one or both of emitting the therapeutic ultrasonic radiation into at least a first region of the at least one body part or selectively controlling emission of the therapeutic ultrasonic radiation can be responsive to determining at least one characteristic of a region of the at least one body part and can be controlled responsive to sensing signals provided by continuous or intermittent sensing during application of the therapeutic ultrasonic radiation. In such embodiments, the method can include continuously or intermittently sensing the one or more characteristics and continuously or intermittently determining if an activation condition is present.

In an embodiment, the method 1300 can include determining if the at least one characteristic of a region indicates a threshold level of the at least one characteristic has been reached, exceeded, or not met (e.g., an activation condition is present), substantially as described above with respect to method 1200. Determining if the at least one characteristic of a region indicates a threshold level of the at least one characteristic has been reached, exceeded, or not met can be carried out during application of the therapeutic ultrasonic radiation. In an embodiment, one or both of emitting the therapeutic ultrasonic radiation into at least a first region of the at least one body part or selectively controlling emission of the therapeutic ultrasonic radiation can be responsive to determining if the at least one characteristic indicates that a threshold level has been reached, exceeded, or not met.

The method 1300 can include determining that a subject is exhibiting a presence of an indication of pain, with the controller, such as via the one or more sensing signals. Determining that a subject is exhibiting a presence of an indication of pain can be as described above with respect to the method 1200, and can be carried out prior to or during application of therapeutic ultrasonic radiation. Emitting the therapeutic ultrasonic radiation into at least a first region of the at least one body part from the array of ultrasound transducers can be responsive to determining the subject is exhibiting of an indication of pain. Selectively controlling emission of the therapeutic ultrasonic radiation to alter one or more of a wavelength, a frequency, or an intensity thereof or alter a target location of the therapeutic ultrasonic radiation from the first region to at least a second region of the at least one body part can be responsive to determining that a subject is exhibiting a presence of an indication of pain, with the controller, such as via the one or more sensing signals In an embodiment, the method 1300 can include determining if the subject is in an inactive state, a duration since the subject initiated a physical activity, a duration since a last application of therapeutic ultrasonic radiation, a duration since application of therapeutic radiation initiated, with the control system using the one or more sensing signals. Determining if the subject is in an inactive state, a duration since the subject initiated a physical activity, a duration since a last application of therapeutic ultrasonic radiation, a duration since application of therapeutic radiation initiated can be as described above with respect to the method 1200. In an embodiment, determining if the subject is in an inactive state, a duration since the subject initiated a physical activity, a duration since a last application of therapeutic ultrasonic radiation, a duration since application of therapeutic radiation initiated can be carried during application of therapeutic ultrasonic radiation, and can be used to determine if adjustment of the therapeutic ultrasonic radiation currently being applied is required. In an embodiment, one or both of emitting the therapeutic ultrasonic radiation into at least a first region of the at least one body part or selectively controlling emission of the therapeutic ultrasonic radiation can be carried out at one or more of a wavelength, a frequency, an intensity, or a position effective to stimulate tissue in the at least a first region or the at least a second region, and/or can be responsive to determining if the subject is in an inactive state.

In an embodiment, the method 1300 can include determining if the at least one characteristic of a region indicates a muscle cramp, a muscle contraction, or muscle spasm in the at least one body part. Determining if the at least one characteristic of a region indicates a muscle cramp, a muscle contraction, or muscle spasm in the at least one body part can be carried out during application of therapeutic ultrasonic radiation. Determining if the at least one characteristic of a region indicates a muscle cramp, a muscle contraction, or muscle spasm in the at least one body part can be similar or identical to the same act described with respect to the method 1200. In an embodiment, one or both of emitting the therapeutic ultrasonic radiation into at least a first region of the at least one body part or selectively controlling emission of the therapeutic ultrasonic radiation can be responsive to determining if the at least one characteristic indicates a muscle cramp, a muscle contraction, or muscle spasm, and can be carried out during application of the therapeutic ultrasonic radiation.

In an embodiment, the garment system can include one or more compression actuators configured to cause at least a portion of the at least one flexible compression garment to compress against or relieve compression against the at least one body part, and the method 1300 can further include selectively actuating the one or more compression actuators to compress or relieve compression against the at least one body part. The garment system of method 1300 can include any of the compression actuators disclosed herein. Selectively actuating the one or more compression actuators to compress or relieve compression against the at least one body part can be carried out as described herein, in one or more aspects.

In an embodiment, the garment system of the method 1300 can include at least one medicament delivery device operably coupled to the control system of the garment system and is configured to provide topical, transdermal, or intramuscular medicament delivery to the at least one body part. The at least one medicament delivery device can be similar or identical to any of the medicament delivery devices disclosed herein, in one or more aspects. The method 1300 can include causing the at least one medicament delivery device to selectively deliver the at least one medicament, responsive to the one or more sensing signals indicative of the at least one characteristic, with the control system (e.g., controller). For example, causing the at least one medicament delivery device to selectively deliver the at least one medicament can include sending one or more actuation signals to the at least one medicament delivery device. The method 1300 can include actuating the at least one medicament delivery device to selectively deliver the at least one medicament, such as responsive to one or more actuation signals. In an embodiment, actuating the at least one medicament delivery device can include compressing or bursting a reservoir holding the one or more medicaments. Compressing the reservoir holding the one or more medicaments can include actuating a compression actuator disposed about the reservoir effective to cause the at least one medicament to be forced from the reservoir or to at least partially rupture that reservoir. In an embodiment, bursting a reservoir holding the one or more medicaments can include emitting acoustic radiation to the reservoir effective to at least partially rupture the at reservoir (e.g., disrupt or tear a containment layer thereof). Any of the above can be carried out dynamically, such as initiated, altered, or terminated during application of therapeutic radiation, compression, or the at least one medicament, responsive to one or more sensing signals or a determination based thereon (which can also be dynamically carried out during the application).

In an embodiment, the method 1300 can include transmitting one or more sensing signals from the one or more sensors to the controller. The method 1300 can include storing, in the memory storage medium, sensing signals from the one or more sensors and actuation data corresponding to actuation of the array of ultrasound transducers. In an embodiment, the control system can include a user interface having one or more visual, audio, or haptic outputs each configured to indicate an activation status of the garment system, such as communicate the activation status with a user. In an embodiment, the control system can include a user interface having one or more input devices (e.g., keyboard, buttons, touch screen, toggles, ports, drives, etc.) to accept input from a user. The method 1300 can include initiating, terminating, or adjusting application of radiation to the at least one body part from the array of ultrasound transducers with the user interface, such as manually entering (e.g., executing) a command to initiate, terminate, or adjust application of therapeutic ultrasonic radiation.

Individual acts or aspects of any of the methods or associated with any of the devices disclosed herein can be used with any of the methods disclosed herein.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A garment system for delivering therapeutic stimulation to a subject, the garment system comprising:
   at least one flexible compression garment configured to be worn on at least one body part of the subject, the at least one flexible compression garment defining an interior space configured to receive the at least one body part;
   one or more sensors positioned and configured to sense at least one characteristic of the at least one body part that is related to at least one of movement or a physiological state of the at least one body part, the one or more sensors further configured to output one or more sensing signals indicative of the at least one characteristic;
   at least one therapeutic stimulation delivery device ("TSDD") positioned and configured to apply radiation to the at least one body part;
   a controller operably coupled to the at least one TSDD and the one or more sensors to receive the one or more sensing signals therefrom, the controller including control electrical circuitry configured to direct the at least one TSDD to selectively apply radiation to a region of the at least one body part responsive to the one or more sensing signals.

2. The garment system of claim 1, wherein the at least one flexible compression garment is formed at least partially from at least one of neoprene, nylon, synthetic rubber, or fabric.

3. The garment system of claim 1, wherein the at least one flexible compression garment includes a portion that is substantially tubular and configured to generally conform to the at least one body part, wherein the at least one body part includes at least a portion of an arm, at least a portion of an elbow, at least a portion of a forearm, at least a portion of a wrist, at least a portion of a hand, at least a portion of a finger, at least a portion of a thigh, at least a portion of a knee, at least a portion of a lower leg, at least a portion of a foot, at least a portion of a toe, at least a portion of a neck, at least a portion of a head, at least a portion of a back, at least a portion of a spine, or at least a portion of a chest.

4. The garment system of claim 1, wherein the at least one characteristic of the at least one body part that is related to at least one of movement or a physiological state of the at least one body part includes at least one of nerve activity of at least tissue in the region, an internal temperature of the region, an external temperature, blood flow in the region, tissue oxygenation in the region, a strain on the at least one body part, a conductance in the region, an impedance in the region, a pH in a body fluid in the region, a chemical composition of a physiological analyte in the region, an acoustic emission from tissue in the region, a biochemical activity in the region, changes of any of the foregoing exceeding a threshold value, or cessation of any of the foregoing for a duration longer than a selected duration of time.

5. The garment system of claim 1, wherein the at least one characteristic of the at least one body part that is related to at least one of movement or a physiological state of the at least one body part includes one or more of a motion of the subject, a motion of one or more limbs of the subject, a stationary condition of the subject, or a stationary condition of one or more limbs of the subject.

6. The garment system of claim 1, wherein:
the one or more sensors are configured to sense characteristics indicative of onset of muscle activity, muscular fatigue, conclusion of muscle activity, a threshold level of muscle activity in the region, or pain; and
the control electrical circuitry is configured to direct the at least one TSDD to selectively initiate, terminate, or alter application of the radiation to the region of the at least one body part responsive to one or more sensed characteristics.

7. The garment system of claim 1, wherein the one or more sensors include at least one of an electrophysiological sensor, a myography sensor, a thermal sensor, a blood flow sensor, an oxygenation sensor, a chemical sensor, a motion sensor, a strain sensor, an electrode, a bioimpedance sensor, a pH sensor, or an acoustic sensor.

8. The garment system of claim 1, wherein the at least one flexible compression garment includes an interior surface that defines the interior space, and the one or more sensors are disposed at least partially on the interior surface.

9. The garment system of claim 1, wherein the at least one TSDD includes an ultrasound transducer configured to apply acoustic radiation to the at least one body part.

10. The garment system of claim 9, wherein the at least one ultrasound transducer is configured to apply acoustic radiation to the at least one body part effective to block one or more nerve signals.

11. The garment system of claim 9, wherein the at least one ultrasound transducer is configured to emit low frequency acoustic radiation.

12. The garment system of claim 9, wherein the at least one ultrasound transducer is configured to emit high intensity acoustic radiation.

13. The garment system of claim 9, wherein the at least one ultrasound transducer is configured to emit a wavelength and an intensity of acoustic radiation effective to alter or maintain a temperature of a portion of the at least one body part.

14. The garment system of claim 9, wherein the at least one TSDD includes a plurality of ultrasound transducers each positioned and configured to provide acoustic radiation to the at least one body part.

15. The garment system of claim 14, wherein the plurality of ultrasound transducers are arranged in an array to converge acoustic radiation in a common region in the at least one body part.

16. The garment system of claim 14, wherein the plurality of ultrasound transducers are configured to emit low frequency acoustic radiation.

17. The garment system of claim 1, wherein the at least one TSDD includes one or more of at least one electrode, at least one magnetic field generator, at least one optical stimulator, at least one thermal control device, or at least one microwave emitter.

18. The garment system of claim 1, wherein:
the one or more sensors includes at least one scanning acoustic transducer configured to apply scanning acoustic radiation to tissue of the at least one body part and receive reflected scanning acoustic radiation responsive thereto; and
the at least one TSDD includes a therapeutic ultrasound transducer configured to provide therapeutic acoustic radiation to the at least one body part.

19. The garment system of claim 1, wherein the at least one TSDD is individually adjustable to be aimed responsive to aiming instructions from the controller, wherein the aiming instructions are configured to direct the at least one TSDD to apply radiation to a region in which the one or more sensors provide data that the controller determines indicates an activation condition is present.

20. The garment system of claim 19, wherein:
the at least one TSDD includes a therapeutic ultrasonic transducer configured to emit therapeutic ultrasonic radiation to the region;
the one or more sensors include at least one scanning acoustic transducer configured to emit scanning ultrasonic radiation to the region; and
the controller is configured to direct the therapeutic ultrasonic transducer to aim the therapeutic ultrasonic radiation to a specific portion of the region responsive to sensor information detected by the scanning acoustic transducer.

21. The garment system of claim 1, wherein the at least one TSDD includes a plurality of TSDDs each of which is individually adjustable to be aimed at one or more portions of the at least one body part of the subject.

22. The garment system of claim 21, wherein:
the plurality of TSDDs includes a plurality of steerable therapeutic ultrasound transducers each of which is configured to emit therapeutic ultrasonic radiation; and
the one or more sensors include a plurality of sensing acoustic transducers each configured to emit scanning ultrasonic radiation; and
the controller is configured to independently direct at least one of the plurality of steerable therapeutic ultrasonic transducers to aim the therapeutic ultrasonic radiation therefrom to a first region of the at least one body part and at least some of the plurality of steerable therapeutic ultrasonic transducers to aim the therapeutic ultrasonic radiation therefrom to at least a second region of the at least one body part, responsive to sensor information detected by the plurality of sensing acoustic transducers.

23. The garment system of claim 22, wherein:
the one or more sensors include one or more acoustic sensors configured to stimulate the region of the at least one body part with acoustic radiation and receive reflected acoustic radiation responsive thereto; and
the controller is configured to determine a location to direct the therapeutic ultrasonic radiation from the plurality of steerable therapeutic ultrasonic transducers, based at least in part on the reflected acoustic radiation.

24. The garment system of claim 1, wherein:
the one or more sensors are configured to transmit sensed information to the controller; and
responsive to receipt of the sensed information, the processing electrical circuitry is configured to determine if an activation condition is indicated by the sensed information.

25. The garment system of claim 24, wherein the processing electrical circuitry is configured to determine if the activation condition is indicated by comparing the sensed information with one or more threshold levels stored in the memory storage medium corresponding to the sensed information, and determine if the sensed information exceeds the one or more threshold levels.

26. The garment system of claim 24, wherein responsive to receipt of the sensed information, the processing electrical circuitry is configured to selectively direct the at least one TSDD to initiate, terminate, or alter application of the radiation to the region responsive to a determination of a presence or absence of the activation condition.

27. The garment system of claim 25, wherein the activation condition includes one or more of a muscle cramp, a muscle spasm, or a muscle contraction.

28. The garment system of claim 25, wherein the activation condition includes one or more of a level of oxygenation, blood flow, pulse, heart rate, presence or amount an analyte, movement of the subject, or lack of movement of the subject for a selected duration.

29. The garment system of claim 25, wherein the activation condition includes one or more of an elapsed time since initiation of a level of movement of the subject, an elapsed time since termination of a level of movement of the subject; an elapsed time since termination of change of position of the subject; or an elapsed time since termination of movement of the subject.

30. The garment system of claim 24, wherein the controller is configured to selectively direct the at least one TSDD to initiate, terminate, or alter application of the radiation to the region responsive to a determination of a presence or absence of the activation condition only if the sensed information indicates that the subject is not moving or is at rest.

31. The garment system of claim 24, wherein controller is configured to selectively direct at least one TSDD to initiate, terminate, or alter application of the radiation to the region responsive to a determination of a presence or absence of the activation condition only if the sensed information indicates that the subject is moving in a specific pattern indicative of a specific activity, after an elapsed time of the specific activity of the subject, or after an elapsed time since termination of the specific activity of the subject.

32. The garment system of claim 24, wherein the controller is configured to receive the sensed information and determine a presence of an indication of pain.

33. The garment system of claim 32, wherein controller is configured to determine the presence of an indication of pain based one or more of nerve signals indicative of pain, an amount of one or more chemicals in a fluid of the subject, or a specific pattern of movement.

34. The garment system of claim 33, wherein the operational instructions include one or more treatment regimens configured to selectively treat at least one medical condition.

35. The garment system of claim 33, wherein the one or more sensors include one or more chemical sensors, and the controller is configured to determine if a chemical indication of pain is present based at least in part on a detected presence or change in concentration of one or more analytes.

36. The garment system of claim 35, wherein the one or more chemical sensors include one or more of a transdermal sensor, a reverse iontophoresis sensor, ion-selective electrodes, or an electrochemical sensor.

37. The garment system of claim 36, wherein the one or more analytes include one or more of a sugar, a salt, a lactate, an electrolyte, a hormone, a neuropeptide, a peptide, a protein, a nucleotide, derivatives of any of the foregoing, or oxygen.

38. The garment system of claim 36, wherein the one or chemical sensors are positioned and configured to determine an amount of the one or more analytes in sweat.

39. The garment system of claim 24, wherein the controller is further configured to direct the at least one TSDD to deliver the radiation responsive to a determination that the subject is exhibiting a presence of an indication of pain.

40. The garment system of claim 1, wherein the at least one flexible compression garment includes one or more compression actuators operably coupled to the controller, positioned relative to the at least one flexible compression garment, and configured to cause a portion of at least one flexible compression garment to selectively compress against or selectively relieve compression against the at least one body part.

41. The garment system of claim 40, wherein the controller is configured to cause the one or more compression actuators to selectively compress against or selectively relieve compression against the at least one body part, responsive to one or more sensing signals indicative of the at least one characteristic.

42. The garment system of claim 41, wherein the controller is configured to cause the one or more compression actuators to selectively compress against and selectively relieve compression against the at least one body part in an intermittent pattern, responsive to one or more sensing signals indicative of the at least one characteristic.

43. The garment system of claim 42, wherein the controller is configured to synchronize the intermittent pattern with blood flow in the at least one body part.

44. The garment system of claim 1, further including at least one medicament delivery device operably coupled to the controller and configured to provide topical, transdermal, or intramuscular medicament delivery to the at least one body part.

45. A garment system for delivering therapeutic stimulation to a subject, the garment system comprising:
   at least one flexible compression garment configured to be worn on at least one body part of a subject, the at least one flexible compression garment defining an interior space configured to receive the at least one body part;
   one or more sensors positioned and configured to sense at least one characteristic of the at least one body part that is related to at least one of movement or a physiological state of the at least one body part, the one or more sensors further configured to output one or more sensing signals indicative of the at least one characteristic;
   at least one therapeutic stimulation delivery device ("TSDD") positioned and configured to apply radiation to a region of the at least one body part;
   a controller operably coupled to the at least one TSDD and the one or more sensors to receive the one or more sensing signals therefrom, the controller including:
      processing electrical circuitry configured to direct the at least one TSDD to selectively apply radiation to the region of the at least one body part, responsive to one or more sensing signals; and
      a memory storage medium operably coupled to the processing electrical circuitry, the memory storage medium having one or more machine readable programs thereon, wherein the processing electrical circuitry is configured to execute the one or more machine readable programs; and
   a power supply operably coupled to the controller, the one or more sensors, and the at least one TSDD.

46. A method, comprising:
- receiving at least one flexible compression garment of a garment system on at least one body part of a subject, the garment system including:
  - one or more sensors positioned and configured to sense at least one characteristic of the at least one body part that is related to at least one of movement or a physiological state of the at least one body part, the one or more sensors further configured to output one or more sensing signals indicative of the at least one characteristic;
  - at least one therapeutic stimulation delivery device ("TSDD") positioned and configured to provide radiation to a region of the at least one body part; and
  - a controller operably coupled to the one or more sensors and the at least one TSDD;
- with the one or more sensors, sensing one or more of the at least one characteristic of the at least one body part that is related to at least one of movement or a physiological state of the at least one body part;
- with the controller, responsive to sensing the at least one characteristic via the one or more sensors, actuating the at least one TSDD to initiate, alter, or terminate application of radiation to the at least one body part; and
- selectively emitting the radiation to the at least one body part from the at least one TSDD.

* * * * *